US012599635B2

(12) United States Patent
Javan et al.

(10) Patent No.: US 12,599,635 B2
(45) Date of Patent: *Apr. 14, 2026

(54) COMPOSITIONS AND TREATMENTS FOR ISCHEMIC INJURIES

(71) Applicant: University of Utah Research Foundation, Salt Lake City, UT (US)

(72) Inventors: Hadi Javan, Salt Lake City, UT (US); Craig H. Selzman, Salt Lake City, UT (US); Young Sook Lee, Salt Lake City, UT (US); Jo-Anna Reems, Salt Lake City, UT (US); Jan L. Pierce, Sandy, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 757 days.

This patent is subject to a terminal disclaimer.

(21) Appl. No.: 17/912,730

(22) PCT Filed: Mar. 22, 2021

(86) PCT No.: PCT/US2021/023511
§ 371 (c)(1),
(2) Date: Sep. 19, 2022

(87) PCT Pub. No.: WO2021/194983
PCT Pub. Date: Sep. 30, 2021

(65) Prior Publication Data
US 2023/0149471 A1 May 18, 2023

Related U.S. Application Data

(60) Provisional application No. 62/993,614, filed on Mar. 23, 2020.

(51) Int. Cl.
| | |
|---|---|
| *A61K 35/50* | (2015.01) |
| *A61K 9/00* | (2006.01) |
| *A61K 31/728* | (2006.01) |
| *A61K 38/01* | (2006.01) |
| *A61K 45/06* | (2006.01) |
| *A61P 9/10* | (2006.01) |
| *A61P 43/00* | (2006.01) |

(52) U.S. Cl.
CPC ............ *A61K 35/50* (2013.01); *A61K 9/0019* (2013.01); *A61K 31/728* (2013.01); *A61K 38/014* (2013.01); *A61K 45/06* (2013.01); *A61P 9/10* (2018.01); *A61P 43/00* (2018.01)

(58) Field of Classification Search
CPC .... A61K 35/50; A61K 38/014; A61K 31/728; A61K 2300/00; A61P 9/10
See application file for complete search history.

(56) References Cited

U.S. PATENT DOCUMENTS

| | | |
|---|---|---|
| 10,517,903 B2 | 12/2019 | Beaudry et al. |
| 2016/0199417 A1 | 7/2016 | Werber et al. |
| 2018/0015128 A1 | 1/2018 | Britt |
| 2018/0250343 A1 | 9/2018 | Reems et al. |
| 2019/0083547 A1 | 3/2019 | Petrucci |

FOREIGN PATENT DOCUMENTS

| | | |
|---|---|---|
| WO | 2021202947 A1 | 10/2021 |
| WO | 2021205411 A1 | 10/2021 |
| WO | 2022104018 A1 | 5/2022 |

OTHER PUBLICATIONS

Kalogeris et al. "Cell Biology of Ischemia/Reperfusion Injury" International Review of Cell and Molecular Biology, vol. 298, p. 229-317 (Year: 2012).*
"Situs." Merriam-Webster.com Dictionary, Merriam-Webster, https://www.merriam-webster.com/dictionary/situs. Accessed Nov. 26, 2025. (Year: 2025).*
Balbi, C., et al. "The human amniotic fluid stem cell secretome as new paracrine source to unlock endogenous cardiac regeneration." Vascular Pharmacology 103 (2018): 47-48.
Bollini, S., et al. "Amniotic fluid stem cells are cardioprotective following acute myocardial infarction." Stem cells and development 20.11 (2011): 1985-1994.
Teodelinda, M. et al. "Amniotic liquid derived stem cells as reservoir of secreted angiogenic factors capable of stimulating neo-arteriogenesis in an ischemic model." Biomaterials 32.15 (2011): 3689-3699.
Hu, J., et al. "Exosomes derived from human amniotic fluid mesenchymal stem cells alleviate cardiac fibrosis via enhancing angiogenesis in vivo and in vitro." Cardiovascular diagnosis and therapy 11.2 (2021): 348.
Lee, Y. S., et al. "Acellular human amniotic fluid protects the ischemic-reperfused rat myocardium." American Journal of Physiology-Heart and Circulatory Physiology 322.3 (2022): H406-H416.
Javan, H., et al. "Acellular Human Amniotic Fluid Prevents the Development of Ischemic Heart Failure." The Journal of Heart and Lung Transplantation 42.4 (2023): S175.
European Patent Office. Extended European Search Report for Application No. 21776017.2, dated Mar. 13, 2024 (20 pages).
Adzick, N. S., et al. "Cells, matrix, growth factors, and the surgeon. The biology of scarless fetal wound repair." Annals of surgery 220.1 (1994): 10.
Ammendolia, C., et al. "Nonoperative treatment for lumbar spinal stenosis with neurogenic claudication." Cochrane Database of Systematic Reviews 8 (2013).
Asher AM, et al. Measuring clinically relevant improvement after lumbar spine surgery: is it time for something new? Spine J. Jun. 2020;20(6):847-856.
Babu, A. N., et al. "Local, national, and service component cost variations in the management of low back pain: Considerations for the clinician." Journal of Back and Musculoskeletal Rehabilitation 29.4 (2016): 685-692.

(Continued)

*Primary Examiner* — Thane Underdahl
(74) *Attorney, Agent, or Firm* — Michael Best & Friedrich LLP

(57) ABSTRACT
Described herein are compositions and methods for treating ischemic injury in a subject comprising administering a therapeutically effective amount of an acellular amniotic fluid (acAF) to an ischemic injury situs within a therapeutic time window.

31 Claims, 22 Drawing Sheets

(56)                    References Cited

OTHER PUBLICATIONS

Baker, R., et al. "Cervical transforaminal injection of corticosteroids into a radicular artery: a possible mechanism for spinal cord injury." Pain® 103.1-2 (2003): 211-215.

Benzon, H. T., et al. "Comparison of the particle sizes of different steroids and the effect of dilution: a review of the relative neurotoxicities of the steroids." The Journal of the American Society of Anesthesiologists 106.2 (2007): 331-338.

Bottai, D., et al. "Third trimester amniotic fluid cells with the capacity to develop neural phenotypes and with heterogeneity among sub-populations." Restorative Neurology and Neuroscience 30.1 (2012): 55-68.

Brouwers Pjam, et al. A cervical anterior spinal artery syndrome after diagnostic blockade of the right C6-nerve root. Pain. 2001: 397-399.

Carr C, et al. Adverse event rates in interventional spine procedures: A multi-institutional study. Pain Med. 2014;15 (8).

Castro-Combs J, et al. Corneal wound healing is modulated by topical application of amniotic fluid in an ex vivo organ culture model. Exp Eye Res. 2008: 56-63.

Chiu CC, et al. The probability of spontaneous regression of lumbar herniated disc: A systematic review. Clinical Rehabilitation. 2015: 184-195.

Clinical Trial—A Double-blinded, randomized, prospective study to evaluate the standard of care (Corticosteriod) vs. Sterile Amniotic Fluid Filtrate Epidural Injection for the treatment of Lumbosacral Radicular Pain due to Spinal Stenosis. (Univerity of Utah), Sep. 3, 2020 (Sep. 3, 2020 [online]. [Retrieved on Jan. 7, 2022]. Retrieved from the Internet <URL:https://clinicaltrials.gov/ct2/show/ NCT04537026> (5 pages).

Comer CM, et al. Internal construct validity of the Swiss Spine Stenosis Questionnaire: Rasch analysis of a disease-specific outcome measure for lumbar spinal stenosis. Spine (Phila Pa 1976). Feb. 1, 2011, 1969-1976.

Daffner SD, et al. The pathophysiology and nonsurgical treatment of lumbar spinal stenosis. Instr Course Lect. 2009: 657-668.

Derby, R., et al. "Size and aggregation of corticosteroids used for epidural injections." Pain Medicine 9.2 (2008): 227-234.

Deyo RA, et al. Report of the NIH task force on research standards for chronic low back pain. Pain Med (United States). 2014; e1-e18.

El-Yahchouchi C, et al. Complication rates of transforaminal and interlaminar epidural steroid injections: A multi-institutional study. Pain Med. 2014;15(8) 1436-1446.

El-Yahchouchi C, et al. The noninferiority of the nonparticulate steroid dexamethasone vs the particulate steroids petamethasone and triamcinolone in lumbar transforaminal epidural steroid injections. Pain Med (United States). 2013; 1650-1657.

Englund J. Lumbar spinal stenosis. Curr Sports Med Rep. 2007;6(1):50-55.

Friedly JL, et al. A randomized trial of epidural glucocorticoid injections for spinal stenosis. N Engl J Med. 2014; 11-21.

Friedly, J. et al. "Increases in lumbosacral injections in the Medicare population: 1994 to 2001." Spine 32.16 (2017): 1754-1760.

Fukusaki M, et al. Symptoms of spinal stenosis. Do not improve after epidural steroid injection. Clin J Pain. 1998; 148-151.

Gallizzi M, et al. Medication quantification scale Version III: Internal validation of detriment weight using a chronic bain population. Pain Pract. 2008; 1-4.

Gao X, et al. Effects of amniotic fluid on proteases: A possible role of amniotic fluid in fetal wound healing. Ann Plast Surg. 1994; 128-135.

Ghahreman A, et al. The efficacy of transforaminal injection of steroids for the treatment of lumbar radicular pain. Pain Med (United States). 2010; 1149-1168.

Glaser SE, et al. Paraplegia following a thoracolumbar transforaminal epidural steroid injection. Pain Physician. 2005; 309-314.

Houten JK, et al. Paraplegia after lumbosacral nerve root block: Report of three cases. Spine J. 2002; 70-75.

Huntoon MA, et al. Paralysis after transforaminal epidural injection and previous spinal surgery. Reg Anesth Pain Med. 2004; 494-495.

International Preliminary Report on Patentability for Application No. PCT/US2021/023511 dated Sep. 22, 2022 (7 pages).

International Search Report and Written Opinion for Application No. PCT/US2021/023511 dated Jul. 28, 2021 (11 pages).

International Search Report and Written Opinion for Application No. PCT/US2021/059082 dated Feb. 4, 2022 (14 pages).

Ismail MA, et al. Effect of amniotic fluid on bacterial recovery and growth: Clinical implications. Obstetrical and Gynecological Survey. 1989 571-577.

Johnson HL, et al.(1936) Amniotic fluid concentrate as an activator of peritoneal immunity. Surg Bynec Ostet 62:171-181.

Johnson HL. Peritoneal immunization. Am J Surg. 1936;34(2):266-71.

Karaçal. N, et al. Effect of human amniotic fluid on bone healing. J Surg Res. 2005; 283-287.

Kennedy DJ, et al. Epidural Steroid Injections are Safe and Effective: Multisociety Letter in Support of the Safety and Effectiveness of Epidural Steroid Injections. Pain Medicine (United States). 2015 833-838.

Kennedy DJ, et al. Paraplegia following image-guided transforaminal lumbar spine epidural steroid injection: Two case reports. Pain Med. 2009; 1389-1394.

Kobayashi S. Pathophysiology, diagnosis and treatment of intermittent claudication in patients with lumbar canal stenosis. World J Orthop. 2014; 134.

Kroszczynski AC, et al. Intraforaminal location of thoracolumbar anterior medullary arteries. Pain Med (United States). 2013; 808-812.

Lee, Y. S., et al. "177. Cross-Talk Between Human Relaxin Gene Therapy and Infarct-Related Coronary Artery." Molecular Therapy 24 (2016): S69.

Lu J, et al. Vulnerability of great medullary artery. In: Spine. 1996; 1852-1855.

Macedo LG, et al. Physical Therapy Interventions for Degenerative Lumbar Spinal Stenosis: A Systematic Review. Phys Ther. 2013; 1646-1660.

Manchikanti L, et al. Assessment of the growth of epidural injections in the medicare population from 2000 to 2011. Pain Physician. 2013; E349-E364.

Manchikanti L, et al. Preliminary results of a randomized, equivalence trial of fluoroscopic caudal epidural injections in managing chronic low back pain: Part 4—Spinal stenosis. Pain Physician. 2008; 833-848.

Melancia JL, et al. Spinal stenosis. In: Handbook of clinical neurology. Elsevier; 2014. p. 541-9.

Merimee TJ, et al. Insulin-like growth factors in amniotic fluid. J Clin Endocrinol Metab. 1984;59(4):752-5.

Muro K, et al. Infarction of the cervical spinal cord following multilevel transforaminal epidural steroid injection: Case report and review of the literature. J Spinal Cord Med. 2007; 385-388.

Nahm FS, et al. Risk of intravascular injection in transforaminal epidural injections. Anaesthesia. 2010; 917-921.

Nesbitt LT. Minimizing complications from systemic glucocorticosteroid use. Dermatologic Clinics. 1995; 925-939.

Nyman E, et al. Hyaluronic acid, an important factor in the wound healing properties of amniotic fluid: In vitro studies of re-epithelialisation in human skin wounds. J Plast Surg Hand Surg. 2013; 89-92.

International Preliminary Report on Patentability for the Application No. PCT/US2021/059082 dated on May 16, 2023 (8 pages).

Khedr, E. M., et al. "Neurological complications of ankylosing spondylitis: neurophysiological assessment." Rheumatology international 29.9 (2009): 1031-1040.

Ojo VA, et al. Antimicrobial properties of amniotic fluid from some Nigerian women. Int J Gynecol Obstet. 1986;24(2):97-101.

Ostelo RW, et al. Interpreting change scores for pain and functional status in low back pain: towards international consensus regarding minimal important change. Spine (Phila Pa 1976) 2008;33(1):90-4.

Overdevest GM, et al. Effectiveness of posterior decompression techniques compared with conventional laminectomy for lumbar stenosis. Cochrane Database of Systematic Reviews. 2015; 1-76.

(56)                    References Cited

OTHER PUBLICATIONS

Özgenel GY, et al. Effects of human amniotic fluid on cartilage regeneration from free perichondrial grafts in rabbits. Br J Plast Surg. 2004; 423-428.

Özgenel GY, et al. Effects of human amniotic fluid on peripheral nerve scarring and regeneration in rats. J Neurosurg. 2003; 371-377.

Pierce J, et al. Collection and characterization of amniotic fluid from scheduled C-section deliveries. Cell Tissue Bank. 2016;17(3):413-25.

Plastaras C, et al. Fluoroscopically Guided Lumbosacral Transforaminal Epidural Steroid Injections: Adverse Events and Predictive Factors. 2015; (33 pages).

Prusa AR, et al. Oct-4-expressing cells in human amniotic fluid: A new source for stem cell research? Hum Reprod. 2003; 1489-1493.

Quintero N, et al. Transforaminal epidural steroid injection and paraplegia: case report and bibliographic review. In: Annales de readaptation et de medecine physique: revue scientifique de la Societe francaise de reeducation fonctionnelle de readaptation et de medecine physique. 2006. p. 242-7.

Radloff LS. The CES-D scale: A self-report depression scale for research in the general population. Applied Psychological Measurement. 1977;1:385-401.

Shimberg M. The use of amniotic-fluid concentrate in orthopaedic conditions. JBJS. 1938;20(1):167-77.

Smith CC, et al. The effectiveness of lumbar transforaminal injection of steroid for the treatment of radicular pain: a comprehensive review of the published data. Pain Med. 2020; 472-487.

Somayaji HS, et al. Spinal cord infarction following therapeutic computed tomography-guided left L2 nerve root injection. Spine (Phila Pa 1976). 2005; E106-E108.

Stucki G, et al. Measurement properties of a self-administered outcome measure in lumbar spinal stenosis. Spine 1996; 21: 796-803.

Underwood MA, et al. Amniotic fluid: not just fetal urine anymore. (State of the Art)(Report). J Perinatol. 2005, 341-348.

Weinstein JN, et al. Surgical versus nonsurgical therapy for lumbar spinal stenosis. N Engl J Med. 2008; 794-810.

Weissenbacher T, et al. Influence of maternal age, gestational age and fetal gender on expression of immune mediators in amniotic fluid. BMC Res Notes. 2012, 5:375.

\* cited by examiner

*In vivo* Model in Rats

Ischemic Heart Failure        Non-Ischemic Heart Failure

Permanent ligation of
left anterior descending
(LAD) coronary artery

30–60 min temporary
occlusion of left anterior
descending (LAD)
coronary artery

Chemotherapeutic
induced non-ischemic
heart failure

NS (90 min)

h-acAF (90 min)

5 mm 90 min                                    0 min

Sham + N/S          N/S (90 min)          N/S (0 min)

Sham + hAF          hAF (90 min)          hAF (00 min)

NS                    h-acAF

Sample #

···⊙··· Control

--⊟-- Sham

--▲-- h-acAF Single Pre

- ◆ - h-acAF Single Post

~ ■~ h-acAF Single Post 24 h

—●- h-acAF 5 day

—⊖— NS

COMPOSITIONS AND TREATMENTS FOR ISCHEMIC INJURIES

CROSS REFERENCE TO RELATED APPLICATIONS

This application is a U.S. national stage entry of International Patent Application No. PCT/US2021/023511, filed on Mar. 22, 2021, which claims priority to U.S. Provisional Patent Application No. 62/993,614, filed on Mar. 23, 2020, the entire contents of each of which are fully incorporated herein by reference.

TECHNICAL FIELD

Described herein are compositions and methods for treating ischemic injury in a subject comprising administering a therapeutically effective amount of an acellular amniotic fluid (acAF) to an ischemic injury situs within a therapeutic time window.

BACKGROUND

Cardiovascular disease is one of the leading causes of death globally. In the United States, 37% of people between the ages of 40 and 60 have cardiovascular disease, while 71% of people between the ages of 60 and 80 have cardiovascular disease. It has been estimated that almost 90% of cardiovascular disease can be prevented. Myocardial infarction is a type of cardiovascular disease that refers to tissue death of the heart muscle (e.g., fibrosis). Myocardial infarction can result when blood flow to the heart is limited as occurs in ischemic heart disease. Ischemic heart disease can occur due to the accumulation of plaque or other materials in the arteries of the heart.

Ischemic heart failure (iHF) after myocardial infarction is a major cause of morbidity and mortality in the world. The incidence for patients with clinical iHF has been in decline; however, the incidence remains high at about 30-50%. The 5-year mortality rate of iHF is about 50% even with the recent developments in therapeutics and increased healthcare expenditures. Procedures such as percutaneous coronary intervention (PCI) and coronary artery bypass surgery have been used in treatment, but while they can be life extending, they are traumatic invasive protocols that come with a number of drawbacks and undesirable side effects. Diverse molecular and cellular pathogenesis and pathophysiology have been explored to understand the disease mechanisms of iHF and to find potential cardio-protective or regenerative therapeutics. Isolated single pathways or proteins are insufficient to provide therapeutics for ischemic heart injury. Efficacies of single targeted therapy are limited followed by diverse feedback systems and resistance to therapy.

What is needed are compositions and methods for treating ischemic injuries.

SUMMARY

One embodiment described herein is a method of treating an ischemic injury in a subject, comprising: administering a therapeutically effective amount of an acellular amniotic fluid (acAF) to an ischemic injury situs within a therapeutic time window. In one aspect, the acAF is substantially free of cells and debris. In another aspect, the ischemic injury situs is an organ selected from: a heart, a brain, a limb, a large intestine, a small intestine, a stomach, a liver, a gallbladder, a pancreas, a lung, a kidney, a lymph node, a thymus, a spleen, a skeletal muscle, a smooth muscle, a cardiac muscle, an artery, a vein, or combinations thereof. In another aspect, the therapeutic time window includes one or more of: 30 minutes, 60 minutes, one day, 1 week, 2 weeks, or 4 weeks. In another aspect, administration is performed via one or more of: an intravenous injection, or an injection proximate to the ischemic injury situs. In another aspect, the therapeutically effective amount of acAF has less than or equal to 10,000 particles per milliliter of particles having a particle size of 10 microns or greater. In another aspect, the therapeutically effective amount of acAF has less than or equal to 300 particles per milliliter of particles having a particle size of 25 microns or greater. In another aspect, the therapeutically effective amount of acAF has an optical density of less than 0.20 when exposed to electromagnetic radiation at a wavelength of 590 nm. In another aspect, the therapeutically effective amount of acAF further comprises hemoglobin in an amount from 1 µg/mL to 60 µg/mL. In another aspect, the therapeutically effective amount of acAF further comprises an active agent. In another aspect, the active agent is an anti-infective agent, an antibiotic, an anti-tumor agent, an anti-inflammatory agent, a pain-controlling agent, an anti-rheumatic agent, a bisphosphonate, a supplementary growth factor, a supplementary cytokine, an amino acid, a protein, a vaccine, a hormone, a vitamin, a phytoestrogen, a fluoride, or combinations thereof. In another aspect, the active agent is: angiotensin-converting enzyme (ACE) inhibitors, aldosterone inhibitors, angiotensin II receptor blockers (ARBs), beta-blockers, calcium channel blockers, cholesterol-lowering drugs, digoxin, diuretics, potassium, magnesium, proprotein convertase subtilisin kexin type 9 (PCSK9) inhibitors, vasodilators, warfarin, or combinations thereof. In another aspect, the active agent further comprises stem cells. In another aspect, the therapeutically effective amount of acAF further comprises a pharmaceutically acceptable carrier. In another aspect, the therapeutically effective amount includes a volume of therapeutic composition of from about 0.1 mL to about 1000 mL. In another aspect, the therapeutically effective amount includes an amount of total protein from about 0.1 mg to about 2500 mg. In another aspect, the therapeutically effective amount includes an amount of hyaluronic acid (HA) from about 0.1 mg to about 2500 mg. A method of treating a cardiac ischemic event in a subject, comprising: administering a therapeutically effective amount of acellular amniotic fluid (acAF) to an ischemic situs of a heart of the subject within a therapeutic time window. In another aspect, the therapeutic time window includes one or more of: 30 minutes, 60 minutes, one day, 1 week, 2 weeks, or 4 weeks. In another aspect, administration is performed via one or more of: direct administration into a myocardium of the heart of the subject via an epicardial injection or an endocardial injection; intravenous injection to the subject; intracoronary administration; or direct administration to a coronary vein of the heart of the subject via a local injection. In another aspect, administration is performed concomitantly with a procedure directed to the heart of the subject, wherein the procedure includes one or more of: cardiac catheterization, coronary angioplasty, balloon angioplasty, coronary artery stent, atherectomy, laser angioplasty, coronary artery bypass surgery, intra-aortic balloon pump surgery, ventricular assist device (VAD) surgery, heart transplant surgery, valvuloplasty, valve repair surgery, valve replacement surgery, or combinations thereof. In another aspect, the therapeutically effective amount of acAF has less than or equal to 10,000 particles per milliliter of particles having a particle size of 10 microns or greater. In another aspect, the therapeutically effective amount of acAF has less than or equal to 300 particles per milliliter of particles having a particle size of 25 microns or greater. In another aspect, the therapeutically effective amount of acAF has an optical density of less than 0.20 when exposed to electromagnetic radiation at a wavelength of 590 nm. In another aspect, the therapeutically effective amount of acAF further comprises a pharmaceutically acceptable carrier. In another aspect, the therapeutically effective amount includes a volume of therapeutic composition of from about 25 µL to about 25 mL. In another aspect, the therapeutically effective amount of acAF further comprises an active agent selected from: angiotensin-converting enzyme (ACE) inhibitors, aldosterone inhibitors, angiotensin II receptor blockers (ARBs), beta-blockers, calcium channel blockers, cholesterol-lowering drugs, digoxin, diuretics, potassium, magnesium, proprotein convertase subtilisin kexin type 9 (PCSK9) inhibitors, vasodilators, warfarin, or combinations thereof.

Another embodiment described herein is a system of treating an ischemic injury of a subject, comprising: a therapeutic composition, comprising: a therapeutically effective amount of acellular amniotic fluid (acAF); an administration device configured to administer the acAF to the subject. In another aspect, the administration device comprises one or more of: an infusion pump, a hypodermic needle, a drip chamber, a peripheral cannula, a pressure bag, an auto-injector, or a syringe. In another aspect, the composition has less than or equal to 10,000 particles per milliliter of particles having a particle size of 10 microns or greater. In another aspect, the composition has less than or equal to 300 particles per milliliter of particles having a particle size of 25 microns or greater. In another aspect, the composition has an optical density of less than 0.20 when exposed to electromagnetic radiation at a wavelength of 590 nm. In another aspect, the composition further comprises hemoglobin in an amount from 1 µg/mL to 60 µg/mL. In another aspect, the composition further comprises an active agent. In another aspect, the active agent is an anti-infective agent, an antibiotic, an anti-tumor agent, an anti-inflammatory agent, a pain-controlling agent, an anti-rheumatic agent, a bisphosphonate, a supplementary growth factor, a supplementary cytokine, an amino acid, a protein, a vaccine, a hormone, a vitamin, a phytoestrogen, a fluoride, or combinations thereof. In another aspect, the active agent further comprises stem cells. In another aspect, the composition further comprises a pharmaceutically acceptable carrier. In another aspect, the composition includes a volume of therapeutic composition of from about 0.1 mL to about 1000 mL. In another aspect, the composition includes an amount of total protein from about 0.1 mg to about 2500 mg. In another aspect, the composition includes an amount of hyaluronic acid (HA) from about 0.1 mg to about 2500 mg.

Another embodiment described herein is a method of treating fibrosis in a subject, comprising: administering a therapeutically effective amount of acellular amniotic fluid (acAF) to an ischemic situs of the subject within a therapeutic time window.

Another embodiment described herein is a method of treating peripheral arterial disease (PAD) in a subject, comprising: administering a therapeutically effective amount of acellular amniotic fluid (acAF) to an ischemic situs of a lower extremity of the subject within a therapeutic time window.

Another embodiment described herein is a method of treating cyanosis in a subject, comprising: administering a therapeutically effective amount of acellular amniotic fluid (acAF) to an ischemic situs of an extremity of the subject, wherein the therapeutically effective amount is administered via a dosage regimen.

BRIEF DESCRIPTION OF THE DRAWINGS

FIG. 4A—90 min; FIG. 4B—0 min.

FIG. 4C—90 min; FIG. 4D—0 min.

FIG. 4E—90 min; FIG. 4F—0 min.

FIG. 7A shows the heart weight:body weight ratio; FIG. 7B shows the wet lung weight:body weight; FIG. 7C shows the wet lung weight:dry lung weight ratio (P<0.05, *vs NS treated).

DETAILED DESCRIPTION

Figure 1A:
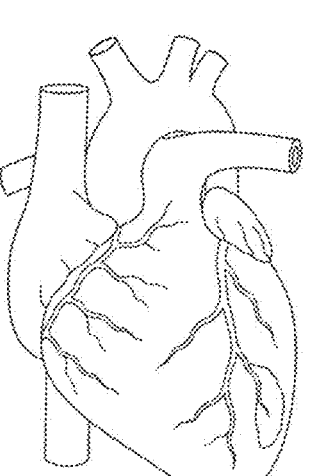
FIG. 1A illustrates the in vivo model in rats for an ischemic heart failure (iHF) model with permanent ligation or ischemia/reperfusion (I/R) injury by a temporary ligation of proximal left anterior descending (LAD) coronary artery and a non-ischemic heart failure model.
Figure 1A:
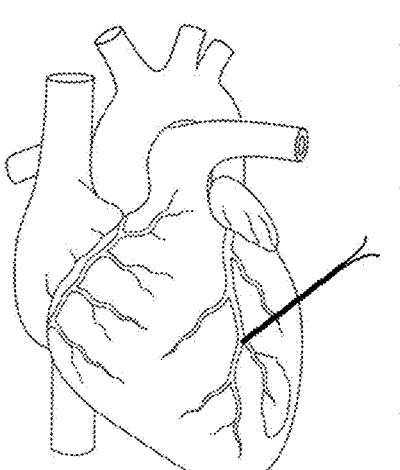
Figure 1A:
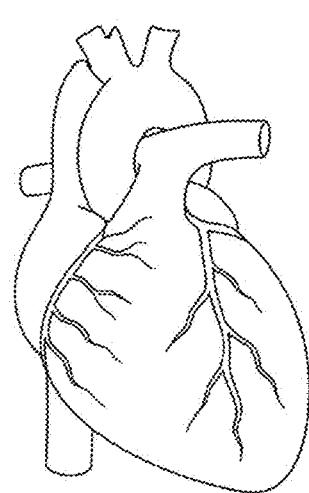

Unless otherwise defined, all technical and scientific terms used herein have the same meaning as commonly understood by one of ordinary skill in the art. For example, any nomenclatures used in connection with, and techniques of, cell and tissue culture, molecular biology, immunology, microbiology, genetics, and protein and nucleic acid chemistry and hybridization described herein are well known and commonly used in the art. In case of conflict, the present document, including definitions, will control. Preferred methods and materials are described below, although methods and materials similar or equivalent to those described herein can be used in practice or testing of the present invention.

As used herein, the terms such as "include," "including," "contain," "containing," "having," and the like mean "comprising." The present disclosure also contemplates other embodiments "comprising," "consisting of," and "consisting essentially of," the embodiments or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "," "an," or "the" means "one or more" unless otherwise specified.

As used herein, the term "or" can be conjunctive or disjunctive.

As used herein, the term "substantially" means to a great or significant extent, but not completely.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to ±10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "~" means "about" or "approximately."

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to ±10% of any value within the range or within 3 or more standard deviations, including the end points.

As used herein, the terms "active ingredient" or "active pharmaceutical ingredient" refer to a pharmaceutical agent, active ingredient, compound, or substance, compositions, or mixtures thereof, that provide a pharmacological, often beneficial, effect.

As used herein, the terms "control," or "reference" are used herein interchangeably. A "reference" or "control" level may be a predetermined value or range, which is employed as a baseline or benchmark against which to assess a measured result. "Control" also refers to control experiments or control cells.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

The term "amniotic fluid agent" refers to any protein, hyaluronic acid (HA), or other component typically found in amniotic fluid to which an adverse health condition may be responsive and that is present in a therapeutic composition as described herein. In one embodiment, the "amniotic fluid agent" can be harvested with the amniotic fluid of the therapeutic composition, can be supplemented into the therapeutic composition, or a combination thereof.

As used herein, the term "dose" denotes any form of an active ingredient formulation or composition, including cells, that contains an amount sufficient to initiate or produce a therapeutic effect with at least one or more administrations. In one aspect, the terms "dosage unit" or "dose" are understood to mean an amount of an active agent that is suitable for administration to a subject in order achieve or otherwise contribute to a therapeutic effect. In one embodiment, a dosage unit can refer to a single dose that is capable of being administered to a subject or patient, and that may be readily handled and packed, remaining as a physically and chemically stable unit dose.

As used herein, a "dosing regimen" or "regimen" refers to how, when, how much, and for how long a dose of a given composition is to be administered to a subject.

As used herein, the terms "effective amount" or "therapeutically effective amount," refers to a substantially non-toxic, but sufficient amount of an agent, composition, or cell(s) being administered to a subject that will prevent, treat, or ameliorate to some extent one or more of the symptoms of the disease or condition being experienced or that the subject is susceptible to contracting. The result can be the reduction or alleviation of the signs, symptoms, or causes of a disease, or any other desired alteration of a biological system. An effective amount may be based on factors individual to each subject, including, but not limited to, the subject's age, size, type or extent of disease, stage of the disease, route of administration, the type or extent of supplemental therapy used, ongoing disease process, and type of treatment desired. It is understood that various biological factors may affect the ability of a substance to perform its intended task. Therefore, an "effective amount," "therapeutically effective amount," or "therapeutically effective rate(s)" may be dependent in some instances on such biological factors. Further, while the achievement of therapeutic effects may be measured by physician or other qualified medical personnel using evaluations known in the art, it is recognized that individual variation and response to treatments may make the achievement of therapeutic effects a subjective decision. The determination of a therapeutically effective amount or delivery rate is well within the ordinary skill in the art of pharmaceutical sciences and medicine.

As used herein, "formulation" and "composition" can be used interchangeably and refer to a combination of at least two ingredients. In some embodiments, at least one ingredient may be an active agent or otherwise have properties that exert physiologic activity when administered to a subject. For example, amniotic fluid includes at least two ingredients (e.g., water and electrolytes) and is itself a composition or formulation.

As used herein, "acellular" refers to a substantial absence of viable amniotic cells. In some aspects, an acellular composition can have no or substantially no intact amniotic cells.

As used herein, an "ischemic injury situs" refers to an area of tissue that is negatively impacted by an ischemic event. For example, an area of tissue to which a blood supply is diminished or stopped because of an ischemic event would be at least part of the site of an ischemic injury. Furthermore, an "ischemic situs" refers to the location of a blockage in a vascular system and can, but need not necessarily be, a part of an ischemic injury situs if little or no tissue damage occurs at the blockage or obstruction site.

As used herein, a "therapeutic time window", "therapeutic window of time", "therapeutic window", and the like may be used interchangeably and refer to a period of time either before or after an ischemic event within which administration of a treatment provides a positive effect (e.g., a therapeutic effect) such as minimizing or reducing an ischemic injury as compared to a treatment made outside of a certain window of time.

As used herein, a subject is "in need of treatment" if such subject would benefit biologically, medically, or in quality of life from such treatment. A subject in need of treatment does not necessarily present symptoms, particular in the case of preventative or prophylaxis treatments.

As used herein, the terms "inhibit," "inhibition," or "inhibiting" refer to the reduction or suppression of a given biological process, condition, symptom, disorder, or disease, or a significant decrease in the baseline activity of a biological activity or process.

As used herein, "treatment" or "treating" refers to prophylaxis of, preventing, suppressing, repressing, reversing, alleviating, ameliorating, or inhibiting the progress of biological process including a disorder or disease, or completely eliminating a disease. A treatment may be either performed in an acute or chronic way. The term "treatment" also refers to reducing the severity of a disease or symptoms associated with such disease prior to affliction with the disease. "Repressing" or "ameliorating" a disease, disorder, or the symptoms thereof involves administering a cell, composition, or compound described herein to a subject after clinical appearance of such disease, disorder, or its symptoms. "Prophylaxis of" or "preventing" a disease, disorder, or the symptoms thereof involves administering a cell, composition, or compound described herein to a subject prior to onset of the disease, disorder, or the symptoms thereof. "Suppressing" a disease or disorder involves administering a cell, composition, or compound described herein to a subject after induction of the disease or disorder thereof but before its clinical appearance or symptoms thereof have manifest.

In one embodiment, the terms "treat," "treating," "treatment," and the like when used in conjunction with the administration of acellular amniotic fluid (acAF) refer to the administration of the acAF to a subject who is either asymptomatic or symptomatic. In other words, "treatment" can both reduce or eliminate symptoms associated with a condition or it can be prophylactic treatment (i.e., to prevent the occurrence of symptoms). Such prophylactic treatment can also be referred to as prevention of the condition.

As used herein, the term "prophylaxis" refers to preventing or reducing the progression of a disorder, either to a statistically significant degree or to a degree detectable by a person of ordinary skill in the art.

As used herein, the term "subject" refers to an animal. Typically, the subject is a mammal. A subject also refers to primates (e.g., humans, male or female; infant, adolescent, or adult), non-human primates, rats, mice, rabbits, pigs, cows, sheep, goats, horses, dogs, cats, fish, birds, and the like. In one embodiment, the subject is a human. In one embodiment, the human subject is a male. In another embodiment, the human subject is a female.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

This same principle applies to ranges reciting only one numerical value as a minimum or a maximum. Furthermore, such an interpretation should apply regardless of the breadth of the range or the characteristics being described.

Reference in this application may be made to compositions, systems, or methods that provide "improved" or "enhanced" performance. It is to be understood that unless otherwise stated, such "improvement" or "enhancement" is a measure of a benefit obtained based on a comparison to compositions, systems, or methods in the prior art. Furthermore, it is to be understood that the degree of improved or enhanced performance may vary between disclosed embodiments and that no equality or consistency in the amount, degree, or realization of improvement or enhancement is to be assumed as universally applicable.

Reference throughout this specification to "one embodiment" or "another embodiment" means that a particular feature, structure, or characteristic described in connection with the example is included in at least one aspect of that embodiment. Thus, appearances of the phrases "in one embodiment" or "another embodiment" in various places throughout this specification are not necessarily all referring to the same embodiment.

An initial overview of the embodiments is provided below, and specific embodiments are then described in further detail. This initial summary is intended to aid readers in understanding the technological concepts more quickly but is not intended to identify key or essential features thereof, nor is it intended to limit the scope of the claimed subject matter.

The present disclosure is drawn to methods of treating an ischemic injury in a subject. Such methods comprise administering a therapeutically effective amount of an acellular amniotic fluid (acAF) to an ischemic injury situs within a therapeutic time window. In one embodiment, the acAF can be free of, or substantially free of, cells and debris. In another embodiment, the ischemic injury situs can be an organ selected from: a heart, a brain, a limb, a large intestine, a small intestine, a stomach, a liver, a gallbladder, a pancreas, a lung, a kidney, a lymph node, a thymus, a spleen, a skeletal muscle, a smooth muscle, a cardiac muscle, an artery, a vein, or combinations thereof, including organ transplantation. Organs from donors are exposed to ischemia reperfusion injury until transplantation. Since the first human heart transplantation performed by Barnard in 1967, donor heart preservation is a core issue to minimize graft dysfunction caused by ischemia reperfusion injury which inevitably occurs during the ex vivo transplant interval. Ices of specific physiologic solutions, such as the histidine-tryptophan-ketoglutarate (HTK) solution, University of Wisconsin (UW) solution and Celsior solution are most commonly used for donor heart preservation. In another embodiment, the therapeutic time window can include one or more of: 30 minutes, 60 minutes, one day, 1 week, 2 weeks, or 4 weeks, either prior to, or following an ischemic event. In another embodiment, administration can be performed via one or more of: an intravenous injection, or an injection proximate to the ischemic injury situs.

In another embodiment, a method of treating a cardiac ischemic event in a subject comprises: administering a therapeutically effective amount of acellular amniotic fluid (acAF) to an ischemic situs of a heart of the subject within a therapeutic time window. In one embodiment, the therapeutic time window can include one or more of: 30 minutes, 60 minutes, one day, 1 week, 2 weeks, or 4 weeks, either prior to or following an ischemic event. In another embodiment, administration can be performed via one or more of: direct administration (during percutaneous coronary intervention or open heart surgery) into a myocardium of the heart of the subject via an epicardial injection or an endocardial injection or an intramyocardial; intravenous injection or infusion to the subject; intracoronary administration; inhalation; ex vivo administration for donor organ preservation; or direct administration to a coronary artery or vein of the heart of the subject via a local injection.

In another embodiment, administration can be performed concomitantly with a procedure directed to the heart of the subject, wherein the procedure includes one or more of cardiac intervention procedures and open heart: cardiac catheterization, coronary angioplasty, balloon angioplasty, coronary artery stent, atherectomy, laser angioplasty, coronary artery bypass surgery, intra-aortic balloon pump surgery, ventricular assist device (VAD) surgery, heart transplant surgery, valvuloplasty, valve repair surgery, valve replacement surgery, or combinations thereof.

In another embodiment, the therapeutically effective amount of acAF can further comprise an active agent, wherein the active agent is: angiotensin-converting enzyme (ACE) inhibitors, aldosterone inhibitors, angiotensin II receptor blockers (ARBs), beta-blockers, calcium channel blockers, cholesterol-lowering drugs, digoxin, diuretics, potassium, magnesium, proprotein convertase subtilisin kexin type 9 (PCSK9) inhibitors, vasodilators, warfarin, or combinations thereof.

In another embodiment, a system of treating an ischemic injury of a subject comprises: a therapeutic composition and an administration device. The therapeutic composition comprises a therapeutically effective amount of acellular amniotic fluid (acAF). The administration device can be configured to administer the acAF to the subject.

In another embodiment, a method of treating fibrosis, injury, or ischemia in a subject comprises: administering a therapeutically effective amount of acellular amniotic fluid (acAF) to an ischemic situs of the subject within a therapeutic time window.

In another embodiment, a method of treating peripheral arterial disease (PAD) in a subject comprises: administering a therapeutically effective amount of acellular amniotic fluid (acAF) to an ischemic situs of a lower extremity of the subject within a therapeutic time window.

In another embodiment, a method of treating cyanosis in a subject comprises: administering a therapeutically effective amount of acellular amniotic fluid (acAF) to an ischemic situs of an extremity of the subject, wherein the therapeutically effective amount if administered via a dosage regimen.

With this overview in mind, the methods and associated systems will be described in further detail. Amniotic fluid (AF) can be a rich source of nutrients, cytokines, chemokines, and growth factors that are valuable for fetal development and maturation. Additionally, AF can also contain stem cells with the potential to differentiate along multiple cell lineages. Further, AF can have a number of powerful protective and regenerative properties dominantly with immune-modulatory and anti-inflammatory proteins, which can be provided via the exchange of water and solutes with surrounding tissues. This process can be accomplished via the utilization of different pathways during the course of a pregnancy that likely contribute to changes in the composition of the AF with gestational age.

Because of the beneficial combination of nutrients, cytokines, growth factors, and the like that are present in AF, a variety of adverse health conditions can be responsive to therapeutic treatment with AF. For example, in some cases, acellular AF can be used in the treatment of an ischemic injury.

A method of treating an ischemic injury in a subject using acAF has various advantages over previous therapies. Less than 1% of injected stem cells remain in the human body after 24 hours. The homing effect of multi-potent stem cells can be difficult to achieve in the target lesion site of diseases. Generally, cell therapy clinical trials have been inconsistent and produce minimal enhancements in cardiac functions of heart failure patients.

Acellular amniotic fluid does not use the long preparation time that stem cell therapy uses. Unlike single gene therapy or protein therapy, acAF includes hundreds of natural allogenic proteins predominantly with anti-inflammatory or immuno-modulatory properties. Acellular amniotic fluid can enhance cardiac function and cardiac geometry with a wide therapeutic window. Acellular amniotic fluid can also enhance, prevent, or restore acute and delayed histopathological recovery and regeneration and can also relieve heart and lung congestion.

In another embodiment, a method of treating an ischemic injury in a subject comprises: administering a therapeutically effective amount of an acellular amniotic fluid (acAF) to an ischemic injury situs within a therapeutic time window. The ischemic injury situs can be an organ selected from: a heart, a brain, a limb, a large intestine, a small intestine, a stomach, a liver, a gallbladder, a pancreas, a lung, a kidney, a lymph node, a thymus, a spleen, a skeletal muscle, a smooth muscle, a cardiac muscle, an artery, a vein, or combinations thereof. The therapeutic time window can include one or more of: 30 minutes, 60 minutes, one day, 1 week, 2 weeks, or 4 weeks.

In some example, indictors or risk factors for ischemic injury can be determined for administration of a therapeutically effective amount of acAF to an ischemic injury situs within a therapeutic time window. In another embodiment, one or more risk factors can be present. In one example, angina can be an indicator or risk factor for an ischemic injury in the heart.

In another embodiment, administration can be performed via one or more of: an intravenous injection, or an injection proximate to the ischemic injury situs. In another embodiment, when the ischemic injury situs is the heart, administration can be performed via one or more of: direct administration into a myocardium of the heart of the subject via an epicardial injection or an endocardial injection; intravenous injection to the subject; intracoronary administration; or direct administration to a coronary artery or vein of the heart of the subject via a local injection.

In another embodiment, administration can be performed via an administration device. In another embodiment, the administration device comprises one or more of: an infusion pump, a hypodermic needle, a drip chamber, a peripheral cannula, a pressure bag, an auto-injector, or a syringe.

In some example, administration can be performed concomitantly with a procedure directed to the heart of the subject, wherein the procedure includes one or more of cardiac intervention procedures and open heart surgeries: cardiac catheterization, coronary angioplasty, balloon angioplasty, coronary artery stent, atherectomy, laser angioplasty, coronary artery bypass surgery, intra-aortic balloon pump surgery, ventricular assist device (VAD) surgery, heart transplant surgery, valvuloplasty, valve repair surgery, valve replacement surgery, or combinations thereof.

Thus, a method of treating an ischemic injury in a subject can be valuable in treating a variety of adverse health conditions. However, it can also be beneficial to remove a variety of components that are present in harvested amniotic fluid, such cells present in the harvested amniotic fluid. Thus, the therapeutic composition can be processed to remove cells harvested with or from the amniotic fluid.

Processed amniotic fluid can have a variety of other properties that are not present in freshly harvested amniotic fluid. In another embodiment, the processed amniotic fluid can have a reduced amount of particulate matter as compared to freshly harvested amniotic fluid. In some specific examples, the processed amniotic fluid can have less than 10,000 particles per mL of particles having a particle size of 10 microns or greater. In another embodiment, the processed amniotic fluid can have less than 5000 particles per mL of particles having a particle size of 10 microns or greater. In yet other examples, the processed amniotic fluid can have less than 1000, less than 500, or less than 300 particles per mL of particles having a particle size of 10 microns or greater.

In some additional examples, the processed amniotic fluid can have less than 300 particles per mL of particles having a particle size of 25 microns or greater. In another embodiment, the processed amniotic fluid can have less than 200 particles per mL of particles having a particle size of 25 microns or greater. In yet other examples, the processed amniotic fluid can have less than 100, less than 50, or less than 30 particles per mL of particles having a particle size of 25 microns or greater.

Processed amniotic fluid can also have a greater optical clarity (i.e., lower optical density) than freshly harvested amniotic fluid. For example, processed amniotic fluid can have an optical density of less than 0.20 when exposed to electromagnetic radiation at a wavelength of 590 nm, 570 nm, 550 nm, 540 nm, 500 nm, or 450 nm. In further examples, processed amniotic fluid can have an optical density of less than 0.15 when exposed to electromagnetic radiation at a wavelength of 590 nm, 570 nm, 550 nm, 540 nm, 500 nm, or 450 nm. In yet other examples, processed amniotic fluid can have an optical density of less than 0.10 when exposed to electromagnetic radiation at a wavelength of 590 nm, 570 nm, 550 nm, 540 nm, 500 nm, or 450 nm.

Processed amniotic fluid can also include a reduced amount of hemoglobin as compared to freshly harvested amniotic fluid. For example, processed amniotic fluid can include hemoglobin in an amount of from about 1 μg/mL to about 60 μg/mL. In another embodiment, processed amniotic fluid can include hemoglobin in an amount of from about 5 μg/mL to about 50 μg/mL. In yet other examples, processed amniotic fluid can include hemoglobin in an amount of from about 10 μg/mL to about 40 μg/mL.

While processing can remove some constituents from the amniotic fluid, some beneficial constituents can be largely preserved. For example, the processed amniotic fluid can retain a comparable amount of total protein as found in freshly harvested amniotic fluid. More specifically, total protein content for the amniotic fluid composition can typically be within the range of about 0.15 mg/mL to about 10 mg/mL. In some specific examples, the amniotic fluid can include from about 0.5 mg/mL to about 5 mg/mL of total protein. In yet other examples, the amniotic fluid can include from about 1 mg/mL to about 3.0 or 3.5 mg/mL of total protein.

Further, the processed amniotic fluid can still include effective amounts of HA. For example, HA can typically be present in the amniotic fluid in an amount greater than or equal to 150 ng/mL. In some specific examples, HA can be present in the amniotic fluid in an amount from about 150 ng/mL to about 500 ng/mL. In another embodiment, HA can be present in the amniotic fluid in an amount from about 350 ng/mL to about 450 ng/mL. In yet other examples, HA can be present in an amount from about 300 ng/mL to about 400 ng/mL, 410 ng/mL, or 420 ng/mL.

Further, the processed amniotic fluid can still include effective amounts of epidermal growth factor (EGF). For example, EGF can typically be present in the amniotic fluid in an amount greater than or equal to 100 ng/mL. In some specific examples, EGF can be present in the amniotic fluid in an amount from about 100 ng/mL to about 500 ng/mL. In another embodiment, EGF can be present in the amniotic fluid in an amount from about 100 ng/mL to about 400 ng/mL. In yet other examples, HA can be present in an amount from about 150 ng/mL to about 250 ng/mL.

It is noted that a variety of protein concentrations, HA concentrations, particles counts, optical densities, and the like are provided herein to help describe the processed amniotic fluid included in the therapeutic composition. Where such values are provided, these values generally refer to the processed amniotic fluid that is otherwise undiluted, unconcentrated, or a combination thereof, unless otherwise specified. However, this is not intended to exclude the use of diluted and/or concentrated amniotic fluid compositions. Thus, where the amount of amniotic fluid has been diluted, concentrated, or a combination thereof, the various values recited herein describing the amniotic fluid still apply to a corresponding amniotic fluid composition that is in an undiluted and/or unconcentrated state, unless otherwise specified.

As described above, a therapeutically effective amount of at least one protein, HA, or both can depend on a variety of factors. In many cases, a therapeutically effective amount can include the amounts recited above. However, in some cases, it can be desirable to either concentrate or dilute the amniotic fluid. In another embodiment, concentration of the amniotic fluid can be performed via evaporation, lyophilization, or other equivalent or similar process. In some specific examples, the amount of amniotic fluid can be or can include an amount of lyophilized amniotic fluid. Where this is the case, the lyophilized amniotic fluid can typically have a water content of from about 0.1 wt % to about 10 wt % prior to any desired subsequent dilution. The amniotic fluid can also be concentrated by fortifying or supplementing the amniotic fluid with at least one protein, HA, or both, as desired for a particular application of the therapeutic composition.

Thus, in some examples, the therapeutic composition can include only processed amniotic fluid, which can be diluted and/or concentrated as desired. In another embodiment, the therapeutic composition can be fortified or supplemented with at least one protein that can typically be naturally found in amniotic fluid. In yet other examples, the therapeutic composition can be fortified with HA. In some specific examples, the therapeutic composition can be fortified with a cytokine. In other specific examples, the therapeutic composition can be fortified with a growth factor, such as epidermal growth factor, for example. In additional examples, the therapeutic composition can be fortified with other constituents that can typically be naturally found in amniotic fluid, such as stem cells, nutrients, electrolytes, etc. In yet additional examples, the therapeutic composition can include an active agent that is not typically found in amniotic fluid.

Thus, the therapeutic composition can include a variety of additives and active agents. Non-limiting examples can include an anti-infective agent, an anti-tumor agent, an anti-inflammatory agent, a pain-controlling agent, an anti-rheumatic agent, a bisphosphonate, a supplementary growth factor, a supplementary cytokine, an amino acid, a protein, a vaccine, a hormone, a vitamin, a phytoestrogen, fluoride, the like, or combinations thereof.

Anti-infective agents can typically include a variety of active agents that can kill or prevent an infectious organism from spreading. Thus, anti-infective agents can include antibacterial agents, antifungal agents, antiviral agents, anti-protozoan agents, the like, or combinations thereof. Non-limiting examples can include amebicides such as chloroquine, nitazoxanide, paromomycin, tinidazole, metronidazole, iodoquinol, or the like; aminoglycosides such as tobramycin, gentamicin, amikacin, kanamycin, neomycin, streptomycin, or the like; anthelmintics such as albendazole, ivermectin, praziquantel, pyrantel, mebendazole, miltefosine, niclosamide, piperazine, thiabendazole, or the like; antifungals such as itraconazole, posaconazole, ketoconazole, fluconazole, clotrimazole, isavuconazole, miconazole, voriconazole, echinocandins, terbinafine, griseofulvin, flucytosine, nystatin, amphotericin b, or the like; antimalarials such as chloroquine, quinine, hydroxychloroquine, mefloquine, primaquine, pyrimethamine, halofantrine, doxycycline, or the like; antituberculosis agents such as aminosalicylic acid, bedaquiline, isoniazid, ethambutol, pyrazinamide, ethionamide, rifampin, rifabutin, rifapentine, capreomycin, cycloserine, streptomycin, or the like; antivirals such as amantadine, rimantadine, ritonavir, cobicistat, peginterferon alfa-2a, peginterferon alfa 2b, maraviroc, raltegravir, dolutegravir, elvitegravir, sofosbuvir, enfuvirtide, fomivirsen, foscarnet, oseltamivir, zanamivir, peramivir, etravirine, efavirenz, nevirapine, delavirdine, rilpivirine, daclatasvir, adefovir, entecavir, telbivudine, didanosine, tenofovir, abacavir, lamivudine, zidovudine, stavudine, emtricitabine, zalcitabine, boceprevir, simeprevir, fosamprenavir, lopinavir, darunavir, telaprevir, ritonavir, tipranavir, atazanavir, nelfinavir, amprenavir, indinavir, saquinavir, ganciclovir, valacyclovir, famciclovir, acyclovir, valganciclovir, ribavirin, cidofovir, or the like; carbapenems such as doripenem, meropenem, cilastatin, ertapenem, or the like; cephalosporins such as avibactam, ceftolozane, ceftazidime, tazobactam, cefadroxil, cephalexin, cefazolin, ceftaroline, loracarbef, cefotetan, cefuroxime, cefprozil, cefaclor, cefoxitin, ceftibuten, cefotaxime, ceftriaxone, cefpodoxime, cefixime, cefdinir, defditoren, ceftazidime, ceftizoxime, cefepime, or the like; glycopeptide antibiotics such as vancomycin, dalbavancin, oritavancin, telavancin, or the like;

glycocyclines such as tigecycline, or the like; leprostatics such as thalidomide, dapsone, clofazimine, or the like; lincomycin, or the like; clindamycin, or the like; ketolides such as telithromycin, or the like; macrolides such as azithromycin, fidaxomicin, erythromycin, clarithromycin, or the like; antibiotics such as aztreonam, daptomycin, chloramphenicol, colistimethate, fosfomycin, rifaximin, metronidazole, sulfamethoxazole, atovaquone, bacitracin, dalfopristin, erythromycin, furazolidone, pentamidine, polymyxin b, spectinomycin, trimetrexate, linezolid, tedizolid, penicillins (e.g., ampicillin, amoxicillin, carbenicillin, piperacillin, ticarcillin, nafcillin, dicloxacillin, cloxacillin, oxacillin, or the like), quinolones (e.g., lomefloxacin, norfloxacin, ofloxacin, gatifloxacin, moxifloxacin, ciprofloxacin, levofloxacin, gemifloxacin, cinoxacin, nalidixic acid, sparfloxacin, or the like), sulfonamides (e.g., sulfamethoxazole, sulfadiazine, sulfisoxazole, or the like), tetracyclines (e.g., tetracycline, demeclocycline, doxycycline, minocycline, or the like), or the like; urinary anti-infectives such as methenamine, methylene blue, fosfomycin, nitrofurantoin, trimethoprim, cinoxacin, nalidixic acid, oxytetracycline, or the like; hydrates thereof, acids thereof, bases thereof, salts thereof, or combinations of any of such anti-infective agents.

In another embodiment, the therapeutic agent can also include any suitable antitumor agent. Non-limiting examples of antitumor agents can include angiogenesis inhibitors such as angiostatin k1-3, angiostatin k1-5, D/L-α-difluoromethylornithine, endostatin, fumagillin, genistein, minocycline, staurosporine, (±)-thalidomide, or the like; DNA intercalators such as bleomycin, carboplatin, carmustine, chlorambucil, cisplatin, cyclophosphamide, cis-diammineplatinum (II) dichloride, melphalan, mitoxantrone, oxaliplatin, or the like; DNA synthesis inhibitors such as (±)-amethopterin, 3-amino-1,2,4-benzotraizine-1,4-dioxide, aminopterin, cytosine β-D-arabinofuranoside, 5-fluoro-5'-deoxyuridine, 5-fluorouracil, ganciclovir, hydroxyurea, mitomycin C, or the like; transcription regulators such as actinomycin D, daunorubicin, doxorubicin, homoharringtonine, idarubicin, or the like; enzyme inhibitors such as S(+)-camptothecin, curcumin, (−)-deguelin, 5,6-dichlorobenzimidazole 1-β-D-ribofuranoside, etoposide, formestane, fostriecin, hispidin, 2-imino-1-imidazolidineacetic acid, mevinolin, trichostatin A, tyrphostin AG 34, tyrphostin AG 879, or the like; gene regulation agents such as 5-aza-2'-deoxycytidine, 5-azacytidine, cholecalciferol, 4-hydroxytamoxifen, melatonin, mifepristone, raloxifene, vitamin A aldehyde, vitamin A acid, vitamin A, 9-cis-retinoic acid, 13-cis-retinoic acid, tamoxifen, troglitazone, or the like; microtubule inhibitors such as colchicine, docetaxel, dolastatin 15, etoposide, irinotecan, nocodazole, paclitaxel, podophyllotoxin, rhizoxin, vinblastine, vincristine, vindesine, vinorelbine, or the like; other antitumor agents such as 17-(allylamino)-17-demethoxygeldanamycin, 4-amino-1,8-naphthalimide, apigenin, brefeldin A, cimetidine, dichloromethylene-diphosphonic acid, leuprolide, luteinizing hormone-releasing hormone, pifithrin-α, rapamycin, sex hormone-binding globulin, thapsigargin, bikunin, ifosfamide, temozolomide, capecitabine, methotrexate, gemcitabine, pemetrexed, mitomycin, epirubicin, bevacizumab, cetuximab, gefitinib, imatinib, trastuzumab, denosumab, rituximab, sunitinib, zoledronate, abiraterone, anastrozole, bicalutamide, exemestane, goserelin, medroxyprogesterone, octreotide, tamoxifen, bendamustine, lomustine, procarbazine, streptozocin, fludarabine, raltitrexed, mitoxantrone, eribulin, topotecan, afatinib, aflibercept, BCG, crizotinib, dabrafenib, interferon, ipilimumab, lapatinib, nivolumab, panitumumab, pembrolizumab, pertuzumab, sorafenib, trastuzumab emtansine, temsirolimus, vemurafenib, ibandronic acid, pamidronate, bexarotene, buserelin, cyproterone, degarelix, folinic acid, fulvestrant, lanreotide, lenalidomide, letrozole, leuprorelin, megestrol, mesna, thalidomide, or the like; hydrates thereof, acids thereof, bases thereof, salts thereof, or combinations of any of such antitumor agents.

In another embodiment, the therapeutic composition can also include any suitable anti-inflammatory agent. Non-limiting examples of anti-inflammatory agents can include ibuprofen, naproxen, aspirin, diclofenac, celecoxib, sulindac, oxaprozin, piroxicam, indomethacin, meloxicam, fenoprofen, diflunisal, etodolac, ketorolac, meclofenamate, nabumetone, salsalate, ketoprofen, tolmetin, flurbiprofen, mefenamic acid, famotidine, bromfenac, nepafenac, prednisone, cortisone, hydrocortisone, methylprednisolone, deflazacort, prednisolone, fludrocortisone, amcinonide, betamethasone diproprionate, clobetasol, clocortolone, dexamethasone, diflorasone, dutasteride, flumethasone pivalate, flunisolide, fluocinolone acetonide, fluocinonide, fluorometholone, fluticasone propionate, flurandrenolide, hydroflumethiazide, the like, hydrates thereof, acids thereof, bases thereof, or salts thereof, or combinations thereof.

In another embodiment, the therapeutic composition can also include any suitable pain-controlling agent. Non-limiting examples of pain controlling agents can include anti-inflammatory agents, such as those listed above, acetaminophen, codeine, dihydrocodeine, tramadol, meperidine, hydrocodone, oxycodone, morphine, fentanyl, hydromorphone, buprenorphine, methadone, diamorphine, pethidine, the like, hydrates thereof, acids thereof, bases thereof, or salts thereof, or combinations thereof.

In another embodiment, the therapeutic composition can also include any suitable anti-rheumatic agent. Non-limiting examples of anti-rheumatic agents can include methotrexate, sulfasalazine, chloroquine, hydroxychloroquine, leflunomide, azathioprine, cyclosporine, minocycline, abatacept, rituximab, tocilizumab, anakinra, adalimumab, etanercept, infliximab, cetolizumab, golimumab, D-penicillamine, auranofin, the like, hydrates thereof, acids thereof, bases thereof, or salts thereof, or combinations thereof.

In another embodiment, the therapeutic composition can also include any suitable bisphosphonate. Non-limiting examples of bisphosphonates can include alendronate, etidronate, zoledronate, ibandronate, alendronate, risedronate, pamidronate, tiludronate, clodronate, neridronate, olpadronate, the like, hydrates thereof, acids thereof, bases thereof, or salts thereof, or combinations thereof.

In another embodiment, the therapeutic composition can also include any suitable growth factor. Non-limiting examples of supplementary growth factors can include platelet-derived growth factor (PDGF), epidermal growth factor (EGF), transforming growth factor-alpha (TGF-α), fibroblast growth factor (FGF), nerve growth factor (NGF), erythropoietin, transforming growth factor-beta (TGF-β), insulin-like growth factor-1 (IGF-1), insulin-like growth factor-2 (IGF-2), the like, or combinations thereof.

In another embodiment, the therapeutic composition can also include any suitable supplementary cytokine. Non-limiting examples of supplementary cytokines can include interleukins, lymphokines, monokines, interferons, colony stimulating factors, chemokines, the like, or combinations thereof.

In another embodiment, the therapeutic composition can also include any suitable amino acid. Non-limiting examples can include arginine, histidine, isoleucine, leucine, lysine, methionine, phenylalanine, tryptophan, valine, acetyl-L-carinatine arginate, alpha-aminoadipic acid, alpha-amino-N- butyric acid, beta-alanine, beta-amino-isobutyric acid, carnosine, citrulline, gamma-amino butyric acid, hydroxyproline, 1-methylhistidine, 3-methylhistidine, N-acetyl-L-cysteine, ornithine, para-aminobenzoic acid, phosphoserine, phosphoethanolamine, taurine, the like, isomers thereof, hydrates thereof, salts thereof, acids thereof, bases thereof, or any combinations thereof.

In another embodiment, the therapeutic composition can also include any suitable protein. Non-limiting examples can include cytokines and/or growth factors, such as those listed above, as well as antibodies, Fc-fusion proteins, anticoagulants, blood factors, bone morphogenetic proteins, engineered protein scaffolds, enzymes, hormones, thrombolytics, the like, or combinations thereof.

In another embodiment, the therapeutic composition can also include a vaccine. Non-limiting examples of vaccines can include adenovirus vaccine, coxsackie B vaccine, cytomegalovirus vaccine, dengue vaccine, Eastern equine encephalitis vaccine, ebola vaccine, enterovirus vaccine, Epstein-barr vaccine, hepatitis A vaccine, hepatitis B vaccine, hepatitis C vaccine, hepatitis E vaccine, HIV vaccine, human papillomavirus vaccine, HTLV-1 T-lymphotrophic vaccine, influenza vaccine, Japanese encephalitis vaccine, Marburg vaccine, measles vaccine, mumps vaccine, norovirus vaccine, polio vaccine, rabies vaccine, respiratory syncytial virus (RSV) vaccine, rotavirus vaccine, rubella vaccine, severe acute respiratory syndrome (SARS) vaccine, varicella vaccine, smallpox vaccine, West Nile virus vaccine, yellow fever vaccine, anthrax vaccine, DPT vaccine, Q fever vaccine, Hib vaccine, tuberculosis vaccine, meningococcal vaccine, typhoid vaccine, pneumococcal vaccine, cholera vaccine, caries vaccine, ehrlichiosis vaccine, leprosy vaccine, lyme disease vaccine, *Staphylococcus aureus* vaccine, *Streptococcus pyogenes* vaccine, syphilis vaccine, tularemia vaccine, *Yersinia pestis* vaccine, the like, or combinations thereof.

In another embodiment, the therapeutic composition can also include a hormone. Non-limiting examples of hormones can include progestogens, androgens, estrogens, somatostatins, growth hormones, thyroid hormones, glucocorticoids, the like, or combinations thereof.

In another embodiment, the therapeutic composition can also include a vitamin. Non-limiting vitamins can include vitamin A, vitamin B1, vitamin B2, vitamin B6, vitamin B12, vitamin C, vitamin D, vitamin E, vitamin H, vitamin K, folic acid, the like, or combinations thereof.

In another embodiment, the therapeutic composition can also include a variety of additional supplementary agents, such as phytoestrogens, fluoride, calcium, iron, magnesium, zinc, any other suitable active agent, or combinations thereof. In some additional examples, the therapeutic composition can include tissue or other cells obtained or derived from the placenta, bone marrow, the umbilical cord, amniotic membrane, amniotic-chorionic membrane, adipose tissue, peripheral blood, or the skin, for example. In some specific examples, the cells can be stem cells. In another embodiment, the stem cells can be cells that are reprogrammed to function as stem cells. In another embodiment, the cells can be osteogenic cells.

In another embodiment, various active and/or supplementary agents can be added directly to the amniotic fluid without addition of other constituents. However, in other examples, the therapeutic composition can further comprise a pharmaceutically acceptable carrier to facilitate delivery of the amniotic fluid, the active and/or supplementary agent, or both. Where a pharmaceutically acceptable carrier is employed, the amniotic fluid combined with the pharmaceutically acceptable carrier can be in either liquid or solid form (e.g., lyophilized amniotic fluid).

Further, the pharmaceutically acceptable carrier can be formulated to provide a therapeutic composition that can be administered via various modes of administration. For example, the pharmaceutically acceptable carrier can be formulated to administer the therapeutic composition via intravenous injection, or an injection proximate to the ischemic injury, or the like.

In some example, administration can be performed via one or more of: an intravenous injection, or an injection proximate to the ischemic injury situs. In another embodiment, administration can be performed via one or more of: direct administration into a myocardium of the heart of the subject via an epicardial injection or an endocardial injection; intravenous injection to the subject; intracoronary administration; or direct administration to a coronary vein of the heart of the subject via a local injection.

In another embodiment, administration can be performed concomitantly with a procedure directed to the heart of the subject, wherein the procedure includes one or more of: cardiac catheterization, coronary angioplasty, balloon angioplasty, coronary artery stent, atherectomy, laser angioplasty, coronary artery bypass surgery, intra-aortic balloon pump surgery, ventricular assist device (VAD) surgery, heart transplant surgery, valvuloplasty, valve repair surgery, valve replacement surgery, or combinations thereof.

In another embodiment, the pharmaceutically acceptable carrier can be formulated to provide a therapeutic composition for administration via injection, such as intramuscular injection, intravenous injection, subcutaneous injection, intradermal injection, intrathecal injection, intraocular injection, or the like. In such examples, the pharmaceutically acceptable carrier can include a variety of components, such as water, a solubilizing or dispersing agent, a tonicity agent, a pH adjuster or buffering agent, a preservative, a chelating agent, a bulking agent, the like, or a combination thereof.

In another embodiment, an injectable therapeutic composition can include a solubilizing or dispersing agent. Non-limiting examples of solubilizing or dispersing agents can include polyoxyethylene sorbitan monooleates, lecithin, polyoxyethylene polyoxypropylene co-polymers, propylene glycol, glycerin, ethanol, polyethylene glycols, sorbitol, dimethylacetamide, polyethoxylated castor oils, n-lactamide, cyclodextrins, carboxymethyl cellulose, acacia, gelatin, methyl cellulose, polyvinyl pyrrolidone, the like, or combinations thereof.

In another embodiment, an injectable therapeutic composition can include a tonicity agent. Non-limiting examples of tonicity agents can include sodium chloride, potassium chloride, calcium chloride, magnesium chloride, mannitol, sorbitol, dextrose, glycerin, propylene glycol, ethanol, trehalose, phosphate-buffered saline (PBS), Dulbecco's PBS, Alsever's solution, Tris-buffered saline (TBS), water, balanced salt solutions (BSS), such as Hank's BSS, Earle's BSS, Grey's BSS, Puck's BSS, Simm's BSS, Tyrode's BSS, and BSS Plus, the like, or combinations thereof. The tonicity agent can be used to provide an appropriate tonicity of the therapeutic composition. In one aspect, the tonicity of the therapeutic composition can be from about 250 to about 350 milliosmoles/liter (mOsm/L). In another aspect, the tonicity of the therapeutic composition can be from about 277 to about 310 mOsm/L.

In another embodiment, an injectable therapeutic composition can include a pH adjuster or buffering agent. Non-limiting examples of pH adjusters or buffering agents can include a number of acids, bases, and combinations thereof, such as hydrochloric acid, phosphoric acid, citric acid, sodium hydroxide, potassium hydroxide, calcium hydroxide, acetate buffers, citrate buffers, tartrate buffers, phosphate buffers, triethanolamine (TRIS) buffers, the like, or combinations thereof. Typically, the pH of the therapeutic composition can be from about 5 to about 9, or from about 6 to about 8.

In another embodiment, an injectable therapeutic composition can include a preservative. Non-limiting examples of preservatives can include ascorbic acid, acetylcysteine, bisulfite, metabisulfite, monothioglycerol, phenol, metacresol, benzyl alcohol, methyl paraben, propyl paraben, butyl paraben, benzalkonium chloride, benzethonium chloride, butylated hydroxyl toluene, myristyl γ-picolinium chloride, 2-phenoxyethanol, phenyl mercuric nitrate, chlorobutanol, thimerosal, tocopherols, the like, or combinations thereof.

In another embodiment, an injectable therapeutic composition can include a chelating agent. Non-limiting examples of chelating agents can include ethylenediaminetetra acetic acid, calcium, calcium disodium, versetamide, calteridol, diethylenetriaminepenta acetic acid, the like, or combinations thereof.

In another embodiment, an injectable therapeutic composition can include a bulking agent. Non-limiting examples of bulking agents can include sucrose, lactose, trehalose, mannitol, sorbitol, glucose, raffinose, glycine, histidine, polyvinyl pyrrolidone, the like, or combinations thereof.

In another embodiment, the therapeutically effective amount of acAF can further comprise an active agent, wherein the active agent is: angiotensin-converting enzyme (ACE) inhibitors, aldosterone inhibitors, angiotensin II receptor blockers (ARBs), beta-blockers, calcium channel blockers, cholesterol-lowering drugs, digoxin, diuretics, potassium, magnesium, proprotein convertase subtilisin kexin type 9 (PCSK9) inhibitors, vasodilators, warfarin, the like, or combinations thereof.

In another embodiment, ACE inhibitors comprise: captopril, enalapril, lisinopril, benazepril, fosinopril, Ramipril, quinapril, perindopril, trandolapril, moexipril, the like, or combinations thereof.

In another embodiment, aldosterone inhibitors comprise: spironolactone, eplerenone, canrenone, finerenone, mexrenone, the like, or combinations thereof.

In another embodiment, ARB blockers comprise: losartan, candesartan, valsartan, irbesartan, telmisartan, eprosartan, olmesartan, azilsartan, fimasartan, the like, or combinations thereof.

In another embodiment, beta blockers comprise: propranolol, bucindolol, carteolol, carvedilol, labetalol, nadolol, oxprenolol, penbutolol, pindolol, sotalol, timolol, acebutolol, atenolol, betaxolol, bisoprolol, celiprolol, metopolol, nebivolol, esmolol, butaxamine, ICI-118,551, SR 59230A, nebivolol, the like, or combinations thereof.

In another embodiment, calcium channel blockers comprise: amlodipine, aranidipine, azelnidipine, barnidipine, benidipine, cilnidipine, clevidipine, efonidipine, felodipine, isradipine, lacidipine, lercanidipine, manidipine, nicardipine, nifedipine, nilvadipine, nimodipine, nisoldipine, nitrendipine, pranidinpine, fendiline, gallopamil, verapamil, diltiazem, mibefradil, bepridil, flunarizine, fluspirilene, fendiline, gabapentinoids, ziconotide, the like, or combinations thereof.

In another embodiment, cholesterol-lowering drugs comprise: atorvastatin, fluvastatin, lovastatin, pitavastatin, pravastatin, rosuvastatin, simvastatin, the like, or combinations thereof.

In another embodiment, diuretics comprise: acidifying salts, arginine vasopressin receptor 2 antagonists, aquaretics, Na—H exchanger antagonists, carbonic anhydrase inhibitors, loop diuretics, osmotic diuretics, potassium-sparing diuretics, thiazides, xanthines, the like, or combinations thereof.

In another embodiment, vasodilators comprise: hyperpolarization-mediated, cAMP-mediated, cGMP-mediated, the like, or combinations thereof.

It is noted that a number of compositional excipients are disclosed above with specific reference to particular types of formulations. However, it is noted that any excipients disclosed herein, or other suitable excipients, can be used with any type of therapeutic composition, where suitable, whether or not a particular excipient or type of excipient is specifically described in connection with that type of therapeutic composition. Therefore, the therapeutic compositions described herein can be formulated in a variety of ways for various modes of administration.

The present disclosure also provides methods of manufacturing acellular amniotic fluid. The methods can include harvesting or extracting amniotic fluid from a pregnant female to provide a harvested amniotic fluid. In another embodiment, the harvested amniotic fluid can include a therapeutically effective amount of at least one protein, HA, or both. The therapeutically effective amount can be determined by volume, concentration of at least one protein, concentration of HA, the like, or a combination thereof. For example, in some cases, the volume of the harvested amniotic fluid can be small, but the concentration of the at least one protein and/or HA can remain at a suitable concentration, or vice versa. In either case, the harvested amniotic fluid can still have a therapeutically effective amount of at least one protein, HA, or both.

The amniotic fluid can be harvested in a variety of ways. In another embodiment, harvesting can include performing an abdominal fenistil incision through the abdominal and uterine muscles without cutting into the amnion membrane. In further detail, in some cases, the amnion membrane can also be allowed to herniate out via the incision to allow facile access to the amnion membrane. In another embodiment, this method of harvesting (i.e., not cutting the amnion membrane and/or allowing the amnion membrane to herniate out via the incision) can substantially prevent or minimize the collection of blood. A suction catheter can then be inserted into the amnion membrane, such as by blunt end insertion of the catheter into the amnion membrane, for example. The suction catheter can be fluidly connected to a sterile suction container. The amniotic fluid can be suctioned or aspirated into the sterile suction container. In one specific example, an AF collection system can include a sterile suction container, sterile tubing, and a soft wall suction catheter that allows aspiration of the AF from the birth sac through the sterile tubing into the sterile suction container.

In another embodiment, the harvested amniotic fluid can be centrifuged to form a supernatant and a cell pellet. Centrifugation can typically be performed at a relative centrifugal force of from about 1000×g to about 1800×g. In some additional examples, centrifugation can be performed at a relative centrifugal force of from about 1200×g to about 1600×g. However, the particular relative centrifugal force employed can also affect the centrifugation time. Centrifugation can typically be performed for a period of from about 5 minutes to about 60 minutes. In yet other examples, centrifugation can be performed for a period of from about 10 minutes to about 30 minutes. Further, centrifugation can typically be performed at a temperature of from about 1° C. to about 10° C., or from about 2° C. to about 6° C.

A portion of the supernatant can be filtered to prepare a therapeutic composition that is substantially free of cells harvested with or from the amniotic fluid. Filtration can be performed in any suitable manner. In some specific examples, filtration can be performed by passing the supernatant through a first filter to prepare a filtered supernatant and subsequently passing the filtered supernatant through a second filter to prepare the therapeutic composition. Where this is the case, in some examples, the first and second filters can be loaded into a common housing. In yet other examples, the first filter and second filter can be loaded into independent housings that are fluidly connected.

In another embodiment, the harvested amniotic fluid can be filtered to produce a supernatant. Filtration can typically be performed by first using filters from about 40 to 70 μm and then a second filter from about 0.1 μm to 0.2 μm. Filtration can typically be performed at a temperature from about 1° C. to about 25° C. A variety of filter chemistries can be used, and any suitable filter chemistry is considered within the scope of the present method. In another embodiment, the filter chemistry of the first filter, the second filter, or both can include polyethersulfone, cellulose acetate, cellulose nitrate, nylon, glass fiber, or the like.

In another embodiment, the therapeutic composition can include at least 60%, 70%, 80% or 90% of the total protein present in the harvested amniotic fluid. In some additional examples, the therapeutic composition can include from about 70% to about 90% of the total protein present in the harvested amniotic fluid. In yet further examples, the therapeutic composition can include from about 80% to about 95% of the total protein present in the harvested amniotic fluid.

In some additional examples, the therapeutic composition can include at least 80%, 90%, or 95% of the HA present in the harvested amniotic fluid. In some additional examples, the therapeutic composition can include from about 80% to about 95%, 98%, or 99% of the HA present in the harvested amniotic fluid. In yet further examples, the therapeutic composition can include from about 90% to about 100% of the HA present in the harvested amniotic fluid.

In some further examples, the method of manufacturing the acellular amniotic fluid can also include lyophilizing the therapeutic composition. Any suitable lyophilization process can be used to lyophilize the therapeutic composition. In another embodiment, lyophilizing the AF or the therapeutic composition can be performed in multiple segments. For example, a first segment can be performed at a temperature ramp of from about 0.2° C./min to about 1° C./min (e.g., 0.5° C./min, for example) to a holding temperature of about −35° C. to about −45° C. (e.g., −40° C., for example) where the temperature can be maintained for a period of from about 2 hours to about 5 hours (e.g., a 3 hour period, for example). In additional examples, a second segment can be performed at a temperature ramp of from about 1° C./min to about 3° C./min (e.g., about 1.5° C./min) to a holding temperature of from about −10° C. to about −30° C. (e.g., about −20° C., for example) where the temperature can be maintained for a period of from about 5 hours to about 15 hours (e.g., about 10 hours, for example). In yet further examples, a third segment can be performed at a temperature ramp of from about 1° C./min to about 3° C./min (e.g., about 1.5° C./min, for example) to a holding temperature of from about 0° C. to about 10° C. (e.g., 5° C., for example) and maintained for a period of from about 5 hours to about 15 hours (e.g., about 8 hours, for example). In another embodiment, the dry weight can be from about 4 wt % to about 9 wt % of the original weight the AF or therapeutic composition.

The present disclosure also provides methods of treating a subject with an adverse health condition responsive to treatment with acellular amniotic fluid agent. The method can include administering a therapeutically effective amount of acellular amniotic fluid as described herein to a subject.

The acAF described herein can be used to treat a variety of adverse health conditions. Non-limiting examples can include a wound, a respiratory condition, an inflammatory condition, chronic pain, a urological condition, a skeletal condition, an ophthalmic condition, a cardiovascular condition, a neurological condition, a digestive condition, a reproductive condition, a cosmetic condition, the like, or combinations thereof.

In another embodiment, the acAF can be used to treat a wound, or a symptom thereof. Non-limiting types of wounds that can be treated include abrasions, lacerations, contusions, penetrating wounds (e.g., cuts, surgical wounds, puncture wounds, etc.), thermal wounds, chemical wounds, electrical wounds, bite wounds, sting wounds, chronic wounds including wounds after skin grafts failures and post-surgical complications, the like, or combinations thereof. Further, the method can be used to treat external wounds, internal wounds, or both.

In another embodiment, the acAF can be used to treat a respiratory condition, or a symptom thereof. Non-limiting examples of respiratory conditions can include asthma, emphysema, chronic obstructive pulmonary disease, acute viral or bacterial respiratory pneumonia or disease, sinusitis, bronchitis, cystic fibrosis, tuberculosis, tonsillitis, otitis media, pharyngitis, laryngitis, pneumonia, lymphoma, pleural mesothelioma, lung cancers, pulmonary edema, acute respiratory disease syndrome, pneumoconiosis, the like, or combinations thereof.

In another embodiment, the acAF can be used to treat an inflammatory condition, or a symptom thereof. Non-limiting examples of inflammatory or autoimmune conditions can include ankylosing spondylitis, antiphospholipid antibody syndrome, gout, rheumatoid arthritis, myositis, scleroderma, Sjogren's syndrome, lupus, vasculitis, the like, or a combination thereof.

In another embodiment, the acAF can be used to treat chronic pain or the symptom of pain. Non-limiting sources of chronic pain can include chronic inflammation, chronic infection, post-surgical pain, post-transplantation pain (GVHD), post-trauma pain, lower back pain, cancer, arthritis, neurogenic pain, migraines, and other headaches, the like, or combinations thereof.

In another embodiment, the acAF can be used to treat a urological condition, or a symptom thereof. Non-limiting examples of urological conditions can include urinary incontinence, scrotum inflammation, erectile dysfunction, Peyronie's disease, benign prostatic hyperplasia, urinary tract infections, prostate cancer, bladder cancer, bladder prolapse, interstitial cystitis, prostatitis, post-surgical complications, the like, or combinations thereof.

In another embodiment, the acAF can be used to treat a skeletal condition, or a symptom thereof. Non-limiting examples of a skeletal condition can include a fracture, kyphosis, lordosis, scoliosis, arthritis, rheumatoid arthritis, bone cancer, gout, osteoporosis, rickets, the like, or combinations thereof. The method can also be used to facilitate new bone growth and/or in connection with implantation of bone grafts. In some specific examples, a therapeutic composition can be injected or implanted into fractured vertebrae to provide re-expansion of the vertebra, support of the vertebra, and/or facilitate new bone growth to help restore structure and function to the vertebra, and/or other affected bones.

In another embodiment, the acAF can be used to treat an ophthalmic condition, or a symptom thereof. Non-limiting examples of ophthalmic conditions can include basal cell carcinoma, central retinal artery occlusion, central retinal vein occlusion, vitreous detachment, retinal break, retinal detachment, age-related macular degeneration, swollen optic disc, glaucoma, choroidal melanoma, iris melanoma, ischemic optic neuropathy, retinoblastoma, retinopathy of prematurity, strabismus, amblyopia, optic neuritis, refractive disorders, cataracts, graft versus host disease that can occur after certain stem cell or bone marrow transplants, the like, or combinations thereof.

In another embodiment, the acAF can be used to treat a cardiovascular condition, or a symptom thereof. Non-limiting examples can include aneurysm, atherosclerosis, high blood pressure, peripheral arterial disease, angina, coronary artery disease, coronary heart disease, heart attack, heart failure with diverse underlying etiologies (including non-ischemic heart diseases: metabolic, idiopathic, congenital etiologies), stroke, transient ischemic attacks, pericardial disease, heart valve disease, congenital heart disease, cardiomyopathy, pericardial disease, aorta disease, Marfan syndrome, vascular disease, rheumatic heart disease, the like, or combinations thereof.

In another embodiment, the acAF can be used to treat an ischemic injury or a symptom thereof. Non-limiting examples can include cardiac ischemia, bowel ischemia, brain ischemia, limb ischemia, cutaneous ischemia, the like, or combinations thereof. In some example, the acAF can be used to treat an ischemic injury or a symptom thereof including an ischemic injury situs in an organ selected from: a heart, a brain, a limb, a large intestine, a small intestine, a stomach, a liver, a gallbladder, a pancreas, a lung, a kidney, a lymph node, a thymus, a spleen, a skeletal muscle, a smooth muscle, a cardiac muscle, an artery, a vein, or combinations thereof. This includes the donor organ preservation in organ transplantation.

In another embodiment, ischemic injury can be caused by one or more of: embolism, thrombosis of an atherosclerotic artery, trauma, aneurysm, myocardial infarction, mitral valve disease, chronic atrial fibrillation, cardiomyopathies, prosthesis, thoracic outlet syndrome, atherosclerosis, hypoglycemia, tachycardia, radiotherapy, hypotension, a tumor, sickle cell disease, induced g-forces, localized extreme cold, tourniquet application, increased glutamate receptor stimulation, peripheral artery occlusive disease, rupture of blood vessels, anemia, discontinuation of anticoagulant, unconsciousness, or combinations thereof.

In another embodiment, the acAF can be used to treat a neurological condition, or a symptom thereof. Non-limiting examples of neurological conditions can include Parkinson's disease, Alzheimer's disease, spina bifida, stroke, injuries to the spinal cord, injuries to the brain, brain tumors, meningitis, the like, or combinations.

In another embodiment, the acAF can be used to treat a digestive condition, or a symptom thereof. Non-limiting examples of a digestive condition can include acid reflux, surgical or non-surgical abdominal adhesions, appendicitis, Barrett's esophagus, celiac disease, colon polyps, Crohn's disease, diverticulosis, diverticulitis, diabetes, gall stones, gastritis, gastroparesis, gastrointestinal bleeding, hemorrhoids, inguinal hernia, irritable bowel syndrome, lactose intolerance, liver disease, Menetrier's disease, microscopic colitis, pancreatitis, ulcers, proctitis, ulcerative colitis, viral gastroenteritis, whipple disease, the like, or combinations thereof.

In another embodiment, the acAF can be used to treat a reproductive disorder, or a symptom thereof. Non-limiting examples of reproductive disorders can include cervical cancer, prostate cancer, breast cancer, ovarian cancer, penile cancer, vaginal cancer, uterine cancer, testicular cancer, impotence, sexual arousal disorder, hypogonadism, dysmenorrhea, chlamydia, gonorrhea, endometriosis, syphilis, chronic infections and inflammatory diseases, fertility, the like, or combinations thereof.

In another embodiment, the acAF can be used to treat a cosmetic condition. Non-limiting examples of cosmetic conditions can include skin wrinkles, skin laxity, crow's feet, scarring (including surgical and non-surgical scarring), hair loss (including eyelashes and eyebrows), hyperpigmentation, acne, rosacea, dark circles or darkened skin beneath the eye, sun spots, birth marks, varicose veins, spider veins, stretch marks, ingrown hairs, moles, cleft palate and other birth defects, the like, or combinations thereof.

The therapeutically effective amount can depend on a variety of factors, such as the condition to be treated, the subject to be treated, dosage regimens, or the like. For example, in some cases, the therapeutically effective amount can be administered via a single dose and/or a dosage regimen. In another embodiment, the dosage regimen can include administering the therapeutic composition at a suitable frequency. In another embodiment, the dosage regimen can include administering the therapeutic composition from 1 time per day to 12 times per day or more in individual doses. In some further examples, the dosage regimen can include administering the therapeutic composition from 1 time per day to 2, 3, 4, or 6 times per day in individual doses. In yet other examples, the therapeutic composition can be administered via injection, infusion, inhalation, or other equivalent process. In some embodiments, the dosage regimen can be administered topical, local, systemic (subcutaneous, intramuscular, intravenous, or more), or a combination thereof. Where this is the case, in some examples, the composition can be administered over a period of from about 30 minutes or 1 hour to about 6 hours or 12 hours or more. Further, depending on the adverse health condition, administration of the therapeutic composition can be performed over a period of from 1 day to 365 days or more, over a period from 1 day to 30 days, over a period of 7 days to 90 days, over a period of 1 month to 6 months, 12 months, 18 months, or 24 months, or other suitable treatment period at any suitable frequency, such as those described above, or other suitable frequency, such as once per week, twice per week, three times per week, once every two weeks, once per month, once every six weeks, once every two months, etc.

In some specific examples, a therapeutically effective amount can include an amount of total protein from about 0.1 mg to about 2500 mg per dose. In another embodiment, a therapeutically effective amount can include an amount of total protein from about 0.5 mg to about 10 mg, from about 5 mg to about 50 mg, or from about 10 mg to about 100 mg per dose. In yet other examples, the therapeutically effective amount can include an amount of total protein from about 50 mg to about 500 mg, from about 100 mg to about 1000 mg, or from about 750 mg to about 2500 mg per dose.

In some additional examples, a therapeutically effective amount can include an amount of HA from about 0.01 μg to about 350 μg per dose. In another embodiment, a therapeutically effective amount can include an amount of total protein from about 0.05 μg to about 1 μg, from about 0.5 μg to about 5 µg, or from about 1 µg to about 10 µg per dose. In yet other examples, the therapeutically effective amount can include an amount of total protein from about 5 µg to about 50 µg, from about 10 µg to about 100 µg, or from about 75 µg to about 350 µg per dose. In some additional examples, a therapeutically effective amount can include an amount of epidermal growth factor (EGF) from about 0.01 µg to about 200 µg per dose. In another embodiment, a therapeutically effective amount can include an amount of total protein from about 0.01 µg to about 0.5 µg, from about 0.1 µg to about 2 µg, or from about 0.5 µg to about 5 µg per dose. In yet other examples, the therapeutically effective amount can include an amount of total protein from about 1 µg to about 20 µg, from about 10 µg to about 100 µg, or from about 50 µg to about 200 µg per dose.

In another embodiment, the therapeutically effective amount can include a volume therapeutic composition of from about 0.1 mL to about 1000 mL dose. In yet other examples, the therapeutically effective amount can include a volume from about 0.25 mL to about 5 mL, from about 0.5 mL to about 10 mL, or from about 1 mL to about 50 mL dose. In yet other examples, the therapeutically effective amount can include a volume from about 20 mL to about 500 mL, from about 250 mL to about 750 mL, or from about 500 mL to about 1000 mL per dose.

In another embodiment, the therapeutically effective amount can include a volume therapeutic composition of from about 25 µL to about 25 mL. In yet other examples, the therapeutically effective amount can include a volume therapeutic composition of from about 5 µL to about 10 µL, from about 10 µL to about 15 µL, from about 15 µL to about 20 µL, from about 20 µL to about 25 µL, from about 25 µL to about 50 µL, from about 50 µL to about 100 µL, or from about 100 µL to about 250 µL.

It will be apparent to one of ordinary skill in the relevant art that suitable modifications and adaptations to the compositions, formulations, methods, processes, apparata, assemblies, and applications described herein can be made without departing from the scope of any embodiments or aspects thereof. The compositions, apparata, assemblies, and methods provided are exemplary and are not intended to limit the scope of any of the disclosed embodiments. All the various embodiments, aspects, and options disclosed herein can be combined in any variations or iterations. The scope of the compositions, formulations, methods, apparata, assemblies, and processes described herein include all actual or potential combinations of embodiments, aspects, options, examples, and preferences described herein. The compositions, formulations, apparata, assemblies, or methods described herein may omit any component or step, substitute any component or step disclosed herein, or include any component or step disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. All patents and publications cited herein are incorporated by reference herein for the specific teachings thereof.

Various embodiments and aspects of the inventions described herein are summarized by the following clauses:

Clause 1. A method of treating an ischemic injury in a subject, comprising:

administering a therapeutically effective amount of an acellular amniotic fluid (acAF) to an ischemic injury situs within a therapeutic time window.

Clause 2. The method of clause 1, wherein the acAF is substantially free of cells and debris.

Clause 3. The method of clause 1 or 2, wherein the ischemic injury situs is an organ selected from: a heart, a brain, a limb, a large intestine, a small intestine, a stomach, a liver, a gallbladder, a pancreas, a lung, a kidney, a lymph node, a thymus, a spleen, a skeletal muscle, a smooth muscle, a cardiac muscle, an artery, a vein, or combinations thereof.

Clause 4. The method of any one of clauses 1-3, wherein the ischemic injury is ischemia/reperfusion or permanent ligation.

Clause 5. The method of any one of clauses 1-4, wherein the therapeutic time window includes one or more of: 30 minutes, 60 minutes, one day, 1 week, 2 weeks, or 4 weeks.

Clause 6. The method of any one of clauses 1-5, wherein administration is performed via one or more of: an intravenous injection, or an injection proximate to the ischemic injury situs.

Clause 7. The method of any one of clauses 1-6, wherein the therapeutically effective amount of acAF has less than or equal to 10,000 particles per milliliter of particles having a particle size of 10 microns or greater.

Clause 8. The method of any one of clauses 1-7, wherein the therapeutically effective amount of acAF has less than or equal to 300 particles per milliliter of particles having a particle size of 25 microns or greater.

Clause 9. The method of any one of clauses 1-8, wherein the therapeutically effective amount of acAF has an optical density of less than 0.20 when exposed to electromagnetic radiation at a wavelength of 590 nm.

Clause 10. The method of any one of clauses 1-9, wherein the therapeutically effective amount of acAF further comprises hemoglobin in an amount from 1 µg/mL to 60 µg/mL.

Clause 11. The method of any one of clauses 1-10, wherein the therapeutically effective amount of acAF further comprises an active agent.

Clause 12. The method of any one of clauses 1-11, wherein the active agent is an anti-infective agent, an antibiotic, an anti-tumor agent, an anti-inflammatory agent, a pain-controlling agent, an anti-rheumatic agent, a bisphosphonate, a supplementary growth factor, a supplementary cytokine, an amino acid, a protein, a vaccine, a hormone, a vitamin, a phytoestrogen, a fluoride, or combinations thereof.

Clause 13. The method of any one of clauses 1-12, wherein the active agent is: angiotensin-converting enzyme (ACE) inhibitors, aldosterone inhibitors, angiotensin II receptor blockers (ARBs), beta-blockers, calcium channel blockers, cholesterol-lowering drugs, digoxin, diuretics, potassium, magnesium, proprotein convertase subtilisin kexin type 9 (PCSK9) inhibitors, vasodilators, warfarin, or combinations thereof.

Clause 14. The method of any one of clauses 1-13, wherein the active agent further comprises stem cells.

Clause 15. The method of any one of clauses 1-14, wherein the therapeutically effective amount of acAF further comprises a pharmaceutically acceptable carrier.

Clause 16. The method of any one of clauses 1-15, wherein the therapeutically effective amount includes a volume of therapeutic composition of from about 0.1 mL to about 1000 mL.

Clause 17. The method of any one of clauses 1-16, wherein the therapeutically effective amount includes an amount of total protein from about 0.1 mg to about 2500 mg.

Clause 18. The method of any one of clauses 1-17, wherein the therapeutically effective amount includes an amount of hyaluronic acid (HA) from about 0.1 mg to about 2500 mg.

Clause 19. A method of treating a cardiac ischemic event in a subject, comprising: administering a therapeutically effective amount of acellular amniotic fluid (acAF) to an ischemic situs of a heart of the subject within a therapeutic time window.

Clause 20. The method of clause 19, wherein the therapeutic time window includes one or more of: 30 minutes, 60 minutes, one day, 1 week, 2 weeks, or 4 weeks.

Clause 21. The method of clause 19 or 20, wherein administration is performed via one or more of: direct administration into a myocardium of the heart of the subject via an epicardial injection or an endocardial injection; intravenous injection to the subject; intracoronary administration; or direct administration to a coronary vein of the heart of the subject via a local injection.

Clause 22. The method of any one of clauses 19-21, wherein administration is performed concomitantly with a procedure directed to the heart of the subject, wherein the procedure includes one or more of: cardiac catheterization, coronary angioplasty, balloon angioplasty, coronary artery stent, atherectomy, laser angioplasty, coronary artery bypass surgery, intra-aortic balloon pump surgery, ventricular assist device (VAD) surgery, heart transplant surgery, valvuloplasty, valve repair surgery, valve replacement surgery, or combinations thereof.

Clause 23. The method of any one of clauses 19-22, wherein the therapeutically effective amount of acAF has less than or equal to 10,000 particles per milliliter of particles having a particle size of 10 microns or greater.

Clause 24. The method of any one of clauses 19-23, wherein the therapeutically effective amount of acAF has less than or equal to 300 particles per milliliter of particles having a particle size of 25 microns or greater.

Clause 25. The method of any one of clauses 19-24, wherein the therapeutically effective amount of acAF has an optical density of less than 0.20 when exposed to electromagnetic radiation at a wavelength of 590 nm.

Clause 26. The method of any one of clauses 19-25, wherein the therapeutically effective amount of acAF further comprises a pharmaceutically acceptable carrier.

Clause 27. The method of any one of clauses 19-26, wherein the therapeutically effective amount includes a volume of therapeutic composition of from about 25 μL to about 25 mL.

Clause 28. The method of any one of clauses 19-27, wherein the therapeutically effective amount of acAF further comprises an active agent selected from: angiotensin-converting enzyme (ACE) inhibitors, aldosterone inhibitors, angiotensin II receptor blockers (ARBs), beta-blockers, calcium channel blockers, cholesterol-lowering drugs, digoxin, diuretics, potassium, magnesium, proprotein convertase subtilisin kexin type 9 (PCSK9) inhibitors, vasodilators, warfarin, or combinations thereof.

Clause 29. A system of treating an ischemic injury of a subject, comprising:

a therapeutic composition, comprising:

a therapeutically effective amount of acellular amniotic fluid (acAF);

an administration device configured to administer the acAF to the subject.

Clause 30. The system of clause 29, wherein the administration device comprises one or more of: an infusion pump, a hypodermic needle, a drip chamber, a peripheral cannula, a pressure bag, an auto-injector, or a syringe.

Clause 31. The system of clause 29 or 30, wherein the composition has less than or equal to 10,000 particles per milliliter of particles having a particle size of 10 microns or greater.

Clause 32. The system of any one of clauses 29-31, wherein the composition has less than or equal to 300 particles per milliliter of particles having a particle size of 25 microns or greater.

Clause 33. The system of any one of clauses 29-32, wherein the composition has an optical density of less than 0.20 when exposed to electromagnetic radiation at a wavelength of 590 nm.

Clause 34. The system of any one of clauses 29-33, wherein the composition further comprises hemoglobin in an amount from 1 μg/mL to 60 μg/mL.

Clause 35. The system of any one of clauses 29-34, wherein the composition further comprises an active agent.

Clause 36. The system of clause 35, wherein the active agent is an anti-infective agent, an antibiotic, an anti-tumor agent, an anti-inflammatory agent, a pain-controlling agent, an anti-rheumatic agent, a bisphosphonate, a supplementary growth factor, a supplementary cytokine, an amino acid, a protein, a vaccine, a hormone, a vitamin, a phytoestrogen, a fluoride, or combinations thereof.

Clause 37. The system of clause 35 or 36, wherein the active agent further comprises stem cells.

Clause 38. The system of any one of clauses 29-37, wherein the composition further comprises a pharmaceutically acceptable carrier.

Clause 39. The system of any one of clauses 29-38, wherein the composition includes a volume of therapeutic composition of from about 0.1 mL to about 1000 mL.

Clause 40. The system of any one of clauses 29-39, wherein the composition includes an amount of total protein from about 0.1 mg to about 2500 mg.

Clause 41. The system of any one of clauses 29-40, wherein the composition includes an amount of hyaluronic acid (HA) from about 0.1 mg to about 2500 mg.

Clause 42. A method of treating fibrosis in a subject, comprising:

administering a therapeutically effective amount of acellular amniotic fluid (acAF) to an ischemic situs of the subject within a therapeutic time window.

Clause 43. A method of treating peripheral arterial disease (PAD) in a subject, comprising: administering a therapeutically effective amount of acellular amniotic fluid (acAF) to an ischemic situs of a lower extremity of the subject within a therapeutic time window.

Clause 44. A method of treating cyanosis in a subject, comprising:

administering a therapeutically effective amount of acellular amniotic fluid (acAF) to an ischemic situs of an extremity of the subject, wherein the therapeutically effective amount is administered via a dosage regimen.

EXAMPLES

Example 1

Schematic Diagram of Intramyocardial Injections of Human Amniotic Fluid (h-acAF) in the Ischemia/Reperfusion (I/R) Injury Model in Rat.

Figure 1B:
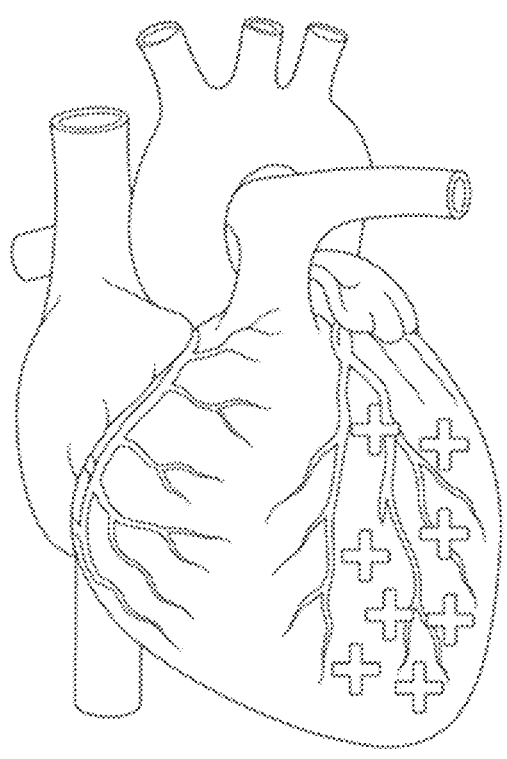
FIG. 1B illustrates the potential locations of intramyocardial injections and the total injection volume in the I/R injury model.
Figure 1C:
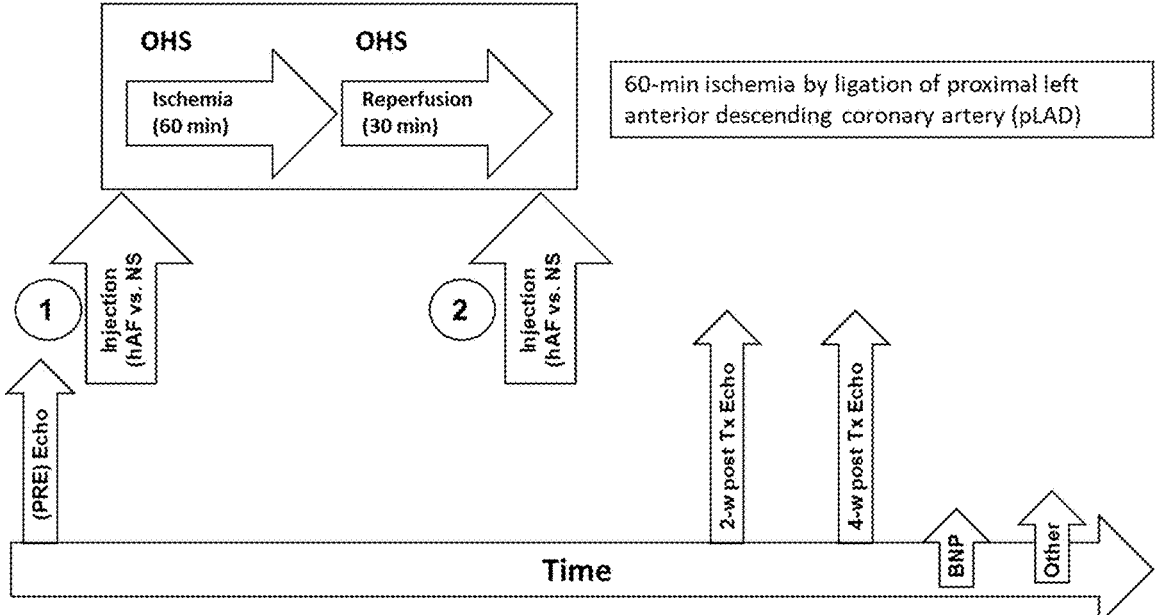
FIG. 1C shows a schematic diagram of intramyocardial injections of human acellular amniotic fluid (h-acAF) in the ischemia/reperfusion (I/R) injury model to investigate therapeutic time window.
Figure 1D:
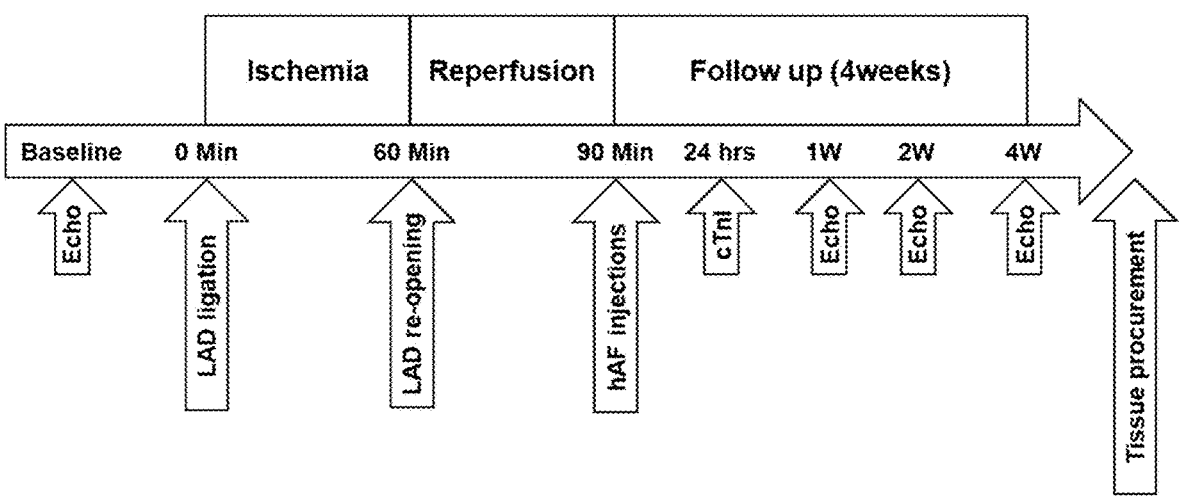
FIG. 1D shows a schematic diagram of intramyocardial injections of h-acAF at 30-minutes post-reperfusion followed by 60-minutes of ischemia (i.e., 90 min post-ischemia) in the I/R injury model.

As illustrated in FIG. 1C, the ischemia/reperfusion (I/R) injury model in rats included: (a) an echocardiogram of each subject's heart prior to a first group of injections, (b) a first group of injections including human amniotic fluid (h-acAF) or a normal saline (N/S), (c) open heart surgery to model ischemic heart failure for a period of about 60 minutes; (d) open heart surgery to allow reperfusion for a period of about 30 minutes, (e) a second group of injections including h-acAF or N/S, (f) an echocardiogram of each subject's heart 2 weeks after open heart surgery, (g) an echocardiogram of each subject's heart 4 weeks after open heart surgery, (h) a B-type natriuretic peptide (BNP) test, or (i) pathological or molecular studies. As illustrated in FIG. 1B, the total injection volume included 8 injections of 25 μL each for a total amount of 200 μL. As illustrated in FIG. 1A, the in vivo model of heart failure (HF) in animal can be constructed by inducing ischemic injury or non-ischemic injury. In ischemic injury model, permanent ligation of the proximal left anterior descending (LAD) coronary artery of a subject or ischemia/reperfusion injury by 30-60-minute temporary occlusion (ligation) of the LAD coronary artery of the subject modeled ischemic HF (iHF). A chemotherapeutics-induced subject was used to model non-ischemic heart failure.

Example 2

Intramyocardial Injection of h-acAF Enhances Systolic Function, Reverses Ischemic LV Remodeling, and Reveals a Wide Therapeutic Window in the Ischemic Heart Failure Model.

Ischemia-reperfusion injury model was performed by a temporary 60 min ligation of proximal left anterior descending coronary artery in SD rats. Baseline LV functions were evaluated by echocardiography and then, randomized to receive intramyocardial injections (total volume 200 μL) of either N/S or h-acAF immediately before 60-minute ischemia injury (0 min) and after 30 min reperfusion followed by 60-minute ischemia (90 min). The functional and geometric parameters were evaluated over 4 weeks. EF (%) in LV is one of standard measurements of global heart function and predicts prognosis of adverse cardiovascular events and mortality.

Figure 2A:
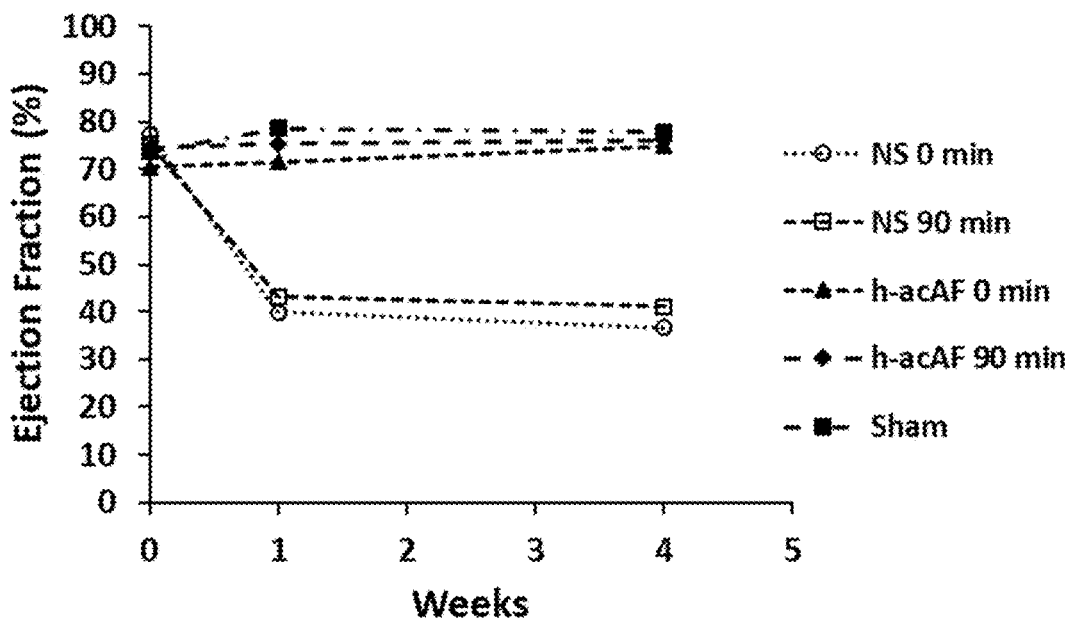
FIG. 2A shows a graph illustrating that intramyocardial injections of h-acAF immediately before 60-minute ligation (0 min) can enhance systolic function as measured by ejection fraction percentage at two time periods from the baseline: 2 weeks after treatment (injections); and 4 weeks after treatment (injections).
Figure 2B:
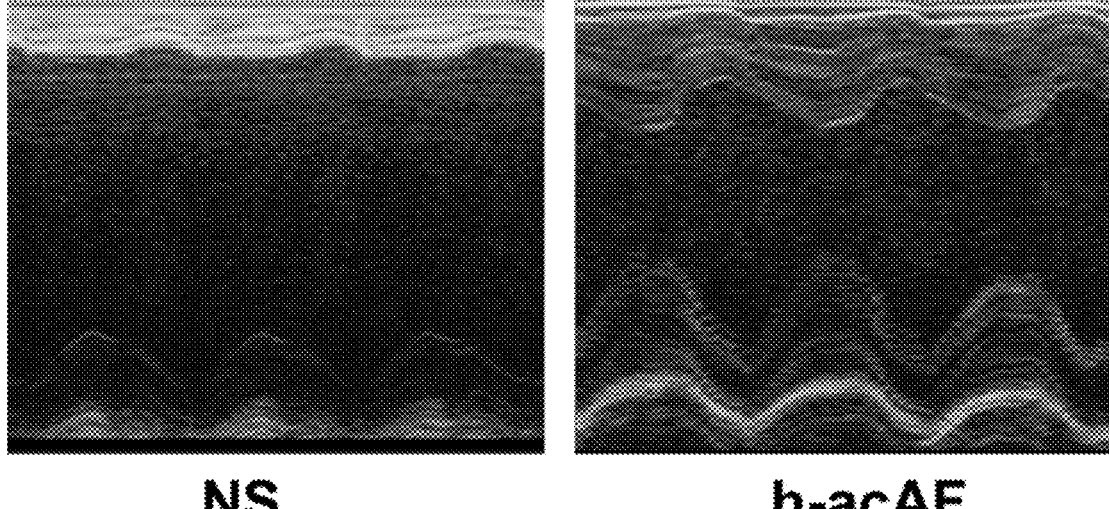
FIG. 2B shows photomicrographs illustrating that functional assessment of h-acAF administration at 30-minutes post-reperfusion after 60 minutes of proximal LAD coronary artery ligation (90 min) using transthoracic M-mode echocardiogram at mid-papillary level.
Figure 2C:
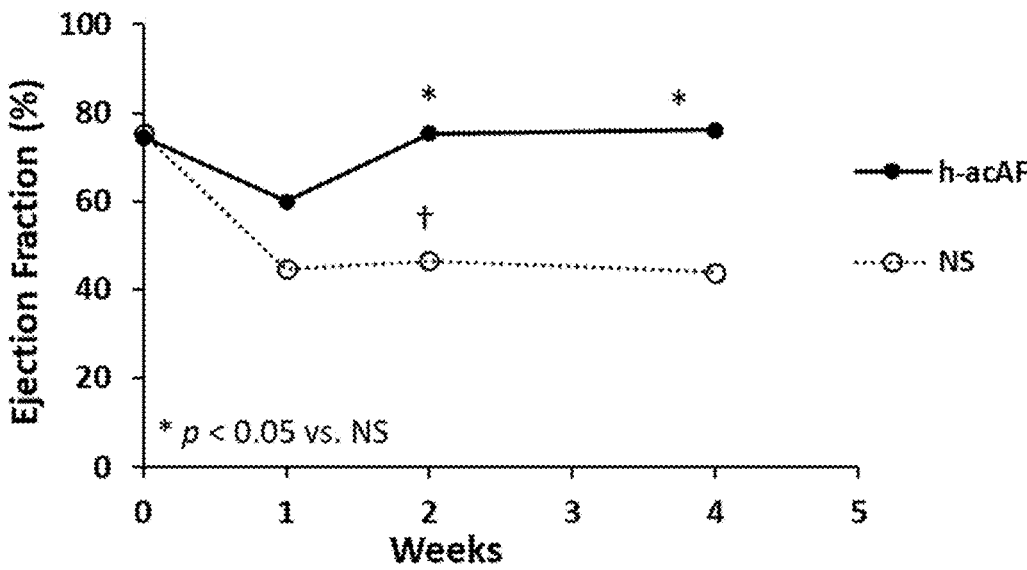
FIG. 2C shows a graph illustrating that intra-myocardial injections of h-acAF at 30 minutes post-reperfusion followed by 60 minute ischemia (90 min) can enhance systolic function as measured by ejection fraction (EF) percentage at three time periods from the baseline: 1 week after treatment (injections); 2 weeks after treatment (injections); and 4 weeks after treatment (injections).
Figure 2D:
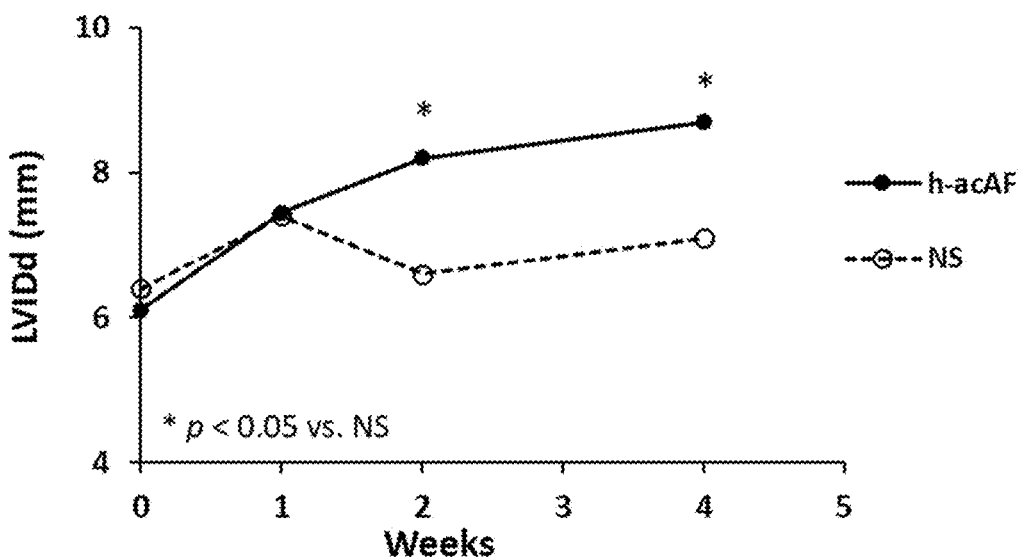
FIG. 2D shows a graph illustrating that geometric functional assessment of h-acAF administration (at 90 min), after sixty minutes of LAD coronary artery ligation, followed by 30 minutes of reperfusion (I/R) measuring left ventricular end diastolic diameter (LVIDd) in rats treated with h-acAF and normal saline (NS) at 1, 2, and 4 weeks after I/R (P<0.05, *vs NS treated).

As illustrated in FIGS. 2A and 2C, intramyocardial injections of the h-acAF groups immediately before 60-minute ischemia injury (0 min) and after 30 min reperfusion followed by 60-minute ischemia (90 min) revealed a wide therapeutic window in the ischemic heart failure model.

Systolic function in LV was determined by measuring the ejection fraction as a percentage at two time periods from the baseline: (a) 2 weeks after treatment (injections) (2W); and (b) 4 weeks after treatment (injections) (4W).

As illustrated in FIG. 2A, the ejection fraction was measured at two time periods (2W and 4W) for: a group administered h-acAF immediately before the start of 60-minute ischemia injury (i.e., h-AF 0 min); a group administered h-acAF after 30 minute reperfusion followed by 60-minute ischemia (i.e., h-AF 90 min); a group administered N/S immediately before the start of 60-minute ischemia injury (i.e., N/S 0 min); a group administered N/S after 30 minute reperfusion followed by 60-minute ischemia (i.e., N/S 90 min); and a sham group. The N/S (90 min) group is provided as a comparison. For the h-AF 0 min group, the ejection fraction was about stable compared to baseline between 2W and 4W. For the N/S 0 min group, the ejection fraction declined compared to baseline between the 2W and 4W time periods. As illustrated in FIG. 2C, the ejection fraction was measured at three time periods (1W, 2W and 4W) for: a group administered h-acAF at 30-minute reperfusion followed by 60-minute ischemia (i.e., h-AF 90 min); a group administered N/S at 30-minute reperfusion followed by 60-minute ischemia (i.e., N/S 90 min); and a sham group. The sham group underwent surgical procedures similar to the h-AF 90 min group and the N/S 90 min group but with a loose stitch around the coronary arteries. The sham group did not undergo a 60-minute ligation of the pLAD (proximal left anterior descending) coronary artery before release. For the h-AF 90 min group and the sham 90 min group, the ejection fraction was about stable from the baseline between 2W and 4W. For the N/S 90 min group, the ejection fraction declined from the baseline between: the 2W and 4W time periods.

Contrary to the time-dependent aggravation of LV systolic function in N/S 90 min group, the intramyocardial injections of h-acAF after 30 minute reperfusion followed by 60-minute ischemia (i.e., h-AF 90 min) group showed the favorable recovery of LV function and geometry at 1, 2, and 4 wks post-I/R injury, up to the level of sham group as well as baseline pre-treatment level. Here, both functional and geometric improvements ascertain the regenerative capacity of h-acAF and imply the induction of reverse post-ischemic remodeling of h-acAF treatment in ischemic HF rats. The LV end-diastolic diameter (LVIDd) was relatively well preserved than LV end-systolic diameter (LVIDs). Intramyocardial injections of h-acAF at 30-minute post-reperfusion after 60-minute ischemia (i.e., h-AF 90 min) imply that h-acAF provides cardioprotective effects with practical feasibility and easy accessibility in clinic, which can be applied during PCI (percutaneous coronary intervention) as well as clinical and surgical I/R injury settings.

The h-acAF 0-min group included 9 subjects. The h-acAF 90-min group included 9 subjects. The N/S 0-min group and the N/S 90-min group included 8 subjects. The data was determined from the means±S.E.M. with *P<0.05 vs the N/S group.

Example 3

In Ischemic Heart Failure, Intramyocardial Injections of h-acAF Recovers Favorable Cardiac Geometry, Irrespective of Injection Time of h-acAF Application (with a Wide Range of Cardioprotective Feasibility of h-acAF).

Figures 3A, 3B:
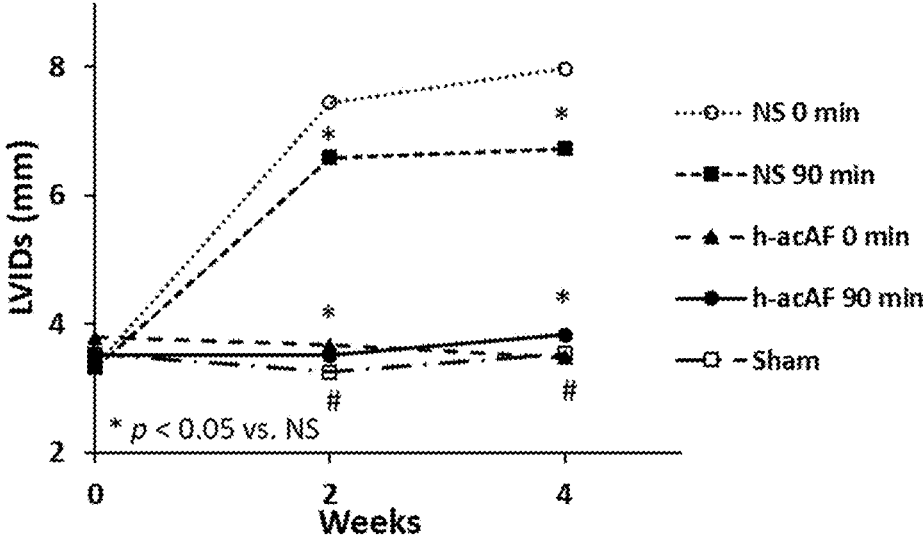
FIG. 3A shows a graph illustrating that injections of h-acAF can recover favorable cardiac geometry, with different injection times of h-acAF (both 0 min and 90 min) in I/R injury, as measured by left ventricular internal diameter in diastole (LVIDd) at two time periods from the baseline: 2 weeks after treatment (injections); and 4 weeks after treatment (injections).
FIG. 3B shows a graph illustrating that injections of h-acAF can recover favorable cardiac geometry, with different injection times of h-acAF (both 0 min and 90 min) in I/R injury, as measured by left ventricular internal diameter in systole (LVIDs) at two time periods from the baseline: 2 weeks after treatment (injections); and 4 weeks after treatment (injections).

As illustrated in FIGS. 3A and 3B, intramyocardial injections of the h-acAF group with different injection time points recovered favorable cardiac geometry in the ischemic heart failure model of I/R injury. Cardiac geometry was determined by measuring the left ventricular internal diameter in diastole (LVIDd) and the left ventricular internal diameter in systole (LVIDs) at two time periods: (a) 2 weeks after treatment (injections) (2W); and (b) 4 weeks after treatment (injections) (4W).

As illustrated in FIG. 3A, the LVIDd was measured at two time periods (2W and 4W) for: a group administered h-acAF immediately before the start of 60-minute ischemia injury (i.e., h-AF 0 min); a group administered h-acAF after 30 minute reperfusion followed by 60-minute ischemia (i.e., h-AF 90 min); a group administered N/S immediately before the start of 60-minute ischemia injury (i.e., N/S 0 min); a group administered after 30 minute reperfusion followed by 60-minute ischemia (i.e., N/S 90 min); and a sham group. The sham group underwent surgical procedures similar to the h-AF 90 min group and the N/S 90 min group but with a loose stitch around the coronary arteries. The sham group did not undergo a 60-minute ligation of the pLAD (proximal left anterior descending) coronary artery before release. For the h-AF 0 min group and the h-AF 90 min group, the LVIDd was about stable from the baseline between 2W and 4W. For the N/S 0 min group and the N/S 90 min group, the LVIDd increased from the baseline between the 2W and 4W time periods.

As illustrated in FIG. 3B, the LVIDs was measured at two time periods (2W and 4W) for: a group administered h-acAF immediately before the start of 60-minute ischemia injury (i.e., h-AF 0 min); a group administered h-acAF after 30 minute reperfusion followed by 60-minute ischemia (i.e., h-AF 90 min); a group administered N/S immediately before the start of 60-minute ischemia injury (i.e., N/S 0 min); a group administered N/S after 30 minute reperfusion followed by 60-minute ischemia (i.e., N/S 90 min); and a sham group. The sham group underwent surgical procedures similar to the h-AF 90 min group and the N/S 90 min group but with a loose stitch around the coronary arteries. The sham group did not undergo a 60-minute ligation of the pLAD (proximal left anterior descending) coronary artery before release. For the h-AF 0 min group and the h-AF 90 min group, the LVIDs was about stable from the baseline between 2W and 4W. For the N/S 0 min group and the N/S 90 min group, the LVIDs increased from the baseline between the 2W and 4W time periods.

The h-acAF 0-min group and the h-acAF 90-min group each included 9 subjects. The N/S 0-min group and the N/S 90-min group each included 8 subjects. The data was determined from the means±S.E.M. with *P<0.05 vs the N/S 90 min group and #P<0.05 vs the N/S 0 min group.

Example 4

Independent of Different Donor's Origins, the Application of h-acAF Demonstrated Consistent Cardio-Protective Effects on Ischemic Heart Failure. Allogenic h-acAFs from Different Donors Exhibit Similar Functional Improvements.

Like blood banks, h-acAF banking with an allogenic donor source will be an ideal resource for the clinic. Compared with autologous transplant or chemical synthesis, it will be important to prove assurance of availability, feasibility, and consistent therapeutic effect of allogenic h-acAFs collected from different donors. h-acAFs from 3 different donors (#2~#4) were randomly selected with diverse clinical demographics (Table 1). Intramyocardial injections of 200 μL of h-acAF harvested from 3 different donors, immediately before the start of 60-minute ischemia injury (i.e., h-AF 0 min) and after 30 minutes reperfusion followed by 60-minute ischemia (i.e., h-AF 90 min) demonstrated similar overlapping functional and geometric improvements in LV EF %, LVIDd, and LVIDs at 2 and 4 weeks after I/R injury and injections than a group administered N/S immediately before the start of 60-minute ischemia injury (i.e., N/S 0 min) and a group administered N/S after 30 minute reperfusion followed by 60-minute ischemia (i.e., N/S 90 min).

TABLE 1

| Allogenic h-acAF Donors | | | | |
|---|---|---|---|---|
| Lot No. | Donor Age | Race | Gestation Age | Gravida |
| AF2017 | 33 | Caucasian | 39 weeks | 6 |
| AF2017 | 37 | Caucasian | 39 weeks | 4 |
| AF2018 | 30 | Caucasian | 38 weeks | 5 |
| AF2019 | 20 | Caucasian | 40 weeks | 1 |

As illustrated in FIGS. 4A-4F, the application of h-acAF collected from different donors demonstrated consistent cardio-protective effects on ischemic heart failure. Systolic function was determined by measuring the ejection fraction as a percentage (%) at two time periods from the baseline: (a) 2 weeks after treatment (injections) (2W); and (b) 4 weeks after treatment (injections) (4W). Cardiac geometry was determined by measuring the left ventricular internal diameter in diastole (LVIDd) and the left ventricular internal diameter in systole (LVIDs) at two time periods from the baseline: (a) 2 weeks after treatment (injections) (2W); and (b) 4 weeks after treatment (injections) (4W).

Figure 4A:
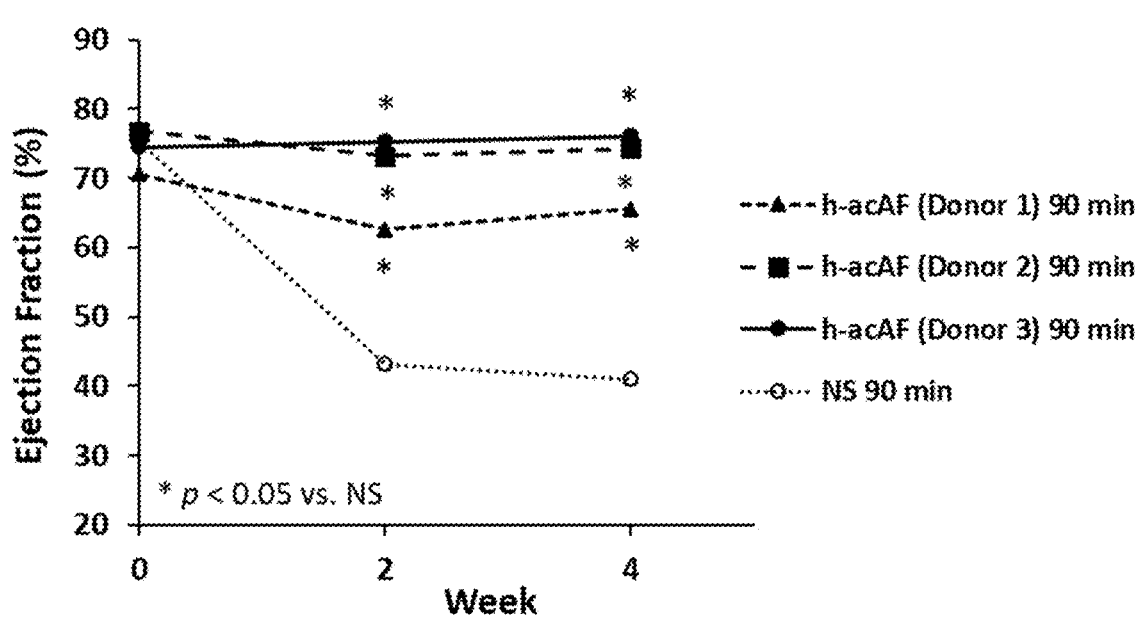
FIG. 4A-B show graphs illustrating that application of h-acAF from 3 different human (allogenic) donors immediately before 60 minute ischemic injury (0 min) can have consistent cardio-protective effects on ischemic heart failure as measured by ejection fraction percentage (%) at two time periods from the baseline: 2 weeks after treatment (injections); and 4 weeks after treatment (injections).

As illustrated in FIG. 4A, the ejection fraction was measured at two time periods (2W and 4W) for: three different donor groups administered h-acAF after 30 minute reperfusion followed by 60-minute ischemia (i.e., h-AF 90 min: h-AF from donor #1, h-AF from donor #2, h-AF from donor #3); and a group administered N/S after 30 minute reperfusion followed by 60-minute ischemia (i.e., N/S 90 min). For the three different donor groups administered h-acAF after 30 minute reperfusion followed by 60-minute ischemia (i.e., h-AF 90 min: h-AF from donor #1, h-AF from donor #2, h-AF from donor #3), the ejection fraction was about stable from baseline between 2W and 4W. For the N/S 90 min group, the ejection fraction declined from baseline between the 2W and 4W time periods.

Figure 4B:
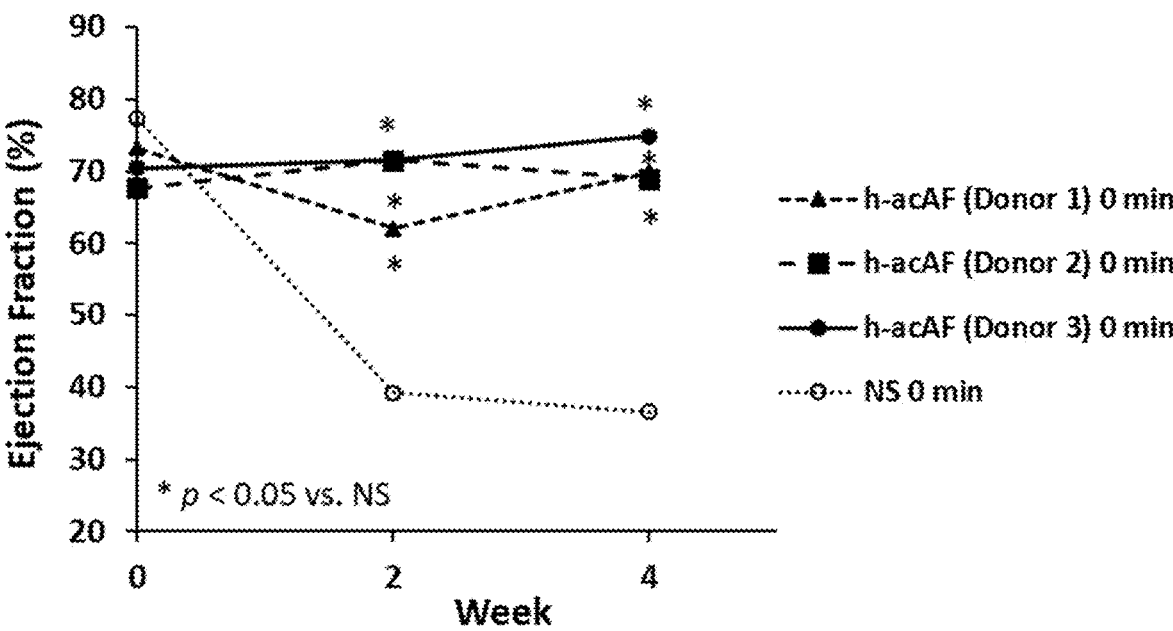

As illustrated in FIG. 4B, the ejection fraction was measured at two time periods (2W and 4W) for: three different donor groups administered h-acAF immediately before the start of 60-minute ischemia injury (i.e., h-AF 0 min: h-AF from donor #1, h-AF from donor #2, h-AF from donor #3); and a group administered N/S immediately before the start of 60-minute ischemia injury (i.e., N/S 0 min). For the three different donor groups administered h-acAF immediately before the start of 60-minute ischemia injury (i.e., h-AF 0 min: h-AF from donor #1, h-AF from donor #2, h-AF from donor #3), the ejection fraction was about stable from baseline between 2W and 4W. For the N/S 0 min group, the ejection fraction declined from baseline between the 2W and 4W time periods.

Figure 4C:
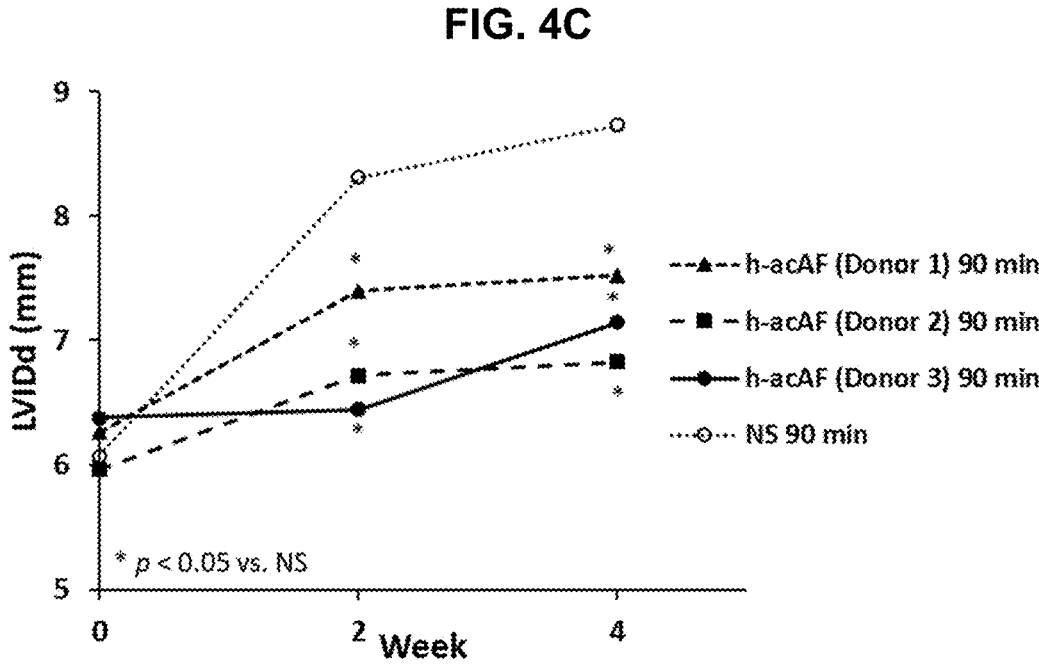
FIG. 4C-D shows graphs illustrating that application of h-acAF from 3 different human (allogenic) donors immediately before 60 minute ischemic injury (0 min) can have consistent cardio-protective effects on ischemic heart failure as measured by left ventricular internal diameter in diastole (LVIDd) at two time periods from the baseline: 2 weeks after treatment (injections); and 4 weeks after treatment (injections).

As illustrated in FIG. 4C, the LVIDd was measured at two time periods (2W and 4W) for: three different donor groups administered h-acAF after 30 minute reperfusion followed by 60-minute ischemia injury (i.e., h-AF 90 min: h-AF from donor #1, h-AF from donor #2, h-AF from donor #3); and a group administered N/S after 30 minute reperfusion followed by 60-minute ischemia (i.e., N/S 90 min). For the three different donor groups administered h-acAF after 30 minute reperfusion followed by 60-minute ischemia injury (i.e., h-AF 90 min: h-AF from donor #1, h-AF from donor #2, h-AF from donor #3), the LVIDd was about stable from baseline between 2W and 4W. For the N/S 90 min group, the LVIDd increased from baseline between the 2W and 4W time periods.

Figure 4D:
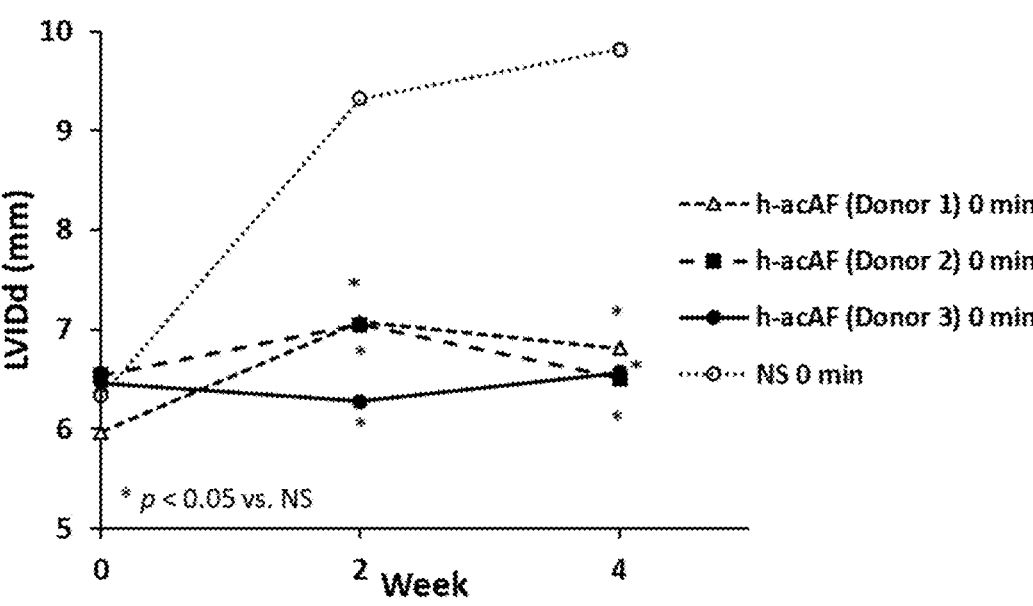

As illustrated in FIG. 4D, the LVIDd was measured at two time periods (2W and 4W) for: three different donor groups administered h-acAF immediately before the start of 60-minute ischemia injury (i.e., h-AF 0 min: h-AF from donor #1, h-AF from donor #2, h-AF from donor #3); and a group administered N/S before the start of 60-minute ischemia injury (i.e., N/S 0 min). For the three different donor groups administered h-acAF immediately before the start of 60-minute ischemia injury (i.e., h-AF 0 min: h-AF from donor #1, h-AF from donor #2, h-AF from donor #3), the LVIDd was about stable from baseline between 2W and 4W. For the N/S 0 min group, the LVIDd increased from baseline between the 2W and 4W time periods.

Figure 4E:
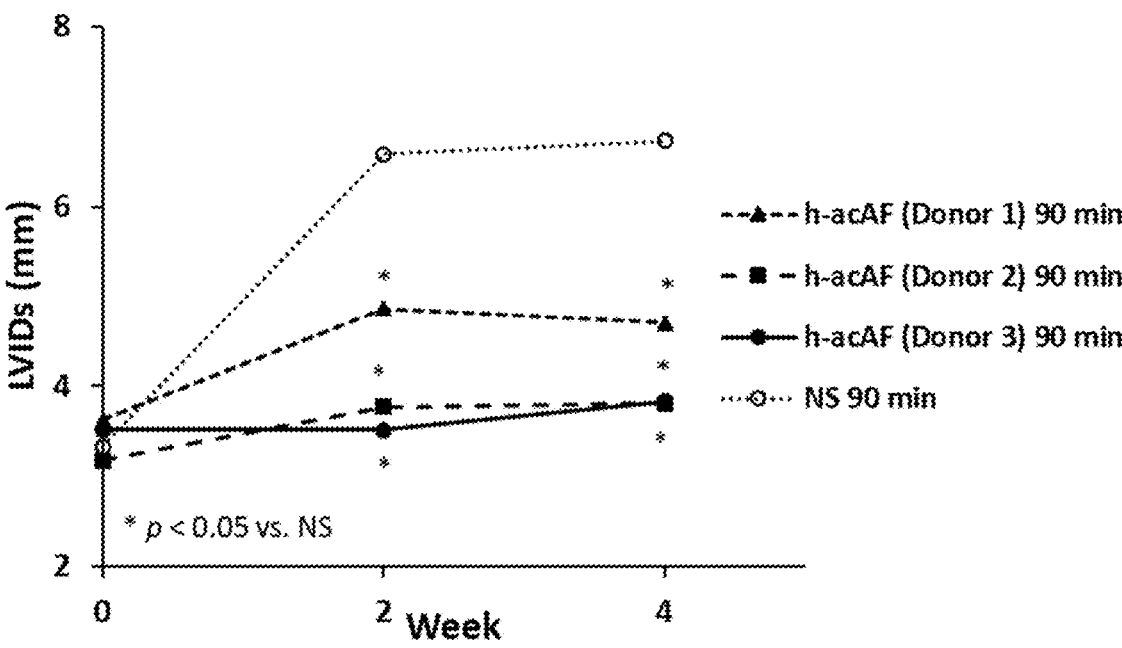
FIG. 4E-F show graphs illustrating that application of h-acAF from 3 different human (allogenic) donors immediately before 60 minute ischemic injury (0 min) can have consistent cardio-protective effects on ischemic heart failure as measured by left ventricular internal diameter in systole (LVIDs) at two time periods from the baseline: 2 weeks after treatment (injections); and 4 weeks after treatment (injections).

As illustrated in FIG. 4E, the LVIDs was measured at two time periods (2W and 4W) for: three different donor groups administered h-acAF after 30 minute reperfusion followed by 60-minute ischemia (i.e., h-AF 90 min: h-AF from donor #1, h-AF from donor #2, h-AF from donor #3); and a group administered N/S after 30 minute reperfusion followed by 60-minute ischemia (i.e., N/S 90 min). For the three different donor groups administered h-acAF after 30-minute reperfusion followed by 60-minute ischemia (i.e., h-AF 90 min: h-AF from donor #1, h-AF from donor #2, h-AF from donor #3), the LVIDs was about stable from baseline between 2W and 4W. For the N/S 90 min group, the LVIDd increased from baseline between the 2W and 4W time periods.

Figure 4F:
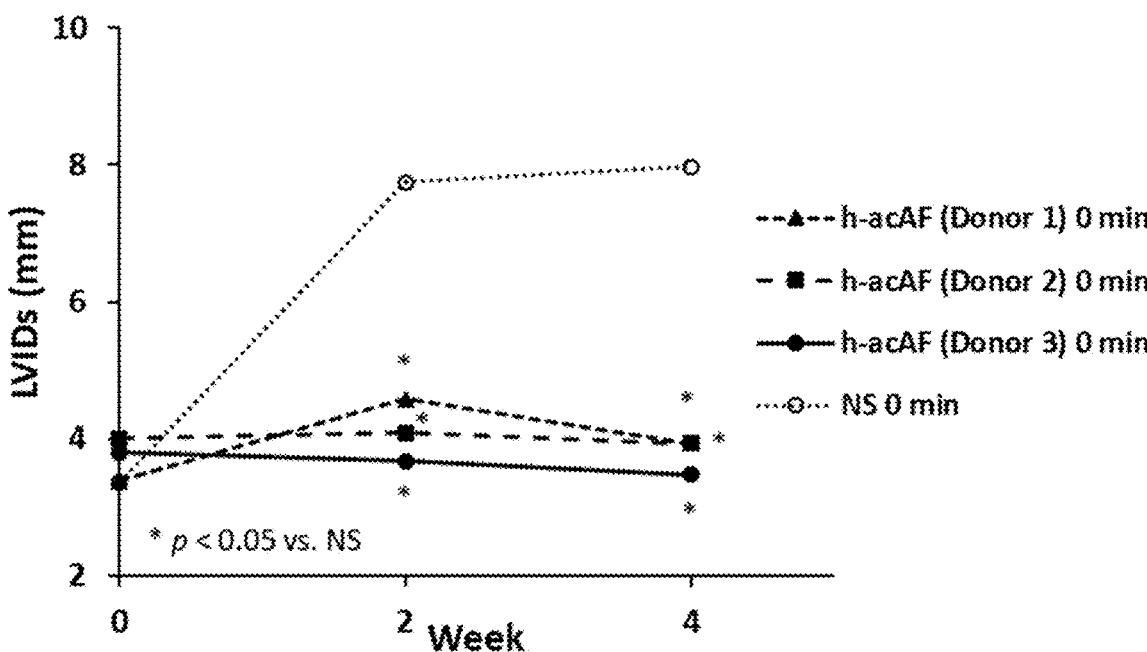

As illustrated in FIG. 4F, the LVIDs was measured at two time periods (2W and 4W) for: three different donor groups administered h-acAF immediately before the start of 60-minute ischemia injury (i.e., h-AF 0 min: h-AF from donor #1, h-AF from donor #2, h-AF from donor #3); and a group administered N/S before the start of 60-minute ischemia injury (i.e., N/S 0 min). For the three different donor groups administered h-acAF immediately before the start of 60-minute ischemia injury (i.e., h-AF 0 min: h-AF from donor #1, h-AF from donor #2, h-AF from donor #3), the LVIDs was about stable from baseline between 2W and 4W. For the N/S 0 min group, the LVIDs increased from baseline between the 2W and 4W time periods.

Each of the h-acAF donor groups (i.e., h-AF from donor #1, h-AF from donor #2, h-AF from donor #3) immediately before 60-minute ischemia injury (i.e., h-AF 0 min) and after 30 min reperfusion followed by 60-minute ischemia (i.e., h-AF 90 min) included 7 subjects. The N/S 0-min group and the N/S 90-min group each included 8 subjects. The data was determined from the means±S.E.M. with *P<0.05 vs the N/S group (N/S 90 min and N/S 0 min).

Example 5

Intramyocardial Delivery of h-acAF Attenuates the Size of Infarct Area and the Level of Myocardium Injury at 24 Hours Post-1/R Injury.

To decipher mechanisms and evaluate treatment strategies of h-acAF, the infarct size in early phase was assessed using TTC stainings at 24 hrs after I/R injury and injections of NS after 30-minute reperfusion followed by 60-minute ligation of pLAD coronary artery (i.e., NS 90 min) and injections of h-acAF after 30-minute reperfusion followed by 60-minute ligation of pLAD coronary artery (i.e., h-AF 90 min). Triphenyltetrazolium-based techniques stain the viable tissue red and can evaluate the infarct size of harvested tissue within a few hours after infarction, compared with conventional histological stains. The h-AF 90 min group demonstrated significantly higher viable tissue with smaller infarct area qualitatively and quantitatively than the NS 90 min group at 24 hrs after I/R injury.

Figures 5A, 5B:
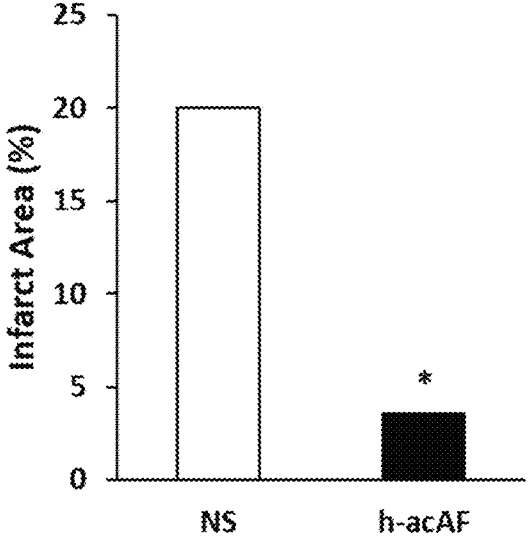
FIG. 5A shows a photo illustrating that administration of h-acAF can attenuate the size of the infarct area and the level of myocardium injury evaluated with mid-papillary cross sections of hearts, harvested at 24 hours post-I/R injury (followed by injections of N/S or h-acAF at 30 minutes post-reperfusion after 60 min ligation of proximal LAD coronary artery) stained with TTC. Infarct area stains white, viable area stains red.
FIG. 5B shows a bar graph illustrating that delivery of h-acAF can attenuate the size of the infarct area and the level of myocardium injury, harvested at 24 hours post-I/R injury with quantification of infarct area by positive pixel count digital analysis (P<0.05, *vs NS treated).
Figure 5C:
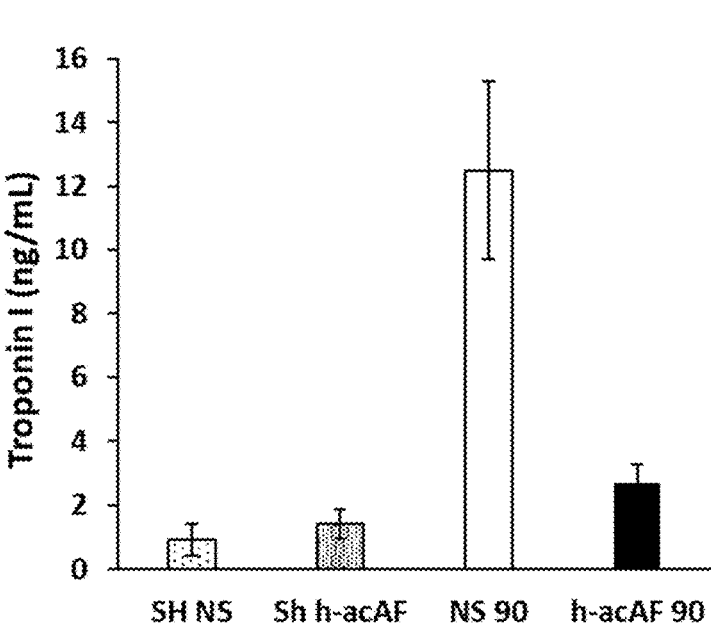
FIG. 5C shows a bar graph illustrating that delivery of h-acAF can attenuate the level of myocardium injury with quantitative measurements of serum troponin I levels, cardiac-specific marker for myocardial infarction or ischemic damage, at 24 hours after I/R (followed by injections of N/S or h-acAF at 30 minutes post-reperfusion after 60 min ligation of proximal LAD coronary artery) (P<0.05, *vs NS treated).

As illustrated in FIGS. 5A-5C, administration of h-acAF at 30 minutes post-reperfusion after 60 minutes ligation of pLAD coronary artery (i.e., h-AF 90 min) attenuates the size of infarct area and the level of myocardium injury at 24 hours post I/R injury in the ischemic heart failure model. Infarct area size and the level of myocardium injury was determined at 24 hours after 60-minute ischemia.

As illustrated in FIG. 5B, the extension of the infarct area was determined qualitatively for: a group administered h-acAF after 30-minute reperfusion followed by 60-minute ischemia (i.e., h-AF 90 min); and a group administered N/S after 30-minute reperfusion followed by 60-minute ischemia (i.e., N/S 90 min). The size of infarct area in h-AF 90 min was significantly smaller than in N/S 90 min.

The level of cardiac troponin (cTn) has been established and used as an indicator of heart damage or heart attack in the clinic. To confirm acute myocardial injury by temporary 60-min ligation of pLAD coronary artery, the levels of cTnI were measured with post-24 hours serums after I/R injury.

Figure 5D:
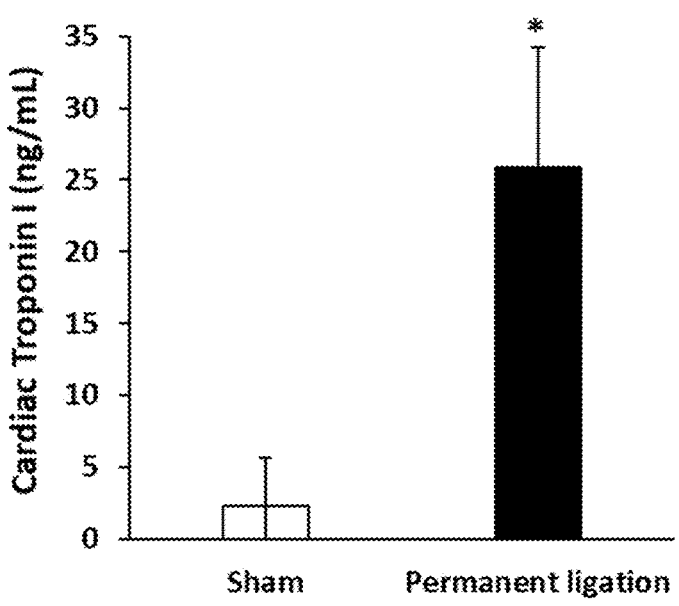
FIG. 5D shows a graph illustrating dual confirmation of the study enrollment in permanent ligation model by measurements of cTn level and decreased systolic function in LV (EF) by echocardiogram.

As illustrated in FIG. 5C-D, cardiac troponin (ng/mL) (cTn) was measured for: a group administered h-acAF after 30-minute reperfusion followed by 60-minute ischemia (i.e., ligation) (i.e., h-AF 90 min); and a sham group. The sham group underwent surgical procedures similar to the h-AF 90 min group but with a loose stitch around the coronary arteries. The sham group did not undergo a 60-minute ligation of the pLAD (proximal left anterior descending) coronary artery before release. Compared with sham groups of NS and h-acAF, a group administered N/S after 30-minutes reperfusion followed by 60-minute ligation of pLAD coronary artery (i.e., N/S 90 min) and a group administered h-acAF after 30-minutes reperfusion followed by 60-minute ligation of pLAD coronary artery (i.e., h-AF 90 min) exhibited higher level of cTnI. The serum level of cardiac-specific Troponin I (cTnI) in permanent ligation group showed significantly higher than the sham group. The rats with a low level of cTnI (cut value) were excluded for following treatment allocation of intramyocardial injections with N/S or h-acAF.

The h-acAF group included 10 subjects. The N/S group included 10 subjects. The data was determined from the means±S.E.M. with *P<0.05 vs the N/S group. The scale bars in FIG. 5A are 5 millimeters (mm).

Example 6

Delivery of h-acAF Rescues the Ischemic Cardiac Fibrosis and Apoptosis and Stimulates Angiogenesis.

Protective effects of h-acAF on myocardial fibrosis and remodeling were assessed. The amount of myocardium lost, fibrosis, is correlated to the severity of HF, arrhythmia, and adverse clinical events after MI as well as survival. At 4 weeks after I/R injury and injections of h-acAF, hearts and lungs were harvested. Whole heart tissue was stained with Masson's trichrome to examine the levels of fibrosis.

Figures 6A, 6B:
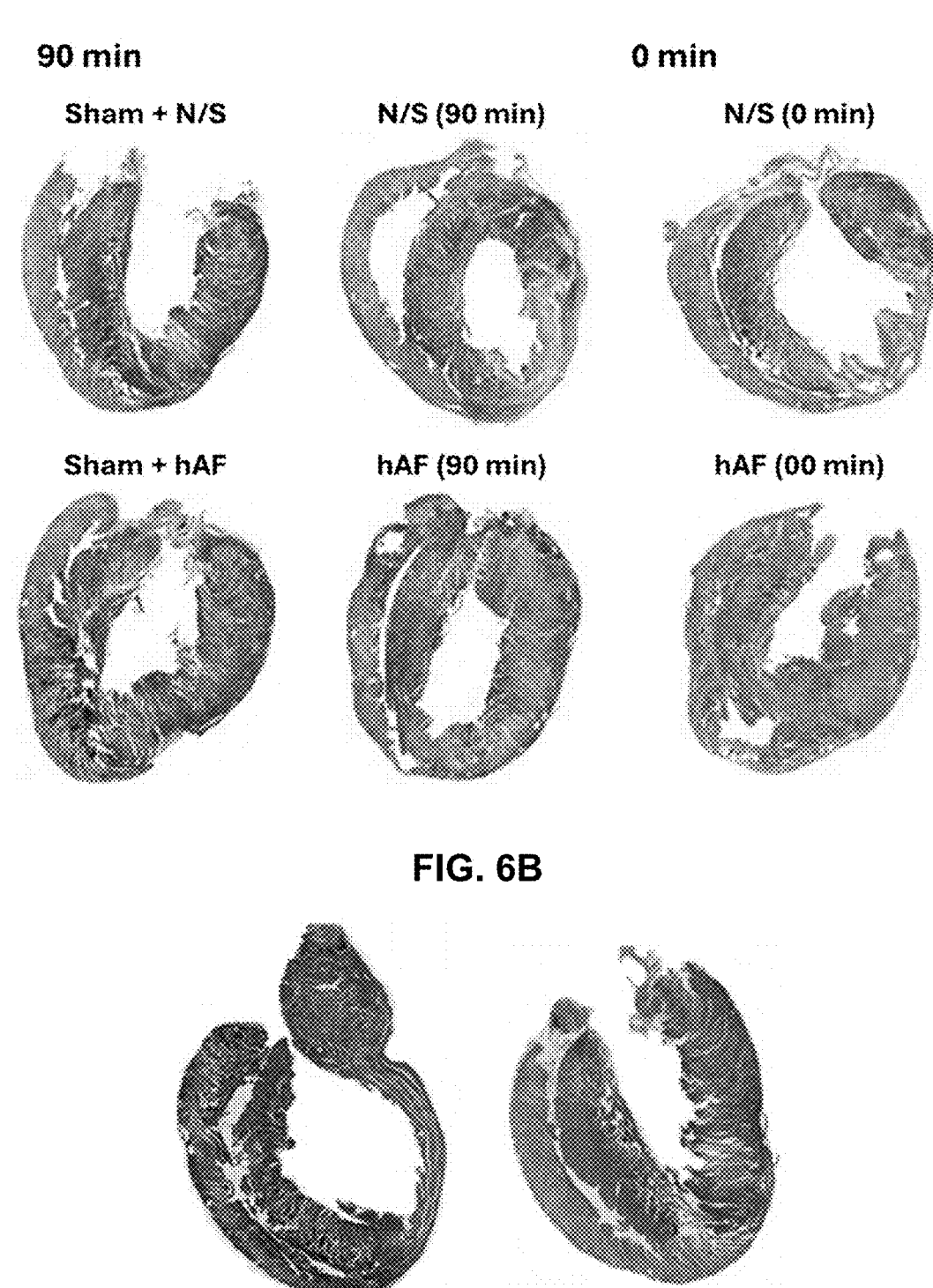
FIG. 6A shows a photo array illustrating that intramyocardial injections of h-acAF can rescue ischemic cardiac fibrosis, both immediately before 60-minute ligation (0 min) and at 30 minutes post-reperfusion followed by 60-minute ischemia (90 min) compared with N/S injection group.
FIG. 6B shows photos illustrating that administration of h-acAF at 30 min post-reperfusion after 60 minutes ischemia (90 min) prevents cardiac fibrosis showing longitudinal cross-sections of rat hearts stained with Masson's trichrome. Fibrosis stains blue, myocardium stains red.

As illustrated in FIG. 6A, intramyocardial injections of h-acAF rescues the ischemic cardiac fibrosis and apoptosis and stimulates angiogenesis in the ischemic heart failure model by I/R injury. Ischemic cardiac fibrosis was determined by Masson's Trichrome staining for: a group administered h-acAF immediately before the start of 60-minute ischemia injury (i.e., h-AF 0 min); a group administered h-acAF after 30 minute reperfusion followed by 60-minute ischemia (i.e., h-AF 90 min); a group administered N/S immediately before the start of 60-minute ischemia injury (i.e., N/S 0 min); a group administered N/S after 30 minute reperfusion followed by 60-minute ischemia (i.e., N/S 90 min); a sham group with N/S; and a sham group with h-acAF. The sham groups underwent surgical procedures similar to the h-AF 90 min group but with a loose stitch around the coronary arteries. The sham group did not undergo a 60-minute ligation of the pLAD (proximal left anterior descending) coronary artery before release. A group administered h-acAF after 30 minute reperfusion followed by 60-minute ischemia (i.e., h-AF 90 min) and a group administered h-acAF immediately before the start of 60-minute ischemia injury (i.e., h-AF 0 min) revealed decreased interstitial fibrosis in the infarcted area and smaller fibrotic area by Masson's trichrome than a group administered N/S after 30 minute reperfusion followed by 60-minute ischemia (i.e., N/S 90 min) and a group administered N/S immediately before the start of 60-minute ischemia injury (i.e., N/S 0 min).

FIG. 6B shows photos illustrating that administration of h-acAF at 30 min post-reperfusion after 60 minutes ischemia (i.e., h-AF 90 min) prevents cardiac fibrosis showing longitudinal cross-sections of rat hearts stained with Masson's trichrome. Fibrosis stains blue, myocardium stains red.

Figures 6C, 6D:
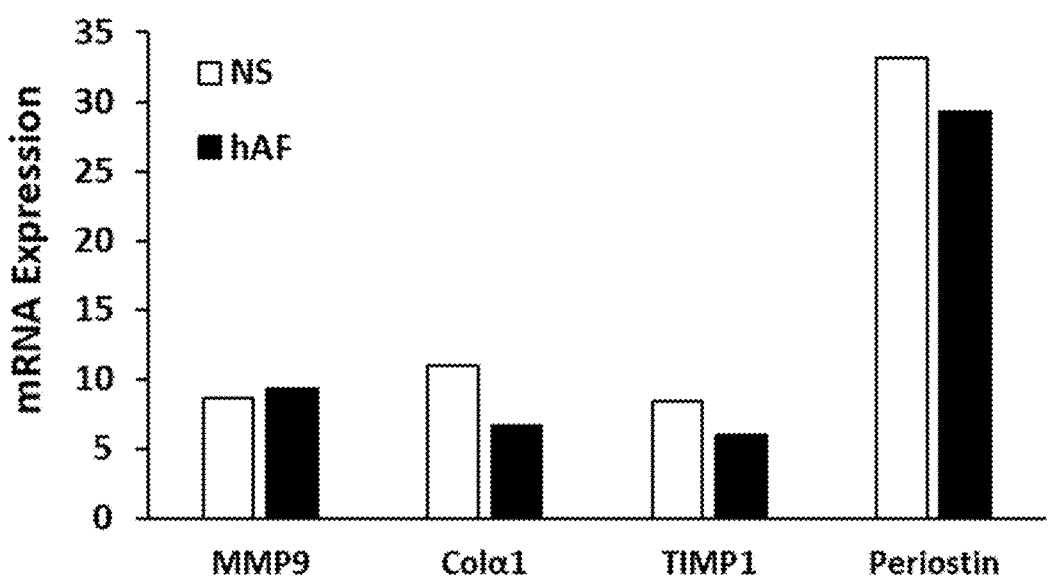
FIG. 6C shows a bar graph illustrating showing administration of h-acAF can rescue ischemic cardiac fibrosis with quantification of tissue fibrosis by positive pixel count digital analysis (P<0.05, *vs NS treated).
FIG. 6D shows a bar graph illustrating effects of h-acAF on fibrosis markers by reverse transcription polymerase chain reaction (RT-PCR) compared with N/S treated group at 30 min post-reperfusion after 60 minutes ischemia (90 min) with heart tissues harvested at 4 weeks post-treatment: matrix metallopeptidase 9 (MMP-9), collagen type I alpha 1 chain (Col1α1), tissue inhibitor of metallopeptidase 1 (TIMP1).

FIG. 6C shows a bar graph illustrating showing administration of h-acAF can rescue ischemic cardiac fibrosis with quantification of tissue fibrosis by positive pixel count digital analysis (P<0.05, *vs NS treated).

FIG. 6D shows a bar graph illustrating effects of h-acAF on fibrosis markers by reverse transcription polymerase chain reaction (RT-PCR) compared with N/S treated group at 30 min post-reperfusion after 60 minutes ischemia (90 min) with heart tissues harvested at 4 weeks post-treatment: matrix metallopeptidase 9 (MMP-9), collagen type I alpha 1 chain (Col1α1), tissue inhibitor of metallopeptidase 1 (TIMP1). There was no significant difference of fibrosis markers in administration of h-acAF at 30 min post-reperfusion after 60 minutes ischemia (i.e., h-AF 90 min) and administration of N/S at 30 min post-reperfusion after 60 minutes ischemia (i.e., N/S 90 min) at 4 weeks after I/R injury and injections. Heart tissues harvested at 4 weeks after treatments (i.e., injections) are too late to elucidate the underlying protective molecular mechanisms of h-AF treatment in I/R injury model.

Example 7

The Preconditioning and the Delayed Post-Conditioning of h-acAF Injections Alleviates the Manifestation of Pulmonary Congestion in Chronic Left Ventricular Failure (Chronic Heart Failure).

Figure 7A:
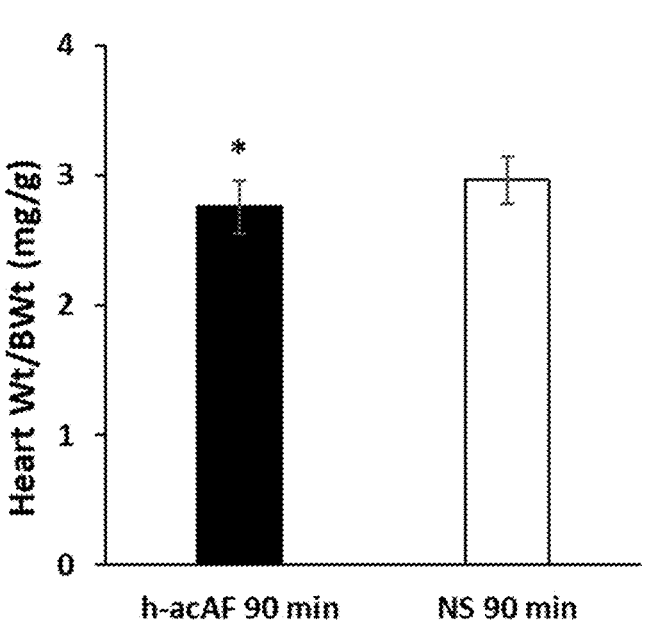
FIG. 7A-7C show bar graphs illustrating that preconditioning and delayed post-conditioning of h-acAF injections can alleviate manifestation of pulmonary congestion in chronic left ventricular failure (chronic heart failure).
Figure 7B:
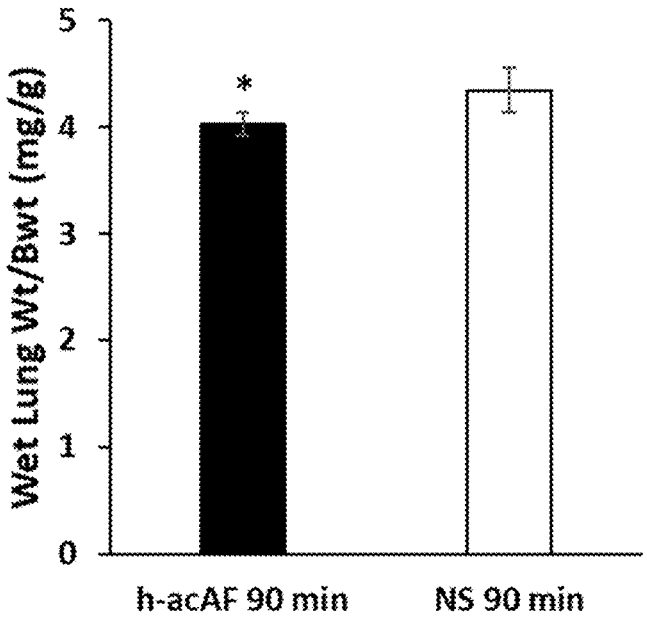
Figure 7C:
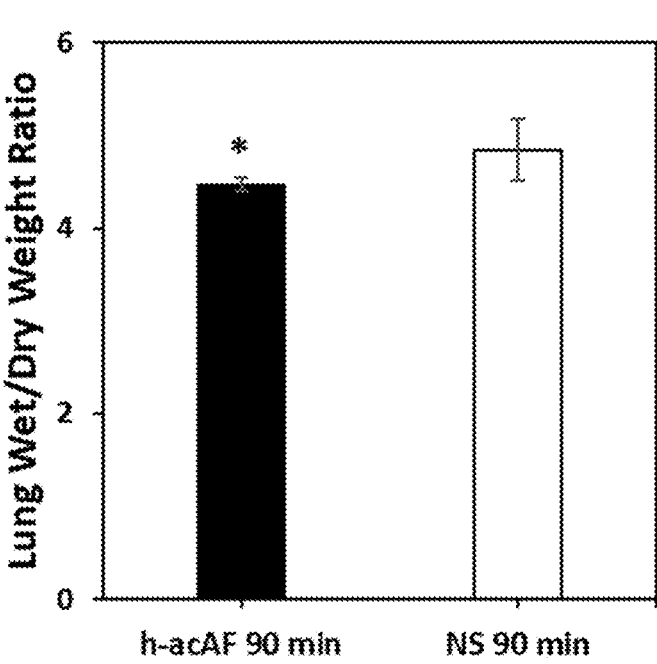

As illustrated in FIG. 7 pre-conditioning and delayed post-conditioning of h-acAF injections alleviates the manifestation of pulmonary congestion in chronic left ventricular failure (chronic heart failure) in the ischemic heart failure model of 60 min I/R injury. The h-acAF group demonstrated the decrease of the ratio of heart weight to bodyweight (Bwt) and the ratio of wet lung weight to dry lung weight than the N/S group both at pre-ischemia of 60-minute I/R injury (0 min) and at 30-minute post-reperfusion followed by 60-minute ischemia (90 min). Treatment of h-acAF significantly prevented the increase in the ratio of the lung wet-to-dry weight in response to I/R injury than the N/S group. The h-acAF90 min group showed alleviated pulmonary congestions in ischemic heart failure measured by wet/dry lung weight and heart/body weight (FIG. 7A-C). The data was determined from the means±S.E.M. with *P<0.05 vs the N/S 90 min group.

Example 8 h-acAFs Collected from Different Donors Contains Comparable Efficacy. The Underlying Mechanism of the Robust Cardioprotective Effects of h-acAF in Ischemia Heart Failure can be Explained Dominantly by Anti-Inflammatory and Immune-Modulatory Pathways.

Characteristics of h-acAF from 17 donors were assessed with quantitative antibody arrays and hierarchical cluster analysis heat map and reported that allogenic h-acAFs collected from different donors had variability in both cytokine levels and composition with similarity in a large majority of the same cytokines. Anti-inflammatory, anti-microbial, and regenerative properties of h-acAF has been studied and discussed since the first report of concentrates of AF inhibit the development of peritonitis. There were concerns about the variation of h-acAF collected from different donors and analyzed 4 different donor samples used in this study using cytokine antibody arrays, Luminex® and heat map analysis.

Cytokine antibody arrays were used to simultaneously identify and quantitate protein levels for 400 human cytokines from the 4 different lots of h-acAF that were used in these studies. This resulted in a number of cytokines being detected out of the 400 cytokines tested or of the cytokines that were tested showed a positive signal in AF. Each protein with a positive signal was assigned a biological function based on annotated information obtained from Entrez Gene, GeneCards, UniProtKB/Swiss-Prot, Gene Wiki, and the Human Protein Reference databases. Cytokines were assigned to 12 different functional categories or were designated as an unknown or miscellaneous protein. Variances in expression levels for proteins present in all 4 collections were identified using the criteria that a 1.5-fold increase or 50.65-fold decrease in signal intensity between protein levels was a measurable and significant difference among analytes. Using these criteria, no measurable differences in expression levels were observed for some of the cytokines.

As illustrated in FIG. 8, the underlying mechanism of the robust cardioprotective effects of h-acAF in ischemia heart failure can be explained by anti-inflammatory and immune-modulatory pathways. Third-Trimester amniotic fluid and cytokine & growth factor profiles are depicted in FIG. 8.

Figure 8A:
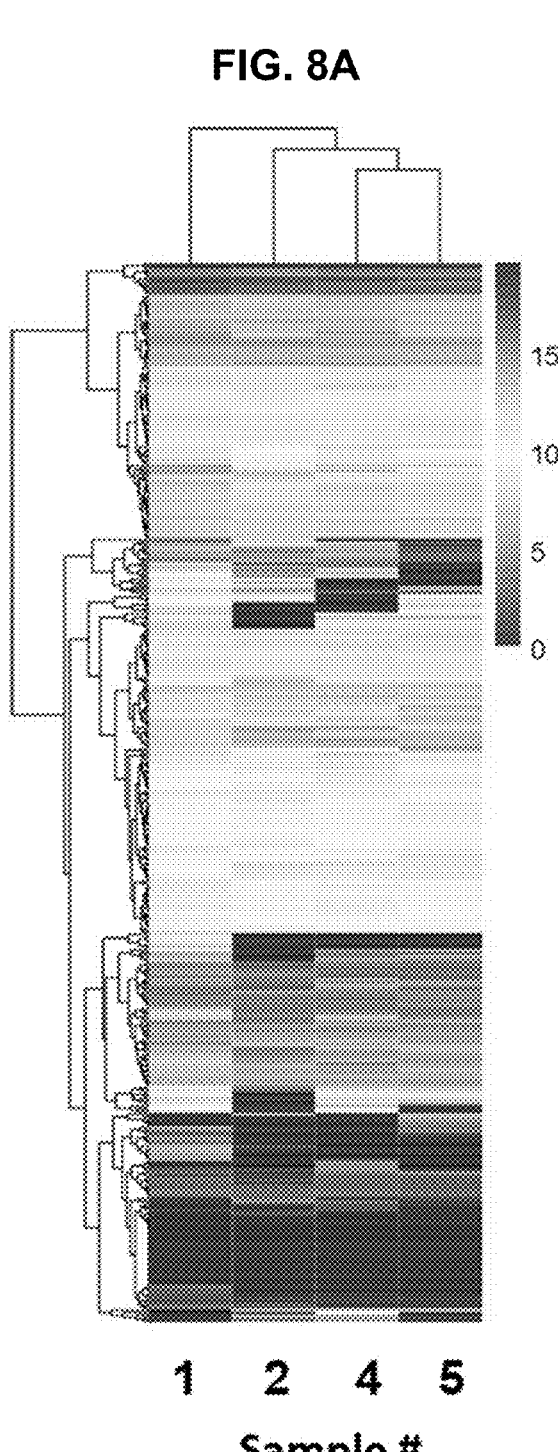
FIG. 8A shows heat map and dendrogram constructed with hierarchical cluster analysis that reveal the expression profile of cytokines present in each of 4 lots of h-acAF from different human allogenic donors (used in FIG. 4 to evaluate efficacies of h-acAF depending on different donors). A Quantibody® Human Cytokine Antibody Array 9000 was used to quantitatively and simultaneously measure the concentration of 400 cytokines present in the 4 lots of h-acAF used in these studies.

FIG. 8A shows heat map and dendrogram constructed with hierarchical cluster analysis that reveal the expression profile of cytokines present in each of 4 lots of h-acAF from different human allogenic donors (used in FIG. 4 to evaluate efficacies of h-acAF depending on different donors). A Quantibody® Human Cytokine Antibody Array 9000 was used to quantitatively and simultaneously measure the concentration of 400 cytokines present in the 4 lots of h-acAF used in these studies. In heat map analysis, h-acAFs revealed similarities among different donors. The filtered allogenic h-acAFs consist of over 400 favorable proteins, such as cytokines and chemokines.

Figure 8B:
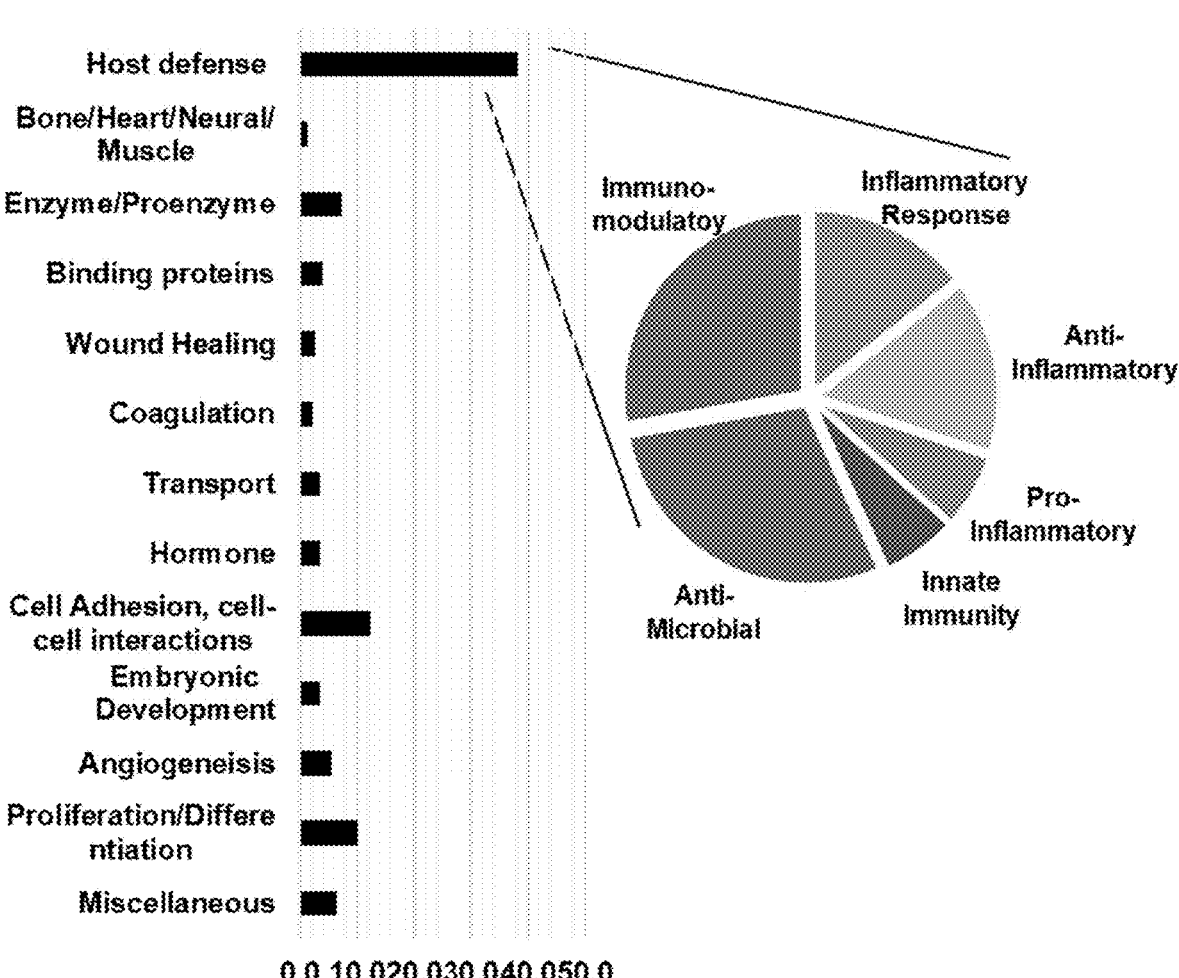
FIG. 8B shows a graph illustrating that based on information queried in multiple databases, cytokines present in each of the 4 lots of h-acAF are assigned to 13 defined biological function groups and a miscellaneous group. The pie graph depicts a further sub-categorization of the host defense cytokines. This sub-categorization illustrates whether the host defense cytokine is involved in the inflammatory response, innate immunity or immunomodulation or acts as an anti-inflammatory, pro-inflammatory, or anti-microbial.

FIG. 8B shows a graph illustrating that based on information queried in multiple databases, cytokines present in each of the 4 lots of h-acAF are assigned to 12 defined biological function groups and a miscellaneous group. In Liminex® analysis, about 40% of the majority of allogenic h-acAFs was composed of host defense properties, such as immunomodulatory, anti-inflammatory, and anti-microbial activity. The pie graph depicts a further sub-categorization of the host defense cytokines. This sub-categorization illustrates whether the host defense cytokine is involved in the inflammatory response, innate immunity or immunomodulation or acts as an anti-inflammatory, pro-inflammatory, or anti-microbial mechanism. The next biggest categories of similar functioning proteins were for proteins involved in cell adhesion, proliferation, and angiogenesis.

Example 9

Intramyocardial h-acAF Administration Augments Immunomodulatory and Anti-Inflammatory Capacity and Leads to Ischemic HF Repair.

One goal was to elucidate and understand the underlying molecular mechanisms of allogenic h-acAFs filled with over 400 favorable proteins on cardiac application. The main underlying mechanisms of h-acAF therapy for ischemic HF application can be condensed into anti-inflammatory and immunomodulatory supports and combinational effects of enormous mixture of favorable hundreds of proteins in allogenic h-acAFs on injured/ischemic myocardium. To determine whether mRNA expression in tissue can help explain the cardio-protective effects of h-acAFs in vivo, mRNA expressions were measured in 1 week and 4 weeks heart tissues. The 4 weeks heart tissues with far manifested (i.e., full-blown) fibrosis were too late to get a clue for this hypothesis between the N/S treated group at 30 min post-reperfusion after 60 minutes ischemia (i.e., N/S 90 min) and the h-acAF treated group at 30 min post-reperfusion after 60 minutes ischemia (i.e., h-AF 90 min).

Figure 9A:
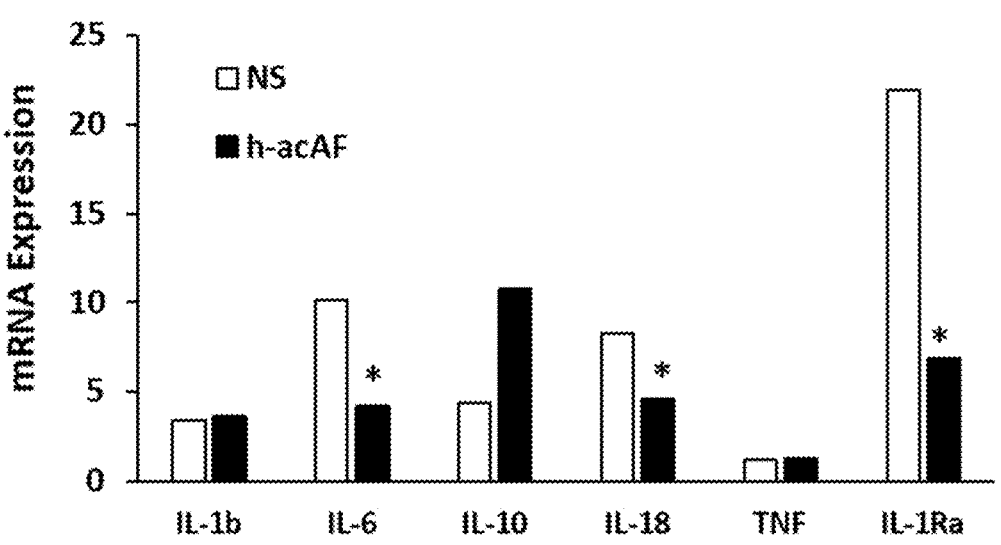
FIG. 9A shows a graph illustrating the immune system's response to ischemia reperfusion one week after I/R with h-acAF administration at 30 minutes post-reperfusion after 60 min ligation of proximal LAD coronary artery (90 min), by RT-PCR for Interleukin 1 beta (IL-1b), Interleukin 6 (IL-6), Interleukin 10 (IL-10), Interleukin 18 (IL-18), Tissue necrosis factor alpha (TNFα), Interleukin 1 receptor antagonist (IL1-Ra) in heart tissue (P<0.05, *vs NS treated).

FIG. 9A shows a graph illustrating the immune system's response to ischemia reperfusion one week after I/R with a group administered h-acAF after 30-minute reperfusion followed by 60-minute ligation of pLAD coronary artery (i.e., h-AF 90 min), by RT-PCR for Interleukin 1 beta (IL-1b), Interleukin 6 (IL-6), Interleukin 10 (IL-10), Interleukin 18 (IL-18), Tissue necrosis factor alpha (TNFα), and Interleukin 1 receptor antagonist (IL1-Ra) in heart tissue. The h-acAF treated group after 30-minute reperfusion followed by 60-minute ischemia (i.e., h-AF 90 min) demonstrated lower mRNA expressions of IL-6, IL-18, and IL-1Ra and increased tendency of IL-10 at 1 week after I/R compared with the N/S treated group after 30-minute reperfusion followed by 60-minute ischemia (i.e., N/S 90 min). The data was determined from the means±S.E.M. with *P<0.05 vs the N/S 90 min group.

Figure 9B:
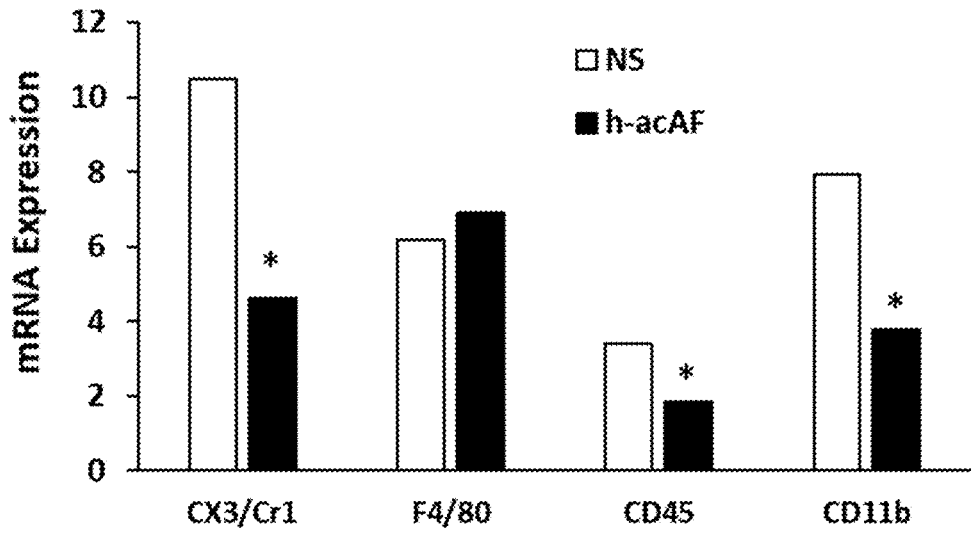
FIG. 9B shows a graph illustrating surface markers of the immune cells infiltrating into heart tissue one week after I/R with h-acAF administration at 30 minutes post-reperfusion after 60 min ligation of proximal LAD coronary artery (90 min), by RT-PCR for chemokine C-X3-C motif receptor 1 (Cx3cr1), Adhesion G protein-coupled receptor E1 (ADGRE1), receptor-like tyrosine phosphatase CD45 (CD45), cluster of differentiation molecule 11B (CD11b) (P<0.05, *vs NS treated).

FIG. 9B shows a graph illustrating surface markers of the immune cells infiltrating into heart tissue one week after I/R with h-acAF administration after 30-minute reperfusion followed by 60-minute ligation of pLAD coronary artery (i.e., h-AF 90 min), by RT-PCR for chemokine C-X3-C motif receptor 1 (Cx3cr1), Adhesion G protein-coupled receptor E1 (ADGRE1), receptor-like tyrosine phosphatase CD45 (CD45), cluster of differentiation molecule 11B (CD11b) (P<0.05, *vs NS treated). Cx3cr1, F4/80, CD45, and CD11b are surface markers of inflammatory and immune cells for adhesion and migration to infiltrate heart tissues. The expression of surface markers of Cx3cr1, CD45, and CD11b was decreased in the h-acAF treated group after 30-minute reperfusion followed by 60-minute ischemia (i.e., h-AF 90 min). The data was determined from the means±S.E.M. with *P<0.05 vs the N/S 90 min group. Balanced immuno-modulatory or anti-inflammatory therapeutic effects are important in cardiac repair after I/R injury. These findings imply that the overall inflammatory and immune-regulatory responses followed I/R injury were ameliorated by h-acAF treatment toward favorable functional and histology recovery than the N/S group.

Example 10

Sixty (60) Minutes of Ischemia-Reperfusion Injury Constructs Ischemic Heart Failure (iHF).

It is well known that post-infarct LV remodeling usually commences within the first few hours after an I/R injury. Typically, within a day of myocardial infarction, ischemic cardiac remodeling is characterized as infarct expansion, regional dilation, and thinning of the infarct zone.

To establish an ischemia-reperfusion injury rat model to test the effectiveness of using h-acAF to treat heart failure, an optimum time was identified for ligating the pLAD coronary artery and determined the amount of fluid to use for h-acAF injections. Ligation of the pLAD coronary artery was executed for 30, 45 or 60 min to assess the best ligation time to induce ischemic HF with significant functional deterioration. Cardiac injuries were examined at 1, 2, and 4 weeks post-ligation by echocardiography to determine ejection fractions. Significantly severe decreases of ejection factions occurred in animals receiving a 60 min pLAD ligation was confirmed as opposed to those animals using a 30 or 45 min pLAD ligation of the coronary artery (data not shown). The volume of h-acAF or N/S to use for injecting animals to treat I/R injuries was identified. Since total intramyocardial injection volumes of 250 or 300 μL of NS (N/S 60 min) resulted in higher postoperative mortalities in rats (pilot study), a total volume of 200 μL was selected.

Sham groups did not show significant functional changes, which could rule out surgical interference/bias on cardiac function in this model. Compared with sham groups, the N/S 60 min group showed hypokinetic wall motion abnormalities, marked LV dilatation (increased LV end-diastolic diameter, LVIDd and increased LV end-systolic diameter, LVIDs) and significant LV dysfunction (depressed EF %) by echocardiography, which progressed over the 4 weeks follow-up period (FIG. 2 and FIG. 3). The heart and lung weight were heavier (FIG. 7A-C), indicative of cardiac hypertrophy/ischemic remodeling and pulmonary congestion.

Example 11

Investigation of the Cardioprotective Effects of Novel Allogenic Acellular h-acAF (acAF) on Robust iHF Models.

Collection and Processing of Allogenic Human Amniotic Fluid (h-acAF) Allogenic h-acAF was collected from volunteer donors who met medical and social history criteria as established by the Federal Food and Drug Administration (FDA), the United States Public Health Service (USPHS), and the American Association of Tissue Banks (AATB). Donors were tested and found negative for the following: HBsAg (Hepatitis B Surface Antigen), HBcAb (hepatitis B core antibody), HCV (hepatitis C antibody), HIV I/II-Ab (Antibody to Human Immunodeficiency Virus Types 1 and 2), HIV NAT (HIV Nucleic Acid Test), HCV NAT (HCV Nucleic Acid Test), syphilis, and CMV (cytomegalovirus antibody screen). Screening for additional communicable diseases was based on donor responses to the medical and social history questionnaire by the medical director. Infectious disease testing was performed by laboratories who are FDA registered for HCT/Ps and certified under the Clinical Laboratory Improvement Amendments of 1988 (CLIA), (i.e., LABS, Inc., ARUP, Clongen, or VRL Laboratories).

Collection of h-acAF into sterile MediVac containers occurred during scheduled Caesarean-section as approved by the Institutional Review Board at the University of Utah and was transported to the Cell Therapy and Regenerative Medicine (CTRM) facility. Processing of h-acAF was performed as previously reported. Briefly, an aliquot of h-acAF was removed and designated for pre-processing microbio- logic testing for aerobic, anaerobic, and fungal microorgan- isms using the BACTEC system (Becton Dickinson, Sparks, MD). BACTEC Plus Aerobic/F, Plus Anaerobic/F, and a Myco F/Lytic culture bottles were each inoculated with 1 mL of AF. The bottles were then sent to ARUP Laboratories for culture and microorganism detection. Then the h-acAF was transferred via aseptic techniques into sterile conical tubes, centrifuged at 1400×g for 20 min at 4° C., the supernatant was collected and was processed using a pro- prietary filtration technology to obtain a sterile acellular h-acAF. Post-processing release testing included chemistry assessments for sodium, potassium, chloride, urea nitrogen, creatinine, and hyaluronic acid levels as determined by ARUP Laboratories (Salt Lake City, UT) and total proteins levels as determined by using a Pierce™ BCA Protein Assay Kit (Life Technologies, Grand Island, NY). Post-processing microbiology testing was conducted according to USP (71) pharmaceutical sterility guidelines.

Protein Arrays of h-acAF

AF (1 mL) from each of 4 donors (maternal collections) were sent to RayBiotech to quantitively measure the con- centration of 400 cytokines using the Quantibody® Human Cytokine Antibody Array 9000 (RayBiotech, In., Norcross, GA). Controls and serial dilutions of cytokine standards were prepared according to the manufacturer's instructions. Chips were blocked with 100 µL of Sample Diluent at room temperature for 30 min. After decanting the diluent from each chip, cytokine standards, controls and test samples were added to chip wells and were incubated at room temperature for 1-2 hrs. Each chip was washed three times and then incubated for 1 hr at room temperature in the dark with a Cy3 equivalent dye-streptavidin conjugate. The dye was decanted, and chips were washed 5 times with a 1× 40 wash buffer at room temperature, dried and imaged using a laser scanner equipped with a Cy3 wavelength. Quantitative data analysis was performed using the Quantibody® Q-Ana- lyzer software (RayBiotech, Inc.). Positive controls in each array were used for normalization. Classification of proteins according to biological function was obtained by surveying the Human Protein Reference Database (www.hprd.org/ index_html), Cytokines & Cells Online Pathfinder Encyclo- pedia (COPE) www.copewithcytokines.de/), GeneCards® (www.genecards.org/), and the biomedical literature in PubMed (www.ncbi.nlm.nih.gov/pubmed). Cluster Analysis was performed using the free software program from The R Project for Statistical Computing.

Ischemic HF (iHF) Model: Ischemia Reperfusion (I/R) Model in SD Rats

Male Sprague Dawley (SD) rats were purchased from Charles River Laboratories (Wilmington, MA) at 7-8 week of age with a body weight of 201-225 g. All rats were housed at the University of Utah animal facility under the Associa- tion for Assessment and Accreditation of Laboratory Animal Care International (AAALAC) guidelines. All experiments were approved by the University of Utah Institutional Ani- mal Care and Use Committee and followed the guidelines provided by the National Institutes of Health in Guide for the Care and Use of Laboratory Animals. All rats had access to food and water ad libitum and were housed in plastic cages on standard 12/12 hours light/dark cycles.

Ischemic heart failure was induced by performing a 60-minute surgical occlusion of the proximal left anterior descending (pLAD) coronary artery as previously described. This was followed by a 30 min reperfusion period prior to the heart being injected with saline or h-acAF. Briefly, under mechanical ventilation, the proximal LAD coronary artery was ligated for a 60-min period to occlude the artery. Successful ischemia was verified by the blanching of the myocardium, dyskinesia of the ischemic zone, and the ischemic changes in continuous ECG records, which indi- cates interruption of coronary flow. After 60 min of occlu- sion, the hemostat was removed, and the temporary suture snare was released for 30 min to achieve an ischemia/ reperfusion (IR) injury. Restoration of normal rubor indi- cated successful reperfusion of myocardium. Sham control animals were established by performing the same surgical procedure, with the exception of placing a loose suture around the coronary artery.

Ischemic HF (iHF) Model: Permanent Ligation Model in SD Rats

Chronic ischemic heart failure was induced by a perma- nent ligation with making double loops at the proximal LAD (pLAD) coronary artery with Prolene 7-0 suture (Ethicon). To investigate the cardio-protective efficacy of h-acAF in permanent ligation model, a single intravenous injection volume of 500 µL of h-acAF or 5 consecutive daily injec- tions of 500 µL (total 2,500 µL) of h-acAF were adminis- tered in different injection times: (i) right before a permanent ligation, (ii) after a permanent ligation, (iii) at 24 hours after permanent ligation, or (iv) at 2 weeks after ligation. (FIG. 11)

Echocardiography

Baseline echocardiographs were performed for sham and I/R animals and also at weeks 2 and 4 after the intramyo- cardial administration of NS or h-acAF. Echocardiograms were performed using a small animal echocardiography system (Vevo2100 High-Resolution Imaging System, Visual Sonics) equipped with a 13- to 24-MHz linear-array trans- ducer (MS250, MS400 MicroScan Transducer, Visual Son- ics). During performing echocardiograms, heart rates were tightly monitored between 350-400 per minutes while iso- flurane was administered between 1-2 L/minute. All mea- surements were averaged for three consecutive cardiac cycles.

Delineation of Acute Infarct Size

On the day of harvesting tissues, 2% weight to volume of 2,3,5-triphenyltetrazolium chloride (TTC) powder was dis- solved in phosphate buffered saline (PBS, pH 7.4) contained in a conical tube covered with aluminum foil for protection from ultraviolet light. At 24 hrs post-I/R injury, hearts were harvested and rinsed stepwise in PBS and potassium chlo- ride (2.51 M KCl) solution. Hearts were cut into 2 mm sections along short axis. Each section of heart was place in an individual well of a 24 well plate. With 2 mL of 2% TTC solution per well, the 24 well plate was incubated at 37° C. for 30 minutes in gentle shaking. At 15 minutes, heart sections were flipped over on the other side in 24 well plate. Heart sections were transferred to 10% phosphate buffered formalin for 90 minutes and rinsed in PBS solution before imaging. Images were taken under a stereomicroscope (Olympus SZX10 and U-TV0.5XC-3, Tokyo, Japan).

Measurement of Cardiac-Specific Troponin

Ischemic HF was confirmed by determining troponin I (TnI) levels in serum samples, which were collected at 24 hrs after I/R injury. Ten percent of the animal's total blood volume (TBV) was withdrawn via the jugular vein. The blood was allowed to clot at room temperature for 20 minutes, then was centrifuged at 2,500 RPM for 15 minutes at 4° C. The supernatant or serum was separated and TnI levels were determined using the rat cardiac Troponin I ELISA kit (ab246529, Abcam).

Quantitative Reverse Transcriptase Polymerase Chain Reaction

After RNA isolation, real-time polymerase chain reaction was performed using the QuantStudio 12K Flex System with Power SYBR Green PCR Master Mix (Applied Biosystems). Gene expression levels were calculated in accordance with the 2-ΔΔct method and normalized to 16s.

Histopathology

After evaluation of echocardiography at 4 weeks, hearts were quickly harvested following euthanasia of animals under isoflurane. Heart tissue was embedded in paraffin and serial sagittal (longitudinal) sections of rat myocardium were cut, fixed, and stained with Masson's trichrome. The extent of fibrosis was determined by measuring the extent of blue staining or collagen staining that was present in the myocardium. Analysis of all images was done using ImageJ and ImageScope (Aperio Technologies, Vista, CA).

Statistical Analysis

All data were expressed as mean±SEM. Comparisons between multiple groups were performed by analysis of variance followed by Tukey post-hoc testing. A P value<0.05 was considered statistically significant.

Example 12

Diverse Routes of Administration of h-acAF Reveal Consistent Therapeutic Efficacy and Expand the Clinical Application and Accessibility.

Route of Administration: Intramyocardial Injections

Animals were assigned to one of six groups: (i) normal saline injection in sham control animals (n=4), (ii) h-acAF injection in sham control (n=4), (iii) N/S injection immediately before the start of 60-minute ischemia injury (i.e., N/S 0 min) (n=9) (iv) h-acAF injection immediately before the start of 60-minute ischemia injury (i.e., h-AF 0 min) (n=8) (v) N/S injection after 30 minute reperfusion followed by 60-minute ischemia (i.e., N/S 90 min) (n=9) (vi) h-acAF injection after 30 minute reperfusion followed by 60-minute ischemia (i.e., h-AF 90 min) (n=8). The sham group underwent surgical procedures similar to the h-AF 90 min group but with a loose stitch around the coronary arteries. The sham group did not undergo a 60-minute ligation of the pLAD (proximal left anterior descending) coronary artery before release. Sham control and I/R animals received a total injection volume of 200 μL of NS or h-acAF, respectively. NS and h-acAF were delivered via 8 separate intramyocardial sites with 6 injections to the ischemic border zone and 2 injections to central zone of the infarct in LV with a 30-gauge needle (FIG. 1B). Animals were followed for 4 weeks after injections and harvested to collect hearts, lungs, and blood.

Route of Administration: Intravenous Injections

An intramyocardial administration of h-acAF demonstrated prominent cardio-protective effects on I/R injury model. In clinical relevance and expanded accessibility, we designed whether intravenous (IV) administration of h-acAF disclose the efficacy of h-acAF in I/R injury model via jugular vein (making a detour from the first pass metabolism in liver). To evaluate the efficacy of intravenous injections of h-acAF, the volume of 100 μL, 200 μL, or 500 μL was injected at the start of reperfusion after 60 min of ligation in the I/R injury model (FIG. 10). With cardio-protective effects of a single injection of 500 μL of h-acAF, the injection volume of h-acAF was titrated and lowered into 200 μL and 100 μL in the 60-minute I/R injury model. Different intravenous injection volume with 100, 200, and 500 μL of h-acAF revealed significant cardio-protective effects at the start of reperfusion right after 60-minute of ligation. Intravenous injection of h-acAF at the start of reperfusion after 60-minute of ischemia injury showed more preserved systolic function in LV (EF %) and less dilated dimensions in LV (LVIDd and LVIDs).

Figure 10A:
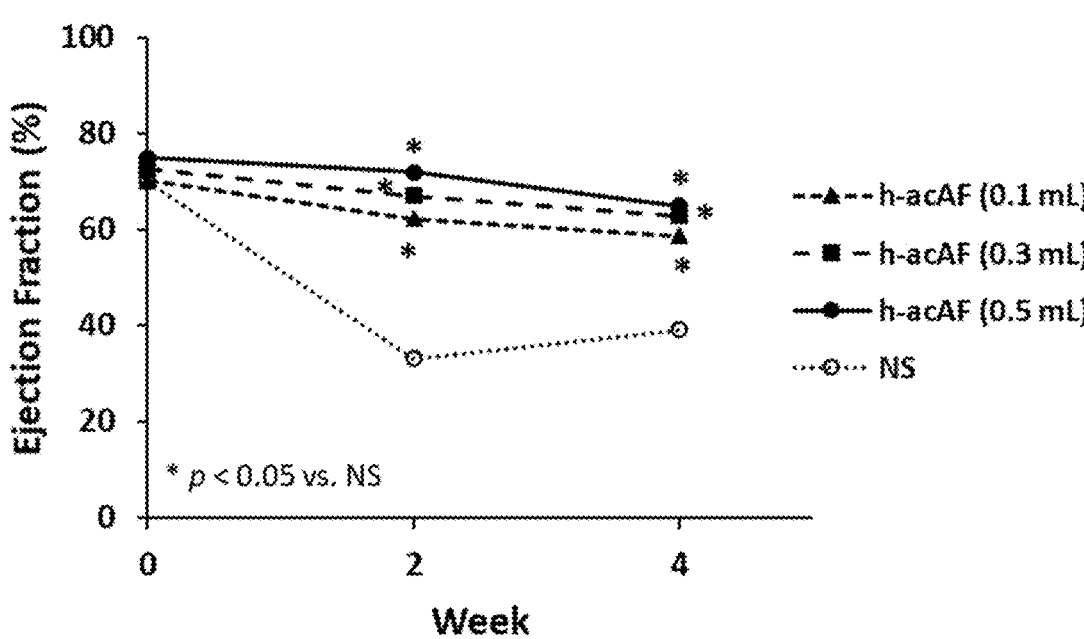
FIG. 10A shows a graph illustrating that a single intravenous injection of h-acAF right after 60 min ligation of proximal LAD coronary artery with different injection volumes (100 μL, 200 μL, and 500 μL) can improve systolic function in LV (EF) at 2 weeks after injections and 4 weeks after injections (P<0.05, *vs NS treated).

FIG. 10A shows a graph illustrating that a single intravenous injection of h-acAF right after 60-minute ligation of proximal LAD (pLAD) coronary artery with different injection volumes (100 μL, 200 μL, and 500 μL) can improve systolic function in LV (EF %) at 2 weeks after injections and 4 weeks after injections. (P<0.05, *vs NS treated).

Figure 10B:
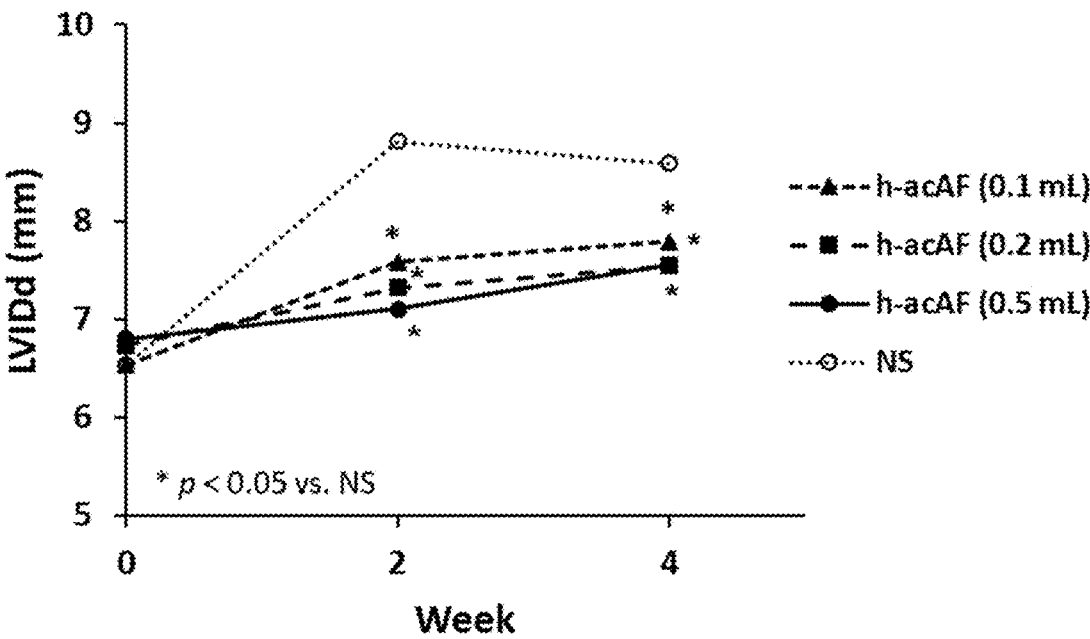
FIG. 10B shows a graph illustrating that a single intravenous injection of h-acAF right after 60 min ligation of proximal LAD coronary artery with different injection volumes (100 μL, 200 μL, and 500 μL) can recover favorable cardiac geometry as measured by LVIDd at two time periods from the baseline: 2 weeks after treatment (injections); and 4 weeks after treatment (injections) (P<0.05, *vs h-AF treated).

FIG. 10B shows a graph illustrating that a single intravenous injection of h-acAF right after 60-minute ligation of proximal LAD (pLAD) coronary artery with different injection volumes (100 μL, 200 μL, and 500 μL) can recover favorable cardiac geometry as measured by LVIDd at two time periods from the baseline: 2 weeks after treatment (injections); and 4 weeks after treatment (injections). (P<0.05, *vs h-AF treated).

Figure 10C:
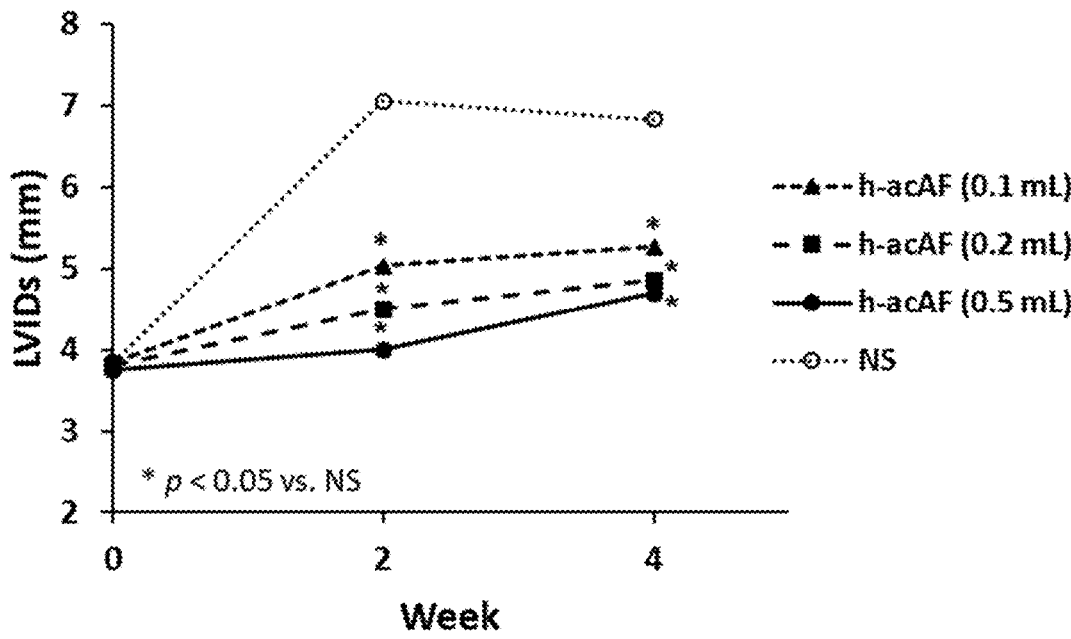
FIG. 10C shows a graph illustrating that a single intravenous injection of h-acAF right after 60 min ligation of proximal LAD coronary artery with different injection volumes (100 μL, 200 μL, and 500 μL) can recover favorable cardiac geometry as measured by LVIDs at two time periods from the baseline: 2 weeks after treatment (injections); and 4 weeks after treatment (injections) (P<0.05, *vs h-AF treated).

FIG. 10C shows a graph illustrating that a single intravenous injection of h-acAF right after 60-minute ligation of proximal LAD (pLAD) coronary artery with different injection volumes (100 μL, 200 μL, and 500 μL) can recover favorable cardiac geometry as measured by LVIDs at two time periods from the baseline: 2 weeks after treatment (injections); and 4 weeks after treatment (injections). (P<0.05, *vs h-AF treated).

Example 13

Intravenous Administrations of h-acAF in Permanent Ligation Model with Exploring Different Injection Times Demonstrate the Early Cardiac Prevention Against Deterioration of Chronic Ischemic Heart Failure.

Figure 11A:
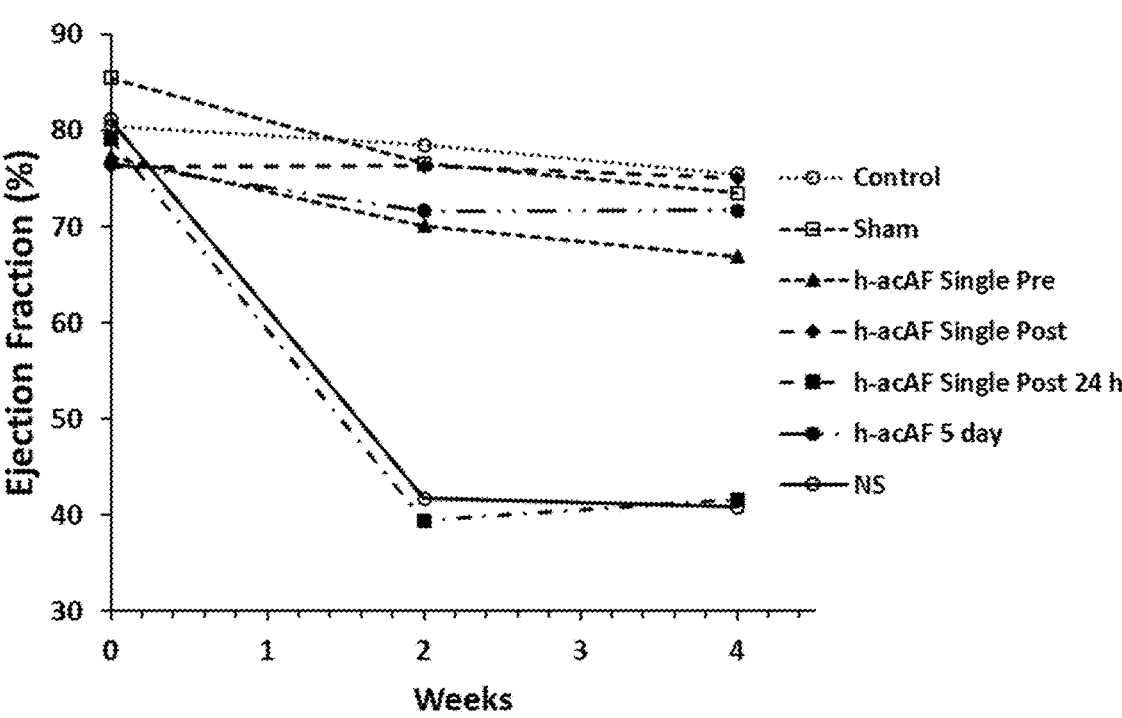
FIG. 11A shows a graph illustrating that a single intravenous injection of h-acAF (500 μL) right before permanent ligation or right after permanent ligation protects from ischemic injury cascade of the ischemic heart failure (iHF) by permanent ligation. A single IV injection of 500 µL of h-acAF right before permanent ligation or right after permanent ligation can recover systolic function in LV (EF %) at 2 weeks after injections and 4 weeks after injections. Consecutive daily injections of h-acAF for 5 days (500 µL×5 days) starting right after permanent ligation demonstrate comparable functional improvements. Delayed injection after 24 hours followed by permanent ligation is not enough to rescue systolic function in LV (%) in permanent ligation model.

To investigate the efficacy of h-acAF in permanent ligation model, a single or consecutive (for 5 days with daily 500 μL) IV administrations of h-acAF were introduced in different injection times via jugular vein: (i) right before a permanent ligation, (ii) after a permanent ligation, (iii) at 24 hours after permanent ligation, or (iv) at 2 weeks after ligation (FIG. 11). h-acAF therapy opens a promising prospect as an 'in situ regenerative niche (i.e., panacea)' for cardiac tissue regeneration by the induction of favorable post-infarct cardiac remodeling covering functional, geometric, cellular, histopathological, and molecular level. The feasible allogenic h-acAF would be a crucial therapeutic conduit to support lessening the I/R injury and protecting against ischemic injury in clinic. This scaffold-free allogenic h-acAF is a 'smart biomolecule factory (i.e., reservoir)' for the cardiac application as well as precision medicine in the near future. FIG. 11A shows a graph illustrating that a single intravenous injection of 500 μL of h-acAF right before permanent ligation or right after permanent ligation protects from ischemic injury cascade of iHF by permanent ligation. A single IV injection of 500 μL of h-acAF right before permanent ligation or right after permanent ligation can recover systolic function in LV (EF %) at 2 weeks after injections and 4 weeks after injections. Consecutive daily injections of h-acAF for 5 days (500 μL×5 days) starting right after permanent ligation demonstrate comparable functional improvements. Delayed injection after 24 hours followed by permanent ligation is not enough to rescue systolic function in LV (%) in permanent ligation model.

Figure 11B:
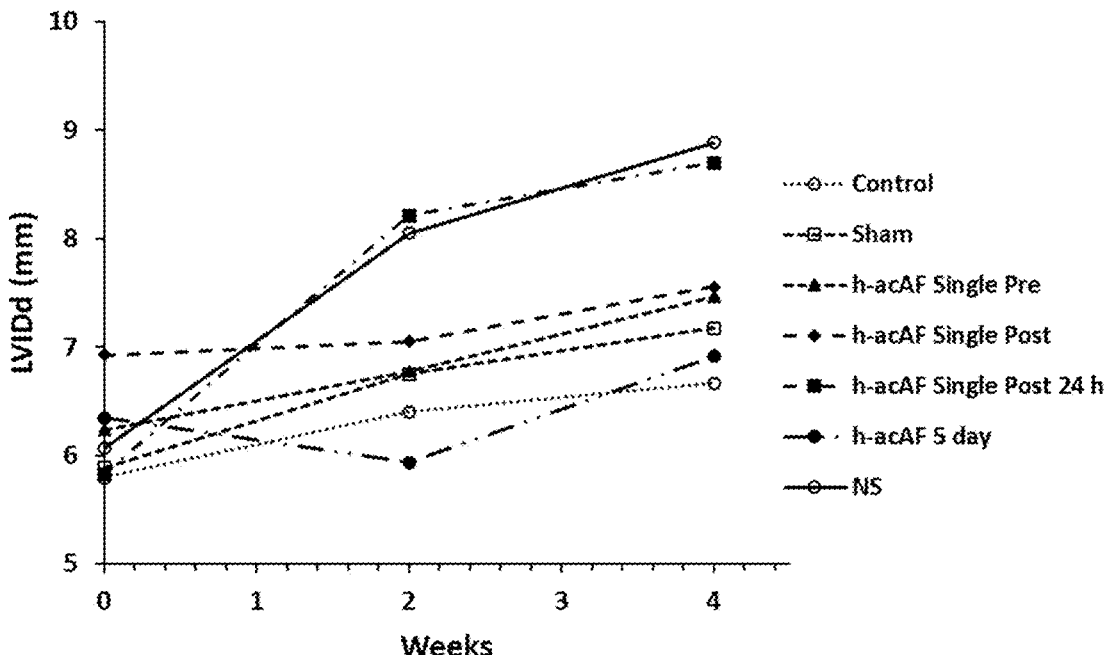
FIG. 11B shows a graph illustrating that a single intravenous injection of h-acAF (500 µL) right before permanent ligation or right after permanent ligation protects from the ischemic heart failure, can recover favorable cardiac geometry as measured by LVIDd at 2 weeks after injections and 4 weeks after injections.

FIG. 11B shows a graph illustrating that a single intravenous injection of h-acAF (500 µL) right before permanent ligation or right after permanent ligation protects from the ischemic heart failure, can recover favorable cardiac geometry as measured by LVIDd at 2 weeks after injections and 4 weeks after injections.

Figure 11C:
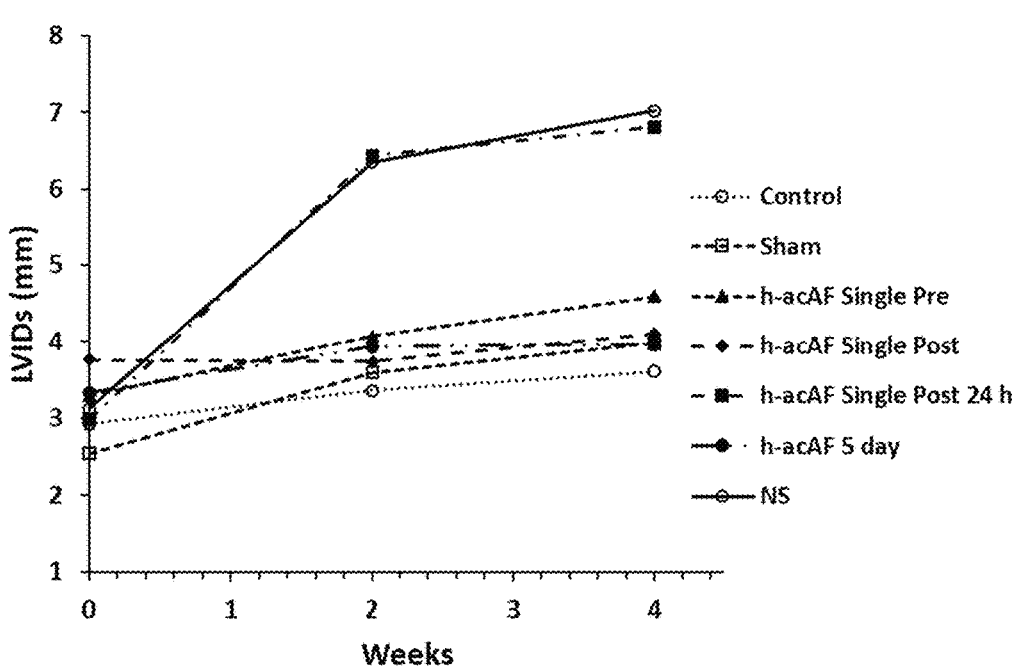
FIG. 11C depicts a graph showing that a single intravenous injection of h-acAF (500 µL) right before permanent ligation or right after permanent ligation protects from the ischemic heart failure, can recover favorable cardiac geometry as measured by LVIDs at 2 weeks after injections and 4 weeks after injections.

FIG. 11C depicts a graph showing that a single intravenous injection of h-acAF (500 µL) right before permanent ligation or right after permanent ligation protects from the ischemic heart failure, can recover favorable cardiac geometry as measured by LVIDs at 2 weeks after injections and 4 weeks after injections.

Figure 11D:
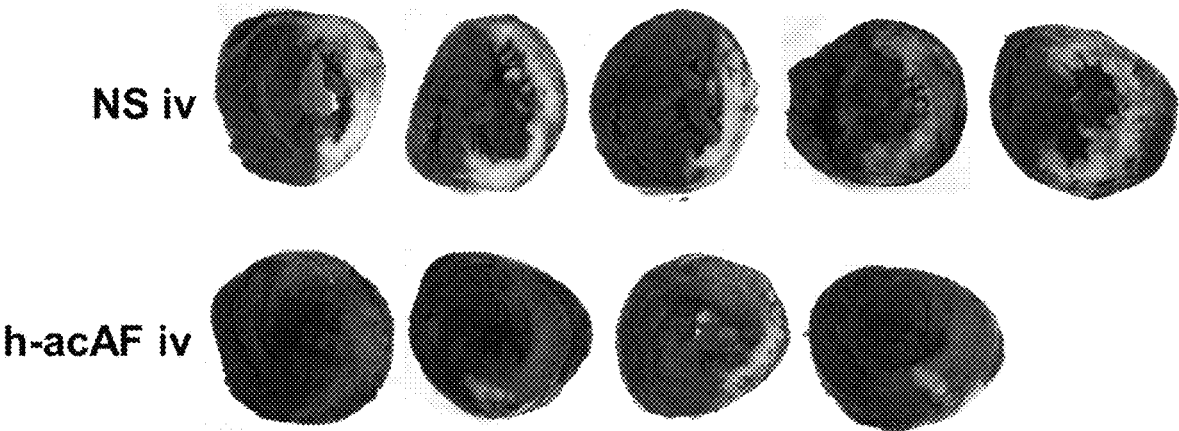
FIG. 11D shows a photo array illustrating that intravenous administration of h-acAF (500 µL) right after permanent ligation (via jugular vein) can reduce infarct size and area at risk with dual staining of Evans blue and TTC in heart tissues harvested at 24 hours after permanent ligation, compared with N/S (500 µL) injections. Injection of h-acAF (500 µL) or N/S (500 µL) was randomized in rats after permanent ligation. To measure area at risk and infarct size, rats were injected with Evans Blue through the apex of LV and stained with TTC solution at 24 hours after a permanent ligation.

FIG. 11D shows a photo array illustrating that intravenous administration of h-acAF (500 µL) right after permanent ligation (via jugular vein) can reduce infarct size and area at risk with dual staining of Evans blue and TTC in heart tissues harvested at 24 hours after permanent ligation, compared with N/S injections. Injection of h-acAF (500 µL) or N/S (500 µL) was randomized in rats after permanent ligation. To measure area at risk and infarct size, rats were injected with Evans Blue through the apex of LV and stained with TTC solution at 24 hours after a permanent ligation.

What is claimed is:

1. A method of treating an ischemic injury in a subject, comprising:
   locally injecting a therapeutically effective amount of an acellular amniotic fluid (acAF) to an ischemic injury situs within a therapeutic time window.

2. The method of claim 1, wherein the acAF is substantially free of cells and debris.

3. The method of claim 1, wherein the ischemic injury situs is an organ selected from: a heart, a brain, a limb, a large intestine, a small intestine, a stomach, a liver, a gallbladder, a pancreas, a lung, a kidney, a lymph node, a thymus, a spleen, a skeletal muscle, a smooth muscle, a cardiac muscle, an artery, a vein, or combinations thereof.

4. The method of claim 1, wherein the ischemic injury is ischemia/reperfusion or permanent ligation.

5. The method of claim 1, wherein the therapeutic time window includes one or more of: 30 minutes, 60 minutes, one day, 1 week, 2 weeks, or 4 weeks.

6. The method of claim 1, wherein administration is performed via an intravenous injection, wherein the ischemic injury situs is a vein.

7. The method of claim 1, wherein the therapeutically effective amount of acAF has less than or equal to 10,000 particles per milliliter of particles having a particle size of 10 microns or greater.

8. The method of claim 1, wherein the therapeutically effective amount of acAF has less than or equal to 300 particles per milliliter of particles having a particle size of 25 microns or greater.

9. The method of claim 1, wherein the therapeutically effective amount of acAF has an optical density of less than 0.20 when exposed to electromagnetic radiation at a wavelength of 590 nm.

10. The method of claim 1, wherein the therapeutically effective amount of acAF further comprises hemoglobin in an amount from 1 µg/mL to 60 µg/mL.

11. The method of claim 1, wherein the therapeutically effective amount of acAF further comprises an active agent.

12. The method of claim 11, wherein the active agent is an anti-infective agent, an antibiotic, an anti-tumor agent, an anti-inflammatory agent, a pain-controlling agent, an anti-rheumatic agent, a bisphosphonate, a supplementary growth factor, a supplementary cytokine, an amino acid, a protein, a vaccine, a hormone, a vitamin, a phytoestrogen, a fluoride, or combinations thereof.

13. The method of claim 11, wherein the active agent is: angiotensin-converting enzyme (ACE) inhibitors, aldosterone inhibitors, angiotensin II receptor blockers (ARBs), beta-blockers, calcium channel blockers, cholesterol-lowering drugs, digoxin, diuretics, potassium, magnesium, proprotein convertase subtilisin kexin type 9 (PCSK9) inhibitors, vasodilators, warfarin, or combinations thereof.

14. The method of claim 11, wherein the active agent further comprises stem cells.

15. The method of claim 1, wherein the therapeutically effective amount of acAF further comprises a pharmaceutically acceptable carrier.

16. The method of claim 1, wherein the therapeutically effective amount includes a volume of therapeutic composition of from about 0.1 mL to about 1000 mL.

17. The method of claim 1, wherein the therapeutically effective amount includes an amount of total protein from about 0.1 mg to about 2500 mg.

18. The method of claim 1, wherein the therapeutically effective amount includes an amount of hyaluronic acid (HA) from about 0.1 mg to about 2500 mg.

19. A method of treating a cardiac ischemic event in a subject, comprising:
   locally injecting a therapeutically effective amount of acellular amniotic fluid (acAF) to an ischemic situs of a heart of the subject within a therapeutic time window.

20. The method of claim 19, wherein the therapeutic time window includes one or more of: 30 minutes, 60 minutes, one day, 1 week, 2 weeks, or 4 weeks.

21. The method of claim 19, wherein local injection is performed via one or more of: direct administration into a myocardium of the heart of the subject via an epicardial injection or an endocardial injection; intravenous injection to the subject; intracoronary administration; or direct administration to a coronary vein of the heart of the subject.

22. The method of claim 19, wherein local injection is performed concomitantly with a procedure directed to the heart of the subject, wherein the procedure includes one or more of: cardiac catheterization, coronary angioplasty, balloon angioplasty, coronary artery stent, atherectomy, laser angioplasty, coronary artery bypass surgery, intra-aortic balloon pump surgery, ventricular assist device (VAD) surgery, heart transplant surgery, valvuloplasty, valve repair surgery, valve replacement surgery, or combinations thereof.

23. The method of claim 19, wherein the therapeutically effective amount of acAF has less than or equal to 10,000 particles per milliliter of particles having a particle size of 10 microns or greater.

24. The method of claim 19, wherein the therapeutically effective amount of acAF has less than or equal to 300 particles per milliliter of particles having a particle size of 25 microns or greater.

25. The method of claim 19, wherein the therapeutically effective amount of acAF has an optical density of less than 0.20 when exposed to electromagnetic radiation at a wavelength of 590 nm.

26. The method of claim 19, wherein the therapeutically effective amount of acAF further comprises a pharmaceutically acceptable carrier.

27. The method of claim 19, wherein the therapeutically effective amount includes a volume of therapeutic composition of from about 25 µL to about 25 mL.

28. The method of claim 19, wherein the therapeutically effective amount of acAF further comprises an active agent selected from: angiotensin-converting enzyme (ACE) inhibitors, aldosterone inhibitors, angiotensin II receptor blockers (ARBs), beta-blockers, calcium channel blockers, cholesterol-lowering drugs, digoxin, diuretics, potassium, magnesium, proprotein convertase subtilisin kexin type 9 (PCSK9) inhibitors, vasodilators, warfarin, or combinations thereof.

29. A method of treating fibrosis in a subject, comprising:
locally injecting a therapeutically effective amount of acellular amniotic fluid (acAF) to an ischemic situs of the subject within a therapeutic time window.

30. A method of treating peripheral arterial disease (PAD) in a subject, comprising:
locally injecting a therapeutically effective amount of acellular amniotic fluid (acAF) to an ischemic situs of a lower extremity of the subject within a therapeutic time window.

31. A method of treating cyanosis in a subject, comprising:
locally injecting a therapeutically effective amount of acellular amniotic fluid (acAF) to an ischemic situs of an extremity of the subject, wherein the therapeutically effective amount is administered via a dosage regimen.

* * * * *